United States Patent
Salaita et al.

(10) Patent No.: US 9,708,665 B2
(45) Date of Patent: Jul. 18, 2017

(54) SPATIAL BIOMARKER OF DISEASE AND DETECTION OF SPATIAL ORGANIZATION OF CELLULAR RECEPTORS

(75) Inventors: Khalid S. Salaita, Decatur, GA (US); Pradeep M. Nair, San Francisco, CA (US); Debopriya Das, Albany, CA (US); Joe W. Gray, Lake Osewego, OR (US); John T. Groves, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/194,577

(22) Filed: Jul. 29, 2011
(Under 37 CFR 1.47)

(65) Prior Publication Data
US 2012/0178104 A1 Jul. 12, 2012

Related U.S. Application Data

(63) Continuation of application No. PCT/US2010/022671, filed on Jan. 29, 2010.

(60) Provisional application No. 61/148,203, filed on Jan. 29, 2009, provisional application No. 61/176,858, filed on May 8, 2009.

(51) Int. Cl.
*G01N 33/53* (2006.01)
*C12Q 1/68* (2006.01)

(52) U.S. Cl.
CPC ..... *C12Q 1/6886* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,637,201 A | 6/1997 | Raguse et al. | |
| 5,885,613 A | 3/1999 | Holland et al. | |
| 5,942,397 A | 8/1999 | Tarlov et al. | |
| 6,228,326 B1 | 5/2001 | Boxer et al. | |
| 6,329,209 B1 | 12/2001 | Wagner et al. | |
| 2002/0160505 A1 | 10/2002 | Groves et al. | |
| 2004/0053337 A1 | 3/2004 | Yamazaki et al. | |
| 2005/0244487 A1 | 11/2005 | Sansinena et al. | |
| 2008/0292546 A1 | 11/2008 | Clarke et al. | |
| 2009/0011428 A1 | 1/2009 | Nam et al. | |
| 2009/0177450 A1 | 7/2009 | Gray et al. | |
| 2012/0121582 A1* | 5/2012 | Kinch et al. | 424/133.1 |
| 2012/0315216 A1* | 12/2012 | Clarke et al. | 424/1.49 |

FOREIGN PATENT DOCUMENTS

| | | |
|---|---|---|
| WO | 98/23948 A1 | 6/1998 |
| WO | 01/20330 A1 | 3/2001 |
| WO | 01/26800 A1 | 4/2001 |
| WO | 03/051506 A1 | 6/2003 |
| WO | 2006/081158 A2 | 8/2006 |

OTHER PUBLICATIONS

Boxer (2000) Current Opiinions in Chem. Biol. 4:704-709.*
Pasquale et al. (1997) Current Opinion in Cell Biology 9: 608-615.*
Coffman et al. (2003) Cancer Research 63: 7907-7912.*
Salaita et a. (2010) Science 327: 1380-1385.*
Pasquale, E. B. et al. (Apr. 4, 2008). "Eph-Ephrin Bidirectional Signaling in Physiology and Disease," Cell 133:38-52.
Ponta, H. et al. (Jan. 2003). "CD44: From Adhesion Molecules to Signaling Regulators," Nature Reviews Molecular Cell Biology 4:33.
Provenzano, P. P. et al. (Dec. 2008). "Contact Guidance Mediated Three-Dimensional Cell Migration is Regulated by Rho/ROCK-Dependent Matrix Reorganization," Biophysical Journal 95(11):5374-5384.
Salafsky, J. et al. (1996). "Architecture and Function of Membrane Proteins in Planar Supported Bilayers: A Study with Photosynthetic Reaction Centers," Biochemistry 35(47):14773-14781.
Storey, J. D. et al. (Aug. 5, 2003). "Statistical Significance for Genomewide Studies," Proceedings of the National Academy of Sciences of the United States of America 100(16):9440-9445.
Taddei, M. L. et al. (Apr. 2009). "Kinase-Dependent and —Independent Roles of EphA2 in the Regulation of Prostate Cancer Invasion of Metastasis," The American Journal of Pathology 174(4):1492-1503.
Thaker, P. H. et al. (Aug. 1, 2004). "EphA2 Expression is Associated with Aggressive Features in Ovarian Carcinoma," Clinical Cancer Research 10:5145-5150.
U.S. Office Action mailed Apr. 21, 2011, for U.S. Appl. No. 12/161,553, filed Jul. 21, 2008, 9 pages.
U.S. Office Action mailed Jan. 4, 2012, for U.S. Appl. No. 12/161,553, filed Jul. 21, 2008, 8 pages.
Vargo-Gogola, T. et al. (Sep. 2007) "Modelling Breast Cancer: One Size Does Not Fit All," Nature Reviews Cancer 7:659-672.
Verschueren, H. et al. (1985). "Interference Reflection Microscopy in Cell Biology: Methodology and Application," Journal of Cell Science 75:279-301.
Walker-Daniels, J. et al. (Apr. 2003). "Differential Regulation of EphA2 in Normal and Malignant Cells," American Journal of Pathology 162(4):1037-1042.
Walker-Daniels, J. et al. (Nov. 2002). "c-Cbl-Dependent EphA2 Protein Degradation is Induced by Ligand Binding," Molecular Cancer Research 1:79-87.

(Continued)

*Primary Examiner* — Michael Pak
(74) *Attorney, Agent, or Firm* — Michelle Chew Wong; Lawrence Berkeley National Laboratory

(57) ABSTRACT

A signature of a condition of a live cell is established in an assay that allows distribution of the receptors on the cell surface in response to binding a ligand. The receptors can be optically detected and quantified to provide a value for the condition, Test drugs can be screened for therapeutic potential in the assay: a potentially efficacious drug is identified by an ability to modulate an established signature. The receptor distribution signature can be corroborated with an mRNA expression profile of several genes, indicating, for example, metastasis.

13 Claims, 21 Drawing Sheets

(56) References Cited

OTHER PUBLICATIONS

Figure 2:
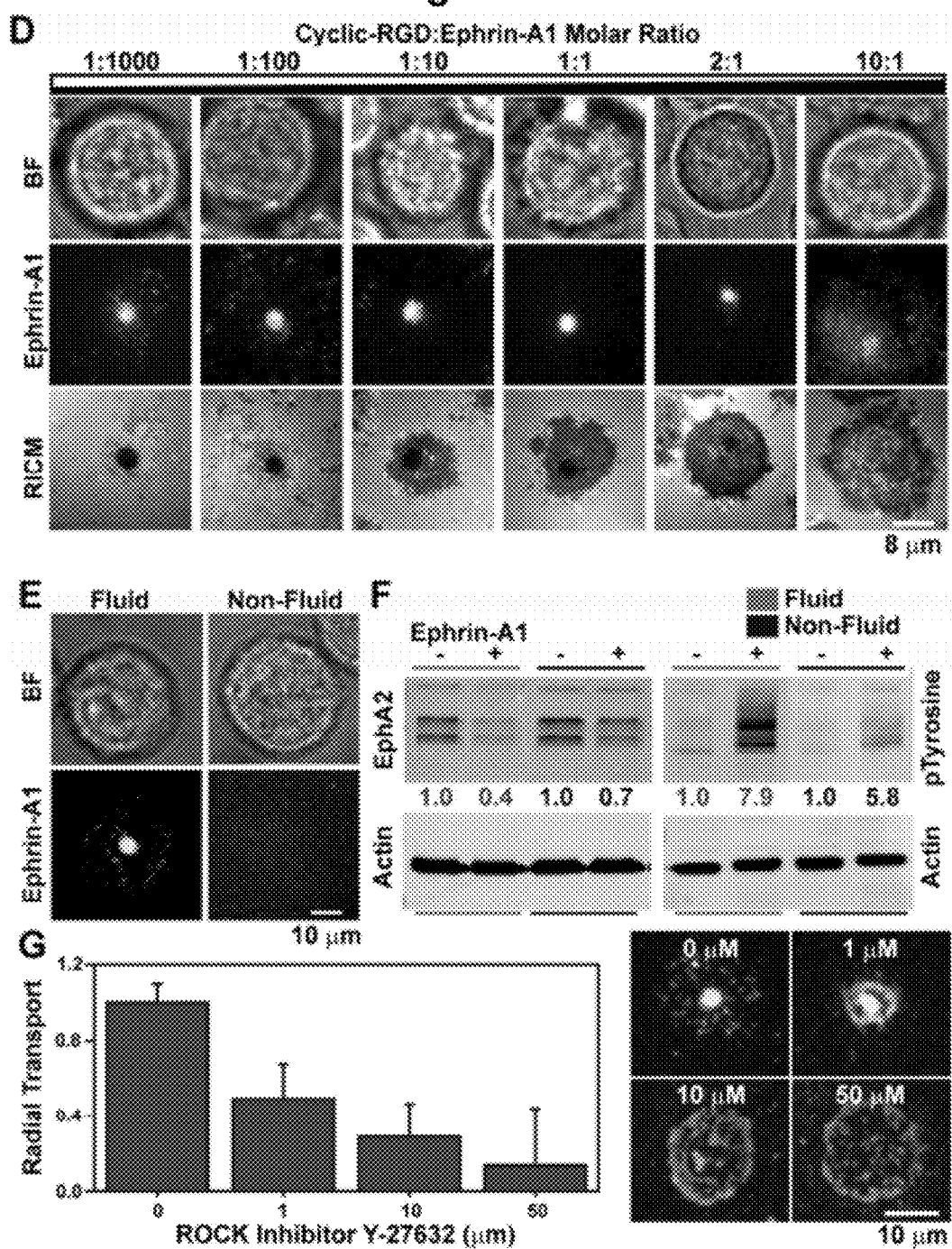

Wehland, J. et al. (1979). "Cell-to-Substratum Contacts in Living Cells: A Direct Correlation Between Interference-Reflexion and Indirect-Immunofuorescence Microscopy Using Antibodies Against Actin and alpha-Actinin," Journal of Cell Science 37:257-273.
Wheeler, D. B. et al. (Nov. 2004). "RNAi Living-Cell Microarrays for Loss-of-Function Screens in *Drosophila melanogaster* Cells," Nature Methods 1(2):1-6.
Zelinski, D. P. et al. (Mar. 1, 2001). "EphA2 Overexpression Causes Tumorgenesis of Mammary Epithelial Cells," Cancer Research 61:2301-2306.
Zhang, X. et al. (Jun. 16, 2006). "An Allosteric Mechanism for Activation of the Kinase Domain of Epidermal Growth Factor Receptor," Cell 125:1137-1149.
Ziauddin, J. et al. (May 3, 2001). "Microarrays of Cells Expressing Defined cDNAs," Nature 411:107-110.
Bailey, S. N. et al. (Nov. 16, 2004). "Microarrays of Small Molecules Embedded in Biodegradable Polymers for Use in Mammalian Cell-Based Screens," Proceedings of the National Academy of Sciences of the United States of America 101(46):16144-16149.
Ballestrem, C. et al. (1998). "Actin Dynamics in Living Mammalian Cells," Journal of Cell Science 111:1649-1658.
Boldog, T. et al. (Aug. 1, 2006). "Nanodiscs Separate Chemoreceptor Oligomeric States and Reveal their Signaling Properties," Proceedings of the National Academy of Sciences of the United States of America 103 (31):11509-11514.
Boxer, S. G. et al. (2000). "Molecular Transport and Organization in Supported Lipid Membranes," Current Opinion in Chemical Biology 4:704-709.
Carter, N. et al. (Aug. 2002). "EphrinA1-Induced Cytoskeletal Re-Organization Requires FAK and p130cas," Nature Cell Biology 4:565-573.
Chen, C. S. (2008). "Mechanotransduction—A Filed Pulling Together?," Journal of Cell Science 121(20): 3285-3292.
Dalby, M. J. et al. (Dec. 2007). "The Control of Human Mesenchymal Cell Differentiation Using Nanoscale Symmetry and Disorder," Nature Materials 6:997-1003.
Das, D. et al. (2006). "Adaptively Inferring Human Transcriptional Subnetworks," Molecular Systems Biology, article No. 2006.0029, pp. 1-14.
Davis, M. M. et al. (2003). "Dynamics of Cell Surface Molecules During T Cell Recognition," Annual Review of Biochemistry 72:717-742.
Davis, S. et al. (Nov. 4, 1994). "Ligands for EPH-Related Receptor Tyrosine kinases that Require Membrane Attachment or Clustering for Activity," Science 266:816-819.
Day, B. et al. (Jul. 15, 2005). "Three Distinct Molecular Surfaces in Ephrin-A5 are Essential for a Functional Interaction with EphA3," The Journal of Biological Chemistry 280(28):26526-26532.
DeMond, A. L. et al. (Apr. 2008). "T Cell Receptor Microcluster Transport Through Molecular Mazes Reveals Mechanism of Translocation," Biophysical Journal 94(8):3286-3292.
Dennis Jr., G. et al. (2003). "DAVID: Database for Annotation, Visualization, and Integrated Discovery," Genome Biology 4(9):R60.1-R60.11.
Discher, D. E. et al. (Nov. 18, 2005). "Tissue Cells Feel and Respond to the Stiffness of their Substrate," Science 310:1139-1143.
Dobrzanski, P. et al. (Feb. 1, 2004). "Antiangiogenic and Antitumor Efficacy of EphA2 Receptor Antagonist," Cancer Research 64:910-919.
Drubin, D. G. et al. (Feb. 9, 1996). "Origins of Cell Polarity," Cell 84:335-344.
Duxbury, M. S. et al. (2004). "Ligation of EphA2 by Ephrin A1-Fc Inhibits Pancreatic Adenocarcinoma Cellular Invasiveness," Biochemical and Biophysical Research Communications 320:1096-1102.
Friedl, P. et al. (May 2003). "Tumour-Cell Invasion and Migration: Diversity and Escape Mechanisms," 3:362-374.
Galush, W. J. et al. (Sep. 2008). "Quantitative Fluorescence Microscopy Using Supported Lipid Bilayer Standards," Biophysical Journal 95(5):2512-2519.
Groves, J. T, et al. (2002). "Micropattern Formation in Supported Membranes," Accounts of Chemical Research 35 (3):149-157.
Groves, J. T. et al. (2003). "Supported Planar Bilayers in Studies on Immune Cell Adhesion and Communication," Journal of Immunological Methods 278:19-32.
Harding, A. D. et al. (2008). "Using Plasma Membrane Nanoclusters to Build Better Signaling Circuits," Trends in Cell Biology 18(8):364-371.
Hartman, N. C. et al. (Aug. 4, 2009). "Cluster Size Regulates Protein Sorting in the Immunological Synapse," Proceedings of the National Academy of Sciences of the United States of America 106(31):12729-12734.
Hattori, M. et al. (Aug. 25, 2000). "Regulated Cleavage of a Contact-Mediated Axon Repellent," Science 289:1360-1365.
Himanen, J. et al. (Dec. 20/27, 2001). "Crystal Structure of an Eph Receptor-Ephrin Complex," Nature 414:933-938.
Himanen, J. et al. (May 2004). "Repelling Class Discrimination: Ephrin-A5 Binds to and Activates EphB2 Receptor Signaling," Nature Neuroscience 7(5):501-509.
Humphries, J. D. et al. (2006). "Integrin Ligands at a Glance," Journal of Cell Science 119(19):3901-3903.
International Search Report and Written Opinion mailed Dec. 16, 2008, for PCT Application No. PCT/US07/60721 filed Jan. 18, 2007, 7 pages.
International Search Report and Written Opinion mailed Oct. 13, 2010, for PCT Application No. PCT/US10/22671 filed Jan. 29, 2010, 9 pages.
Ireton, R. C. et al. (2005). "EphA2 Receptor Tyrosine Kinase as a Promising Target for Cancer Therapeutics," Current Cancer Drug Targets 5(3):149-157.
Izzard, C. S. et al. (1976). "Cell-to-Substrate Contacts in Living Fibroblasts: An Interference Reflexion Study with an Evaluation of the Technique," Journal of Cell Science 21:129-159.
Jackson, B. L. et al. (2004). "Scanning Probe Lithography on Fluid Lipid Membranes," Journal of the American Chemical Society 126(43):13878-13879.
Janes, P. W. et al. (Oct. 21, 2005). "Adam Meets Eph: An ADAM Substrate Recognition Module Acts as a Molecular Switch for Ephrin Cleavage in Trans," Cell 123:291-304.
Koolpe, M. et al. (Dec. 6, 2002). "An Ephrin Mimetic Peptide that Selectively Targets the EphA2 Receptor," The Journal of Biological Chemistry 277(49):46974-46979.
Kullander, K. et al. (Jul. 2002). "Mechanisms and Functions of Eph and Ephrin Signaling," Nature Reviews Molecular Cell Biology 3:475-486.
Lackmann, M. et al. (Apr. 15, 2008). "Eph, a Protein Family Coming of Age: More Confusion, Insight, or Complexity?," Science Signaling, pp. 1-16, available at www.stke.org/cgi/content/full/1/15/re2.
Landen, C. N. et al. (2005). "EphA2 as a Target for Ovarian Cancer Therapy," Expert Opinion on Therapeutic Targets 9(6):1179-1187.
Landen, C. N. et al. (Nov. 1, 2006). "Efficacy and Antivascular Effects of EphA2 Reduction with an Agonistic Antibody in Ovarian Cancer," Journal of the National Cancer Institute 98(21):1558-1570.
Macrae, M. et al. (Aug. 2005). "A Conditional Feedback Loop Regulates Ras Activity Through EphA2," 8:111-118.
Mannix, R. J. et al. (Jan. 2008). "Nanomagnetic Actuation of Receptor Mediated Signal Transduction," 3:36-40.
Maretzky, T. et al. (Jun. 28, 2005). "ADAM10 Mediates E-Cadherin Shedding and Regulates Epithelial Cell-Cell Adhesion, Migration, and beta-Catenin Translocation," Proceedings of the National Academy of Sciences of the United States of America 102(26):9182-9187.
Miao, H. et al. (Feb. 2000). "Activation of EphA2 Kinase Suppresses Integrin Function and Causes Focal-Adhesion-Kinase Dephosphorylation," Nature Cell Biology 2:62-69.
Mochizuki, S. et al. (May 2007). "ADAMs in Cancer Cell Proliferation and Progression," Cancer Science 98 (5):621-628.

(56) References Cited

OTHER PUBLICATIONS

Monks, C. R. F. et al. (Sep. 3, 1998). "Three-Dimensional Segregation of Supramolecular Activation Clusters in T Cells," Nature 395:82-86.
Moss, M. L. et al. (2008). "ADAM10 as a Target for Anti-Cancer Therapy," Current Pharmaceutical Biotechnology 9 (1):2-8.
Mossman, K. D. et al. (Nov. 18, 2005). "Altered TCR Signaling from Geometrically Repatterned Immunological Synapses," 310:1191-1191.
Murthy, V. N. et al. (2003). "Cell Biology of the Presynaptic Terminal," Annual Review of Neuroscience 26:701-728.
Nam, J. et al. (2006). "A Fluid Membrane-Based Soluble Ligand-Display System for Live-Cell Assays," ChemBioChem 7:436-440.
Naor, D. et al. (1997). "CD44: Structure, Function, and Association with the Malignant Process," Advances in Cancer Research, pp. 241-319.
Neve, R. M. et al. (Dec. 2006). "A Collection of Breast Cancer Cell Lines for the Study of Functionally Distinct Cancer Subtypes," Cancer Cell 10:515-527.

\* cited by examiner

Figure 1
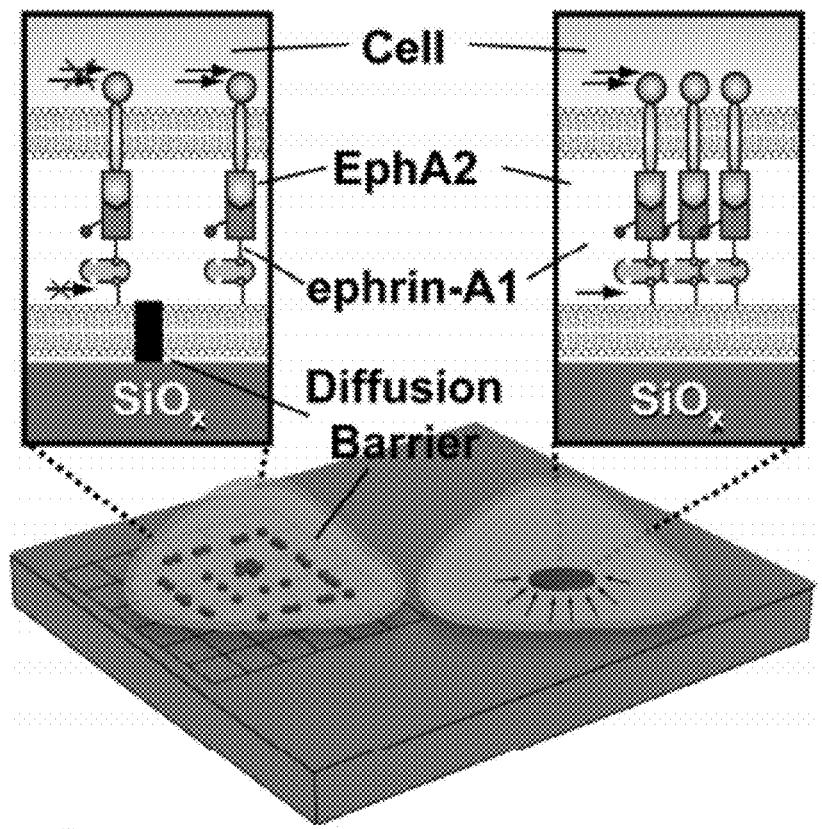
Figure 2
A
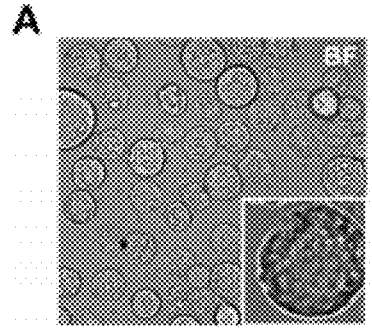
B Radial Transport
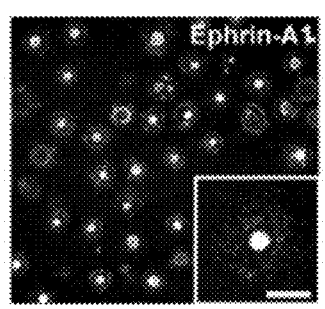
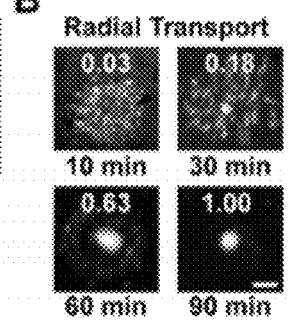
C
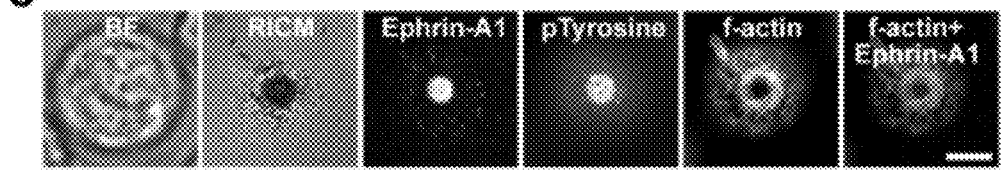

Figure 3
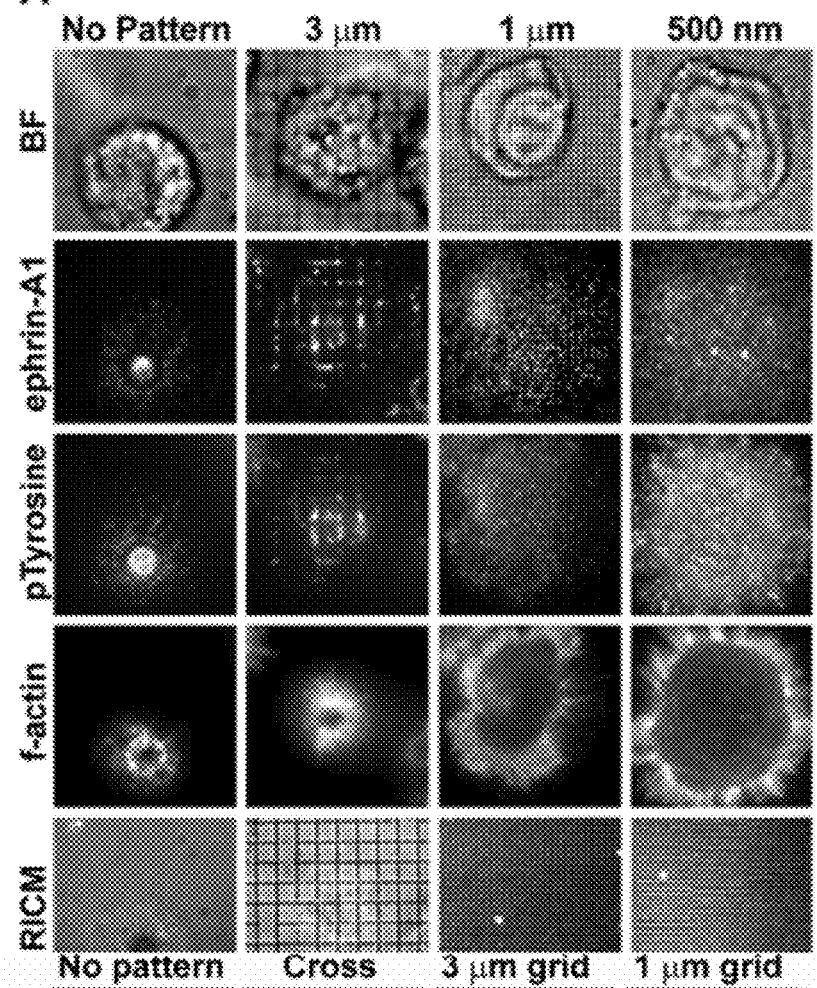
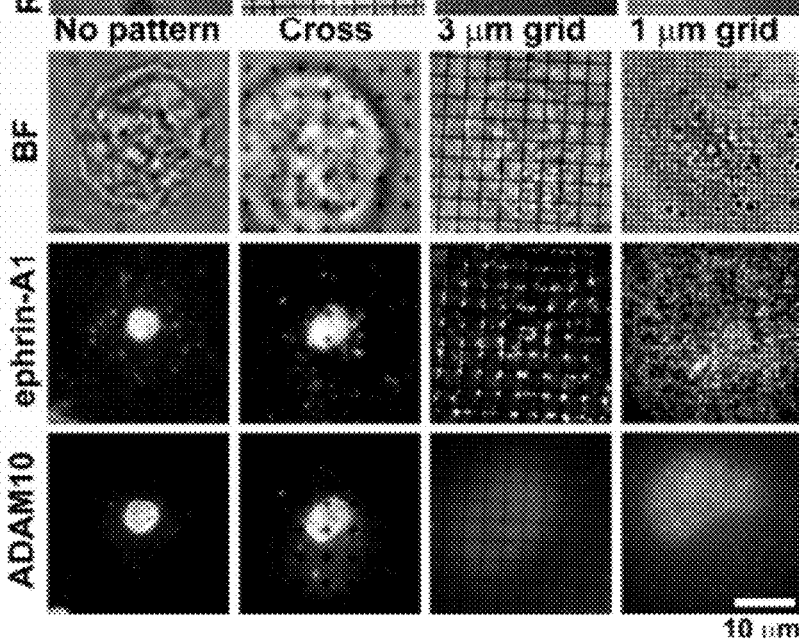

Figure 6:
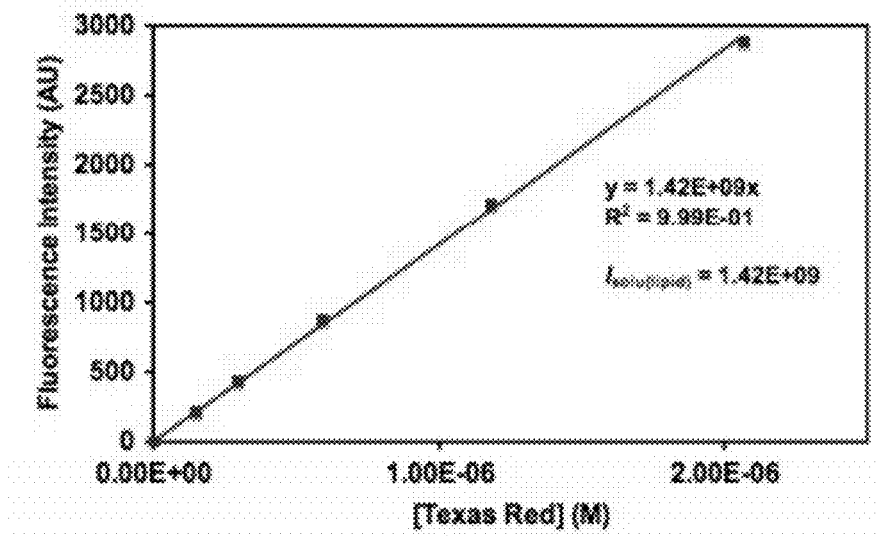
Figure 6:
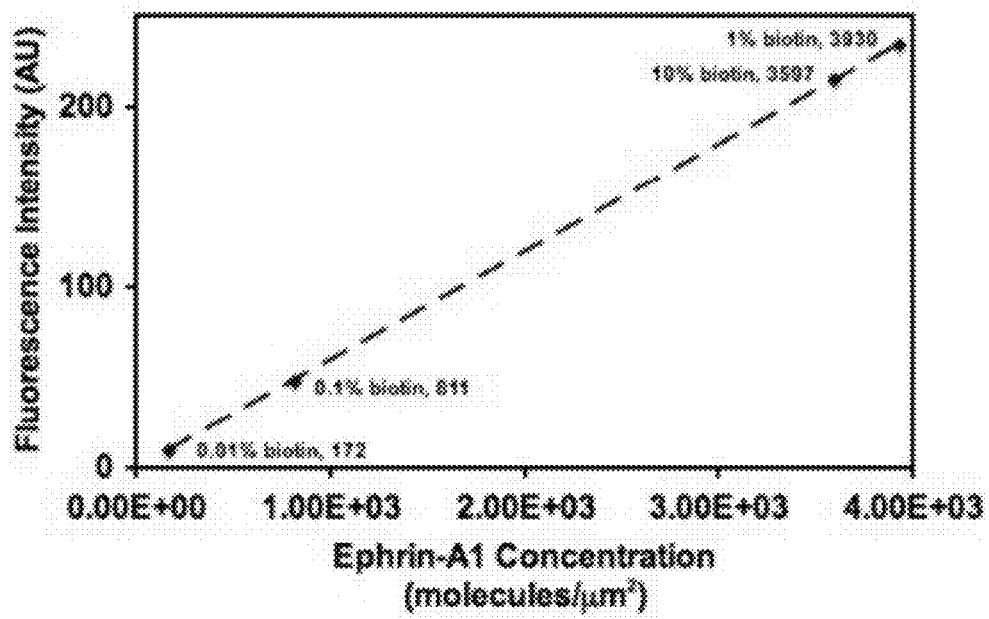

Figure 6
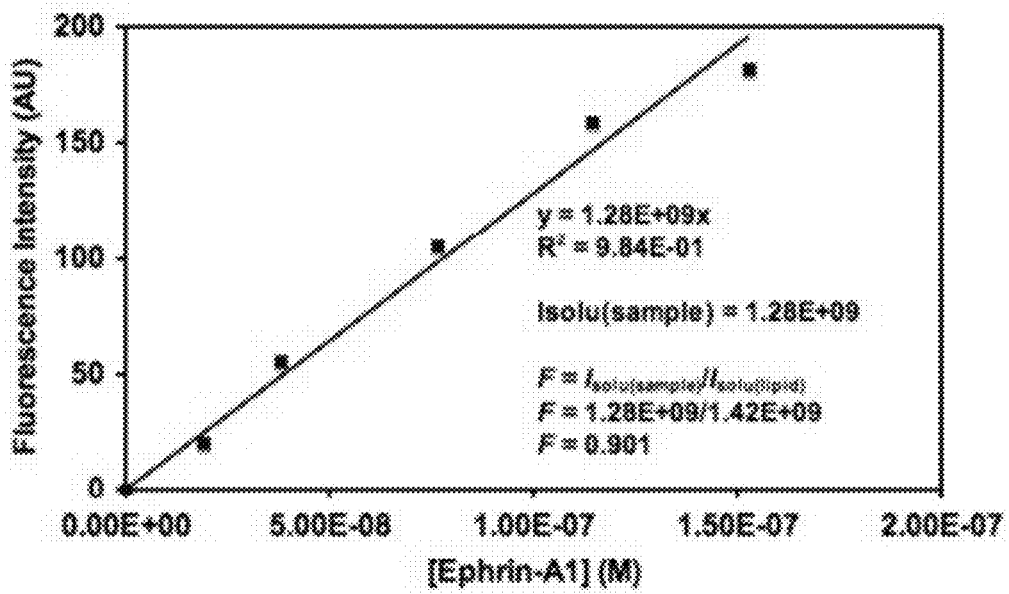
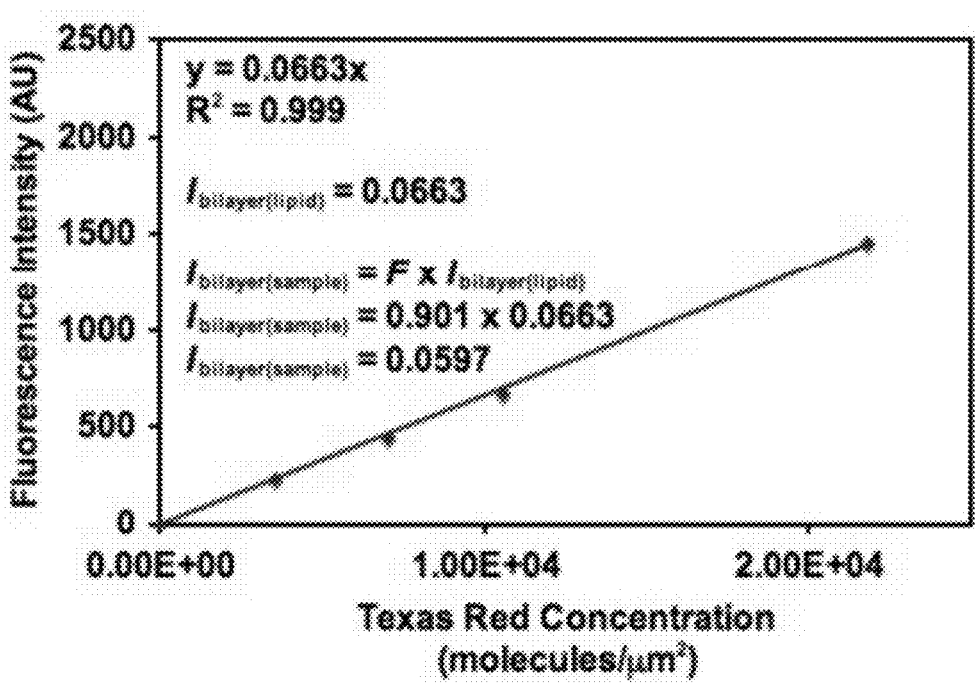

D Bilayer Ephrin-A1 (Calculated)

Flow Cytometry FITC Calibration

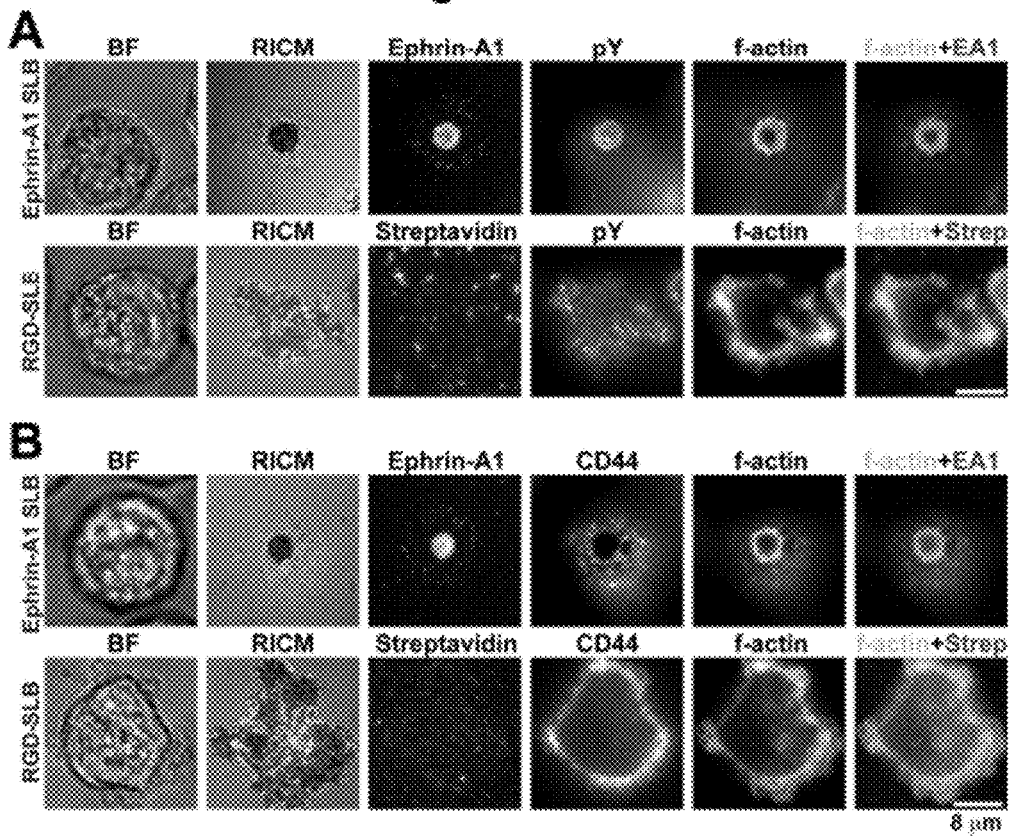
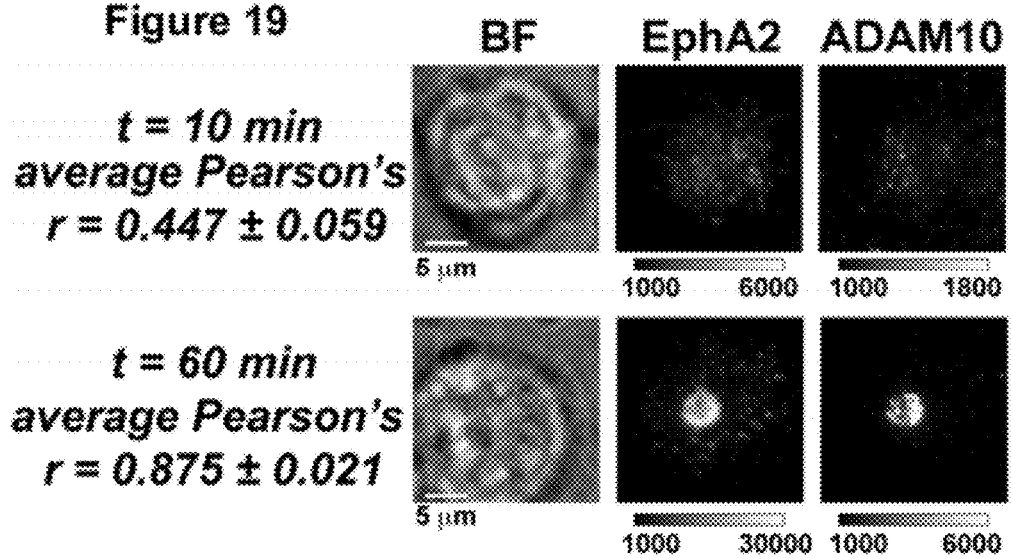

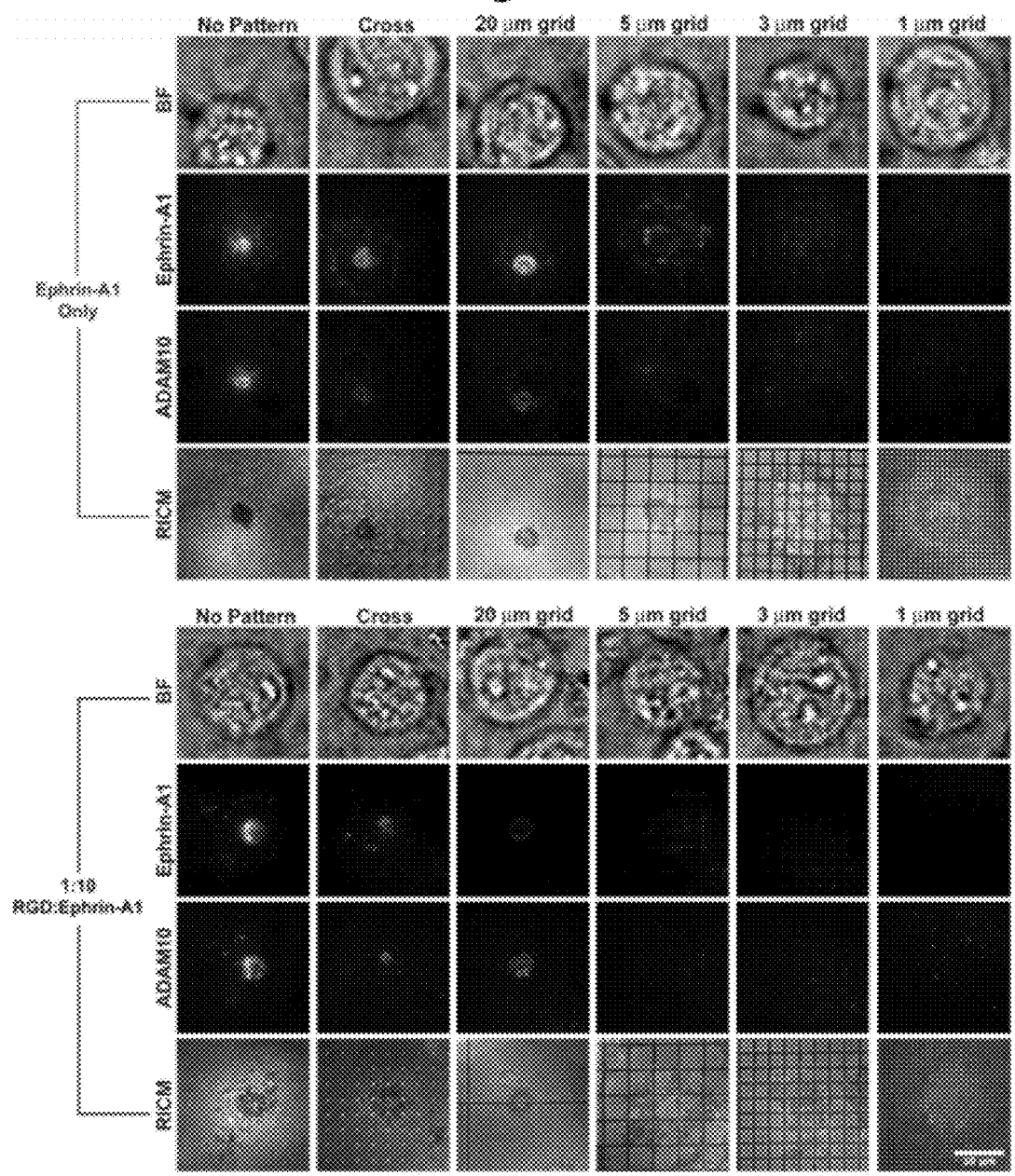

SPATIAL BIOMARKER OF DISEASE AND DETECTION OF SPATIAL ORGANIZATION OF CELLULAR RECEPTORS

CROSS-REFERENCE TO RELATED APPLICATIONS

The application claims priority to PCT International Application No. PCT/US2010/022671, filed Jan. 29, 2010, which claims priority to U.S. Provisional Patent Application No. 61/148,203, filed Jan. 29, 2009, and U.S. Provisional Patent Application No. 61/176,858, filed on May 8, 2009, each of which is hereby incorporated by reference in its entirety.

The application hereby incorporates by reference in its entirety, co-pending U.S. patent application Ser. No. 12/161,553, filed on Jul. 21, 2008, entitled, "A Fluid Membrane-Based Ligand Display System for Live Cell Assays and Disease Diagnosis Applications."

STATEMENT OF GOVERNMENTAL SUPPORT

This work was supported by Contract No. DE-AC02-05CH11231 awarded by the Department of Energy, by U.S. Department of Defense Breast Cancer Research Program Concept Award BC076701 under U.S. Army Medical Research Acquisition Activity No. W81XWH-08-1-0677, and by grants P50 CA 58207, and by the U54 CA 112970 awarded by the National Institutes of Health, National Cancer Institute. The government has certain rights in the invention.

FIELD OF THE INVENTION

The invention relates to in vitro and live cell assays using supported fluid membrane systems and lipid bilayers.

BACKGROUND OF THE INVENTION

In mammals, cellular communication is mediated by cell-surface molecules, or receptors, that are present on the membrane surface of all mammalian cells. Cell-surface molecules are activated by binding a molecule outside the cell. Interaction with the molecule causes the receptor to change, move, realign, reorganize and redistribute on the cell surface and activate the cell. The molecule outside the cell can be a cell-surface molecule on another cell, or an unattached independent binding molecule.

Binding or otherwise interacting with the external molecule results in dimerization or oligomerization of the receptor on the cell surface, which in turn initiates a cascade of biochemical signals that are relayed to molecules within the cell. Molecules within the cell then convey directions for other events, the most common of which is a change in transcription and expression of a gene known to be "downstream" of the receptor in a pathway. After expression of the genes that have been "turned on", more events and consequences occur in the cell. These consequences and events are manifested in mammals in conditions and states of the cell's tissue source. A simple condition is healthy tissue. A more complicated condition is diseased tissue. It is foundational that basic scientific research done for development of medical advances is attempting to address how to alter cell activity in diseased tissue in order to direct the tissue to heal, and the disease to reverse.

Structural characterization of receptor associations during receptor-mediated cell activation has been studied in a number of labs. See e.g., (R. J. Mannix et al., *Nature Nanotechnology* 3, 36 (Jan., 2008); A. S. Harding, J. F. Hancock, *Trends in Cell Biology* 18, 364 (Aug., 2008); T. Boldog, S. Grimme, M. Li, S. G. Sligar, G. L. Hazelbauer, *Proceedings of the National Academy of Sciences* 103, 11509 (Aug. 1, 2006); X. Zhang, J. Gureasko, K. Shen, P. A. Cole, J. Kuriyan, *Cell* 125, 1137 (2006)).

On a micrometer scale, protein interactions involving multiple protein complexes is critical to cell signaling, particularly in the juxtacrine type signaling found in adhesion junctions. See e.g. (D. G. Drubin, W. J. Nelson, *Cell* 84, 335 (Feb. 9, 1996)), the neuronal synapse (V. N. Murthy, P. De Camilli, *Annual Review of Neuroscience* 26, 701 (2003)), and the immunological synapse (C. R. F. Monks, B. A. Freiberg, H. Kupfer, N. Sciaky, A. Kupfer, *Nature* 395, 82 (Sep. 3, 1998)).

Deconstructing what cell-surface signaling molecules do after binding an ligand is a challenge because of the chemical heterogeneity of the cell membrane and the complexity of effecting cell-cell contact in an in vitro system. However, the challenge may be worth addressing. Future directions for diagnosis and treatment of many complicated and illusive diseases, the hallmark of which is cancer, seem to point towards patient-specific targeting of a disease condition.

While genetic screening and protein expression profiling can yield information, they fall short of elucidating in vivo receptor function and behavior. These current techniques are usually indirect by design with respect to activation on the cell surface, and cannot be expected to perform beyond their limits, especially with regard to the challenge of decoding the complex events that activate the cell from a receptor at the surface. There is a need for assays that convey accurate information about the behavior of cells derived from tissue exhibiting the condition.

SUMMARY OF THE INVENTION

The present invention includes an assay using live cells. Cells from biopsies or other tissue samples of patients can also be used in the assay. In one aspect, the invention identifies a signature devised from quantifying receptor distribution on the cell surface after binding a ligand. The receptor distribution signature can be optically detected. The receptor distribution signature can be corroborated by detecting downstream expression of a set of genes that correlate to a condition.

The assay conditions and platform of the assay allow a binding ligand residing external to the cell, to bind a cell-surface molecule, e.g., a receptor or ligand. Upon binding of the ligand to the cell, typically a complex of several bound molecules, e.g., receptors and ligands, is formed on the cell surface. The complex is identified by the assay as an activation complex.

A physical context is adapted in the assay to facilitate an interaction between one or more external binding ligands and at least one cell-surface molecule on a live cell. The physical context can comprise a soluble lipid bilayer for retaining the binding ligands. The physical context can be adapted to allow formation of an activation complex on the surface of the cell, the activation complex comprising one or more binding ligands and one or more cell-surface molecules.

The assay can include access of a test drug to the cell-surface molecule and at least one external binding ligand for testing an ability of the drug to modulate an interaction that causes cell activation (most typically the interaction between the binding ligand external to the cell and the cell-surface receptor, which interaction is most typically a binding interaction). For quantification purposes, the pre-defined portion of the intact cell surface is a region having an approximate span between about 10 nanometers and about 10 microns on the cell surface. The live cell is most usefully derived from human tissue.

The patterns of ligand-receptor binding pairs that form the "signatures" can be compared between any number of cell types, sources, conditions, etc. For example, of healthy and diseased cells can be compared for establishment of the relative differences between the two. That information can be used to functional assays for cellular analysis of the diseased state. So, for example, as applied to cancer, different cancers and different stages of the same cancer can be studied.

Preferred cell sources are live tissues. The cells can be derived from any living tissue. Mammalian tissue is appropriate for the assay because all mammalian cells express cell-surface receptors and all mammalian cells are activated by ligands binding cell-surface receptors. Accordingly, the live cells for the assay can be derived from human tissues. Assays that employ live cells have been difficult to create. In one embodiment, the assay generates a signature that can be correlated to the condition of the tissue. The activation signature that results can be correlated to some aspect (state, stage, condition, quality, identify, character, aspect, or other indicia) of the tissue from which the cell came. The activation signature in the assay is redistribution of the cell-surface molecule on the cell surface after interaction with the ligand.

In one aspect, of the instant invention, the assay captures the activities of the cell-surface molecule, and uses the changes of location of the receptor on the cell surface as a readout (a "signature") that can be correlated to the condition of the tissue from which the cell was derived. The ligand may be a cell surface molecule also, and as such is able to bind the cell surface receptor on the target cell.

The present assay conditions are described with which to generate cell activation signatures for all types of cells from tissues of any type of condition known to mammals. Developed here is a broad-based tool for diagnosis, prognosis and drug efficacy screening that uses an optically detectable redistribution of activated receptors on the cell surface as a "signature" that can be scored.

In another aspect of the invention, in the assay, the ligand is retained within a substrate, such as a soluble lipid bilayer and presented to the live cell. Other physical environments and constructs may also be used to present the ligand to the live cell, including microwells, tubes, spheres (e.g. the ligand attached to a sphere or bead or particle in a solution), and other artificial structures that can retain or present the ligand to the live cell (e.g. vessels, structures, substrates or platforms). The ligand can be in a cell membrane of a different live cell, thus presenting an option for conducting the assay in a three-dimensional (3D) physical context, i.e., the cell's environment, such as a contained solution or other controlled environment that mimics solution-like interaction between the molecules or cells. A 3D assay may require optically detection of changes in receptor distribution on the surface of the activated live cell in the solution.

In another aspect, a method of identifying a redistribution of receptors on the cell surface upon binding a molecule that causes cell activation includes quantifying the redistribution of the receptor on the cell surface, and correlating "activation signature" of the receptor redistribution with a condition of the tissue. The physical context of the assay is adapted to allow a live cell having a receptor to interact with an ligand external to the cell. The redistribution can be detected and quantified on a portion of the cell surface having an approximate span between about 10 nanometers and about 10 microns on the cell surface.

In another aspect, a test drug having a potential to modulate live cell activation can be scored in the assay for a live cell activation value based on quantifying the redistribution of the receptor. These methods can be conducted on an adapted lipid bilayer, such as a soluble lipid bilayer.

In another aspect, a composition of matter comprising an activated live cell isolated from mammalian tissue comprising a plurality of redistributed receptors displaying a post-activation signature comprising a signature that can be to correlated to the tissue or condition from which the cell was taken.

In another aspect of the invention, a cell can be scored for activation is with expression of downstream genes after receptor-mediated cell activation. Such transcriptional events are detected in the examples shown here, and are, for example as EFNA1, GRB7, ITGB1, ITGB2, CAV2 and LYN for the specific receptor and ligand pair studied.

The present invention also provides methods of diagnosing or prognosing a disease such as cancer. The activation or radial distribution score calculated from the expression levels of a gene can be interpolated to a curve of scored EphA2 radial transport vs. invasion potential, obtained from a library of cell lines with measured invasion potentials.

BRIEF DESCRIPTION OF THE DRAWINGS AND TABLES

FIG. 1 depicts spatial organization of receptor signaling corresponds to an accumulation of receptor-ligand complexes at Cr diffusion barriers created for the assay.

FIG. 2 shows the identification of central assembly domain (CAD) and formation of the CAD during EphA2 engagement to ephrin-A1 ligand. FIG. 2(A) shows representative bright field and epifluorescence images of MDA-MB-231 cells within 1 hr of interaction with an Alexa Fluor 647-tagged ephrin-A1 functionalized supported membrane. FIG. 2(B) shows dynamics of receptor-ligand reorganization as a function of time. The radial distribution of ephrin-A1 was measured under each cell and the population average value (n=77 cells) is indicated above the fluorescence image for each time point. FIG. 2(C) shows that the central EphA2 cluster is the region of highest ephrin-A1 concentration, greatest tyrosine phosphorylation and tightest cell adhesion to the substrate, and results in reorganization of the actin cytoskeleton to form a peripheral annulus (Scale bar is 5 µm in A-C). FIG. 2(D) shows the representative bright field, epifluorescence, and reflection interference contrast microscopy images of cells 1 hr after plating on a supported membrane functionalized with binary mixtures of ephrin-A1 and cyclic RGD peptide. Ephrin-A1 and RGD were incubated in the molar ratios indicated above each panel, and show EphA2 translocation regardless of the area of the cell-supported membrane contact. FIG. 2(E) shows the mechanical reorganization of EphA2 requires a fluid membrane. Bilayers composed of 99.9% DPPC and 0.1% Biotin-DPPE are not fluid during cell engagement at 37° C. and, as a result, no long-range EphA2 reorganization is observed on DPPC bilayers. FIG. 2(F) shows images of the western blots of lysates collected from $1 \times 10^5$ cells cultured onto fluid and non-fluid membranes. Presentation of fluid ephrin-A1 results in more rapid and complete EphA2 activation than presentation of non-fluid ephrin-A1, as measured by EphA2 degradation and total pY intensities. EphA2 bands are at a mass of ~100 kDa. FIG. 2(G) shows when cells were treated with the Rho kinase inhibitor Y-27632, a dosage-dependent decrease in Eph-ephrin radial transport was observed (n=627 cells), demonstrating that the cytoskeleton drives radial transport. Experiments were performed in duplicate, and radial transport was independently normalized to untreated samples from each replicate FIG. 3 shows the functional consequences of EphA2 spatial mutation. Lateral transport of the EphA2 receptor is hindered by nanoscale lipid diffusion barriers (10 nm in height and 100 nm linewidth) prefabricated onto the glass support. MDA-MB-231 cells were allowed to engage the ephrin-A1 functionalized supported membrane for 1 hr, then fixed and stained for recruitment of downstream effector molecules. (A) Irrespective of the presence or the scale of spatial mutations, phosphorylated tyrosine (pY) colocalized with ephrin-A1. F-actin adopted an annulus peripheral to the receptor-ligand assembly when EphA2 transport was unrestricted. However, when EphA2 organization was altered, the cytoskeleton assumed a spread morphology with f-actin primarily present in peripheral lamellipodia. The spread actin morphology switched to an annulus surrounding the EphA2-ephrin-A1 assembly when cells were exposed to 3 µm-pitch barriers. (B) ADAM10 colocalized with the EphA2-ephrin-A1 assembly on unrestricted supported membranes. However, when EphA2 transport was restricted by diffusion barriers, the measured colocalization decreased and the ratio of ADAM10 to EphA2 also decreased (n=477 cells). This indicates that mechanical restriction of EphA2 modulates ADAM10 recruitment.

Figure 4:
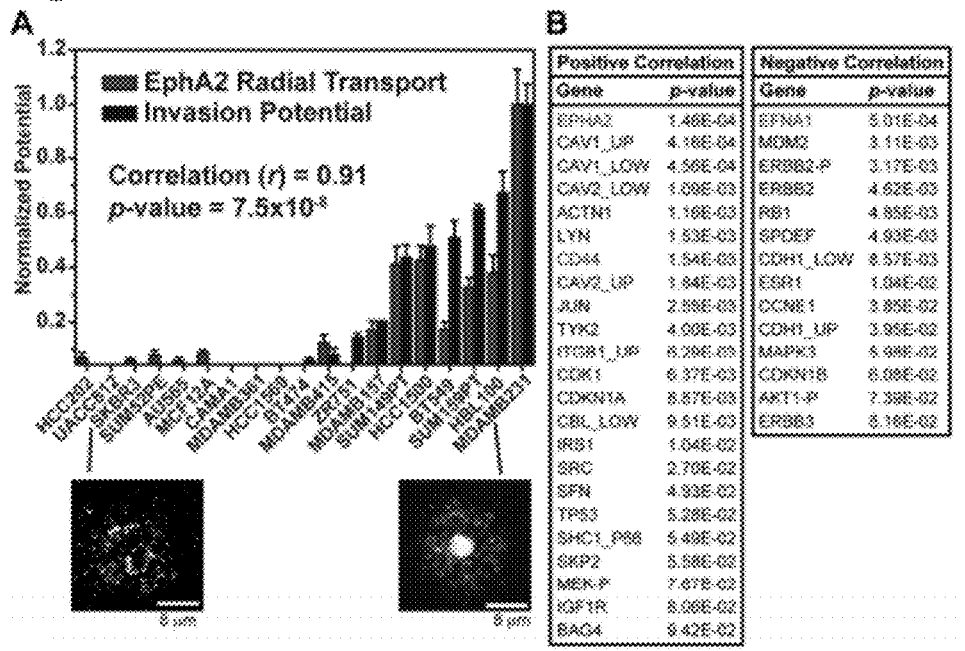

FIG. 4 depicts correlation of the CAD phenotype with proteomic and genomic expression. Correlation of EphA2 radial transport to molecular and behavior properties in breast cancer. The average ephrin-A1 ligand radial distribution functions for 26 cell lines are quantified, parameterized and then used as a spatial biomarker that is directly correlated to known biological characteristics and proteomic and genomic expression levels. (A) The average radial distribution function was found to exhibit a strong correlation (r=0.91; p-value=$7.5 \times 10^{-8}$) to invasion potentials, that were determined using modified Boyden chamber analysis. (B) The proteomic correlates (p<0.1) of EphA2 radial transport are shown in the table with their associated p-values and are grouped based on type of association (positive or negative). Proteins highlighted in red are those whose role in EphA2 reorganization has been experimentally observed. (C) Transcriptomic correlates (p<$1 \times 10^{-4}$; FDR<$5 \times 10^{-3}$) of EphA2 radial transport are illustrated in a heat map. Unsupervised hierarchical clustering of expression profiles of mRNAs that are predicted to be surrogates of EphA2 radial transport show two distinct clusters of cell lines associated with the phenotype. Red indicates upregulated expression while green indicates downregulated expression. (D) Representative bright field, epifluorescence immunostaining, and reflection interference contrast microscopy images of a cell 1 hr after plating on a supported membrane functionalized with ephrin-A1. The cell adhesion molecule CD44 was found to be significantly upregulated in protein expression in cells that underwent EphA2 radial transport. This signaling molecule was also found to be anti-localized with EphA2 upon ligand-induced activation.

Figure 5:
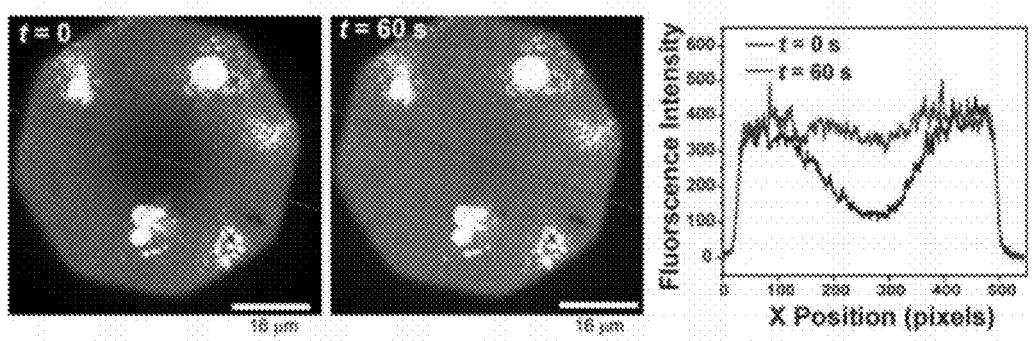

FIG. 5. Fluorescent recovery after photobleaching (FRAP) experiment performed in order to characterize the mobility of ephrin-A1 functionalized supported lipid membranes. FRAP was performed at 37° C., after live MDA-MB-231 cells (bright areas of fluorescence images) had been cultured on the surface for 1 hr. The plot on the right indicates the fluorescence intensities across an identical cross section (dotted red line) through fluorescence images before (black) and after (red) recovery. The bright areas in the image correspond to clusters formed by cells.

FIG. 6. The density of ephrin-A1 on the supported membrane surface was measured using quantitative fluorescence microscopy. (A) Texas Red-doped vesicles were used as a bulk concentration calibration standard. (B) A calibration plot indicating the fluorescence intensities of solutions containing labeled ephrin-A1 protein. (C) Texas Red-doped supported membranes were used as a surface density calibration standard. (D) The fluorescence intensities of bilayers functionalized with ephrin-A1 were fit to a re-scaled line to determine the concentration of ephrin-A1 on the bilayer surface.

Figure 7:
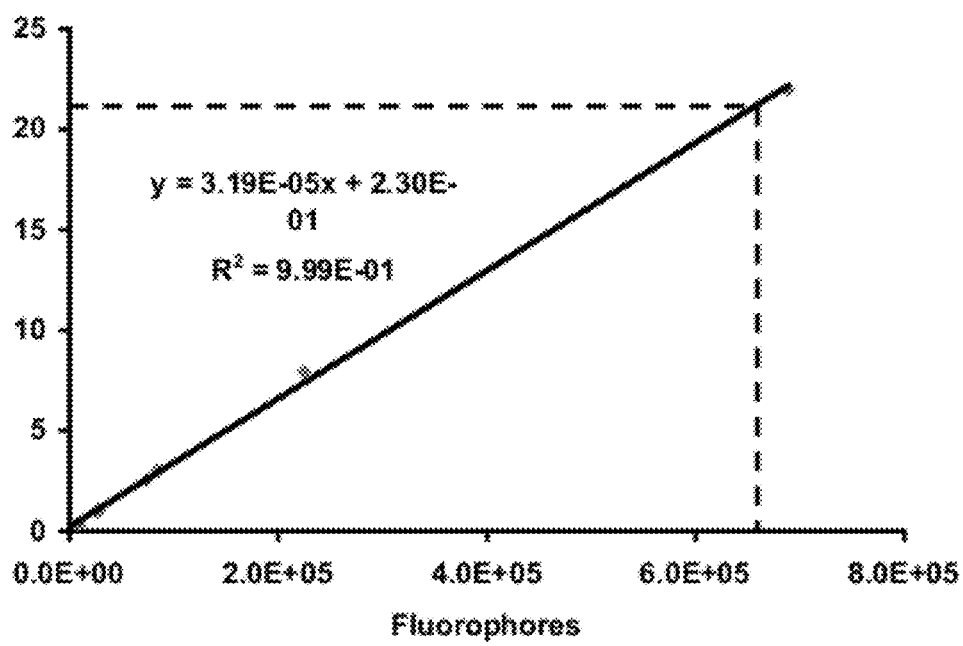

FIG. 7. Flow cytometry calibration using microparticle standards (green markers) and linear fit. Dashed lines mark the measured fluorescence intensity and calculated number of FITC-labeled EphA2 molecules on the surface of MDA-MB-231 cells. The calculated number of EphA2 molecules was divided by the labeling ratio of FITC-labeled secondary antibody and the average surface area per cell to determine the number of EphA2 molecules per $\mu m^2$.

Figure 8:
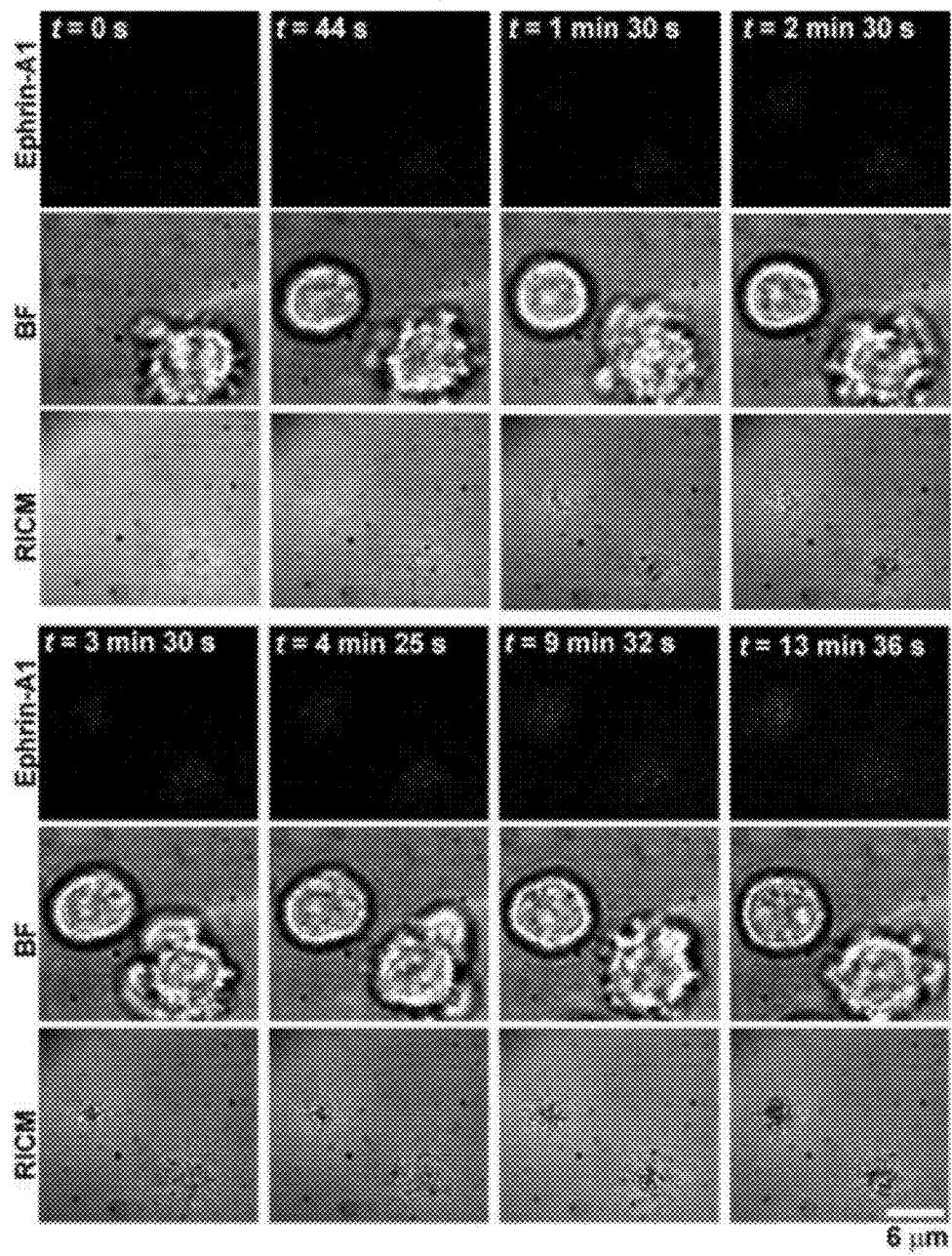

FIG. 8. Real-time fluorescence images showing ephrin-A1 transport as a function of time. The corresponding RICM and bright field images are shown for each time point. Microcluster formation begins immediately after cell contact with the supported lipid bilayer, and is accompanied with the formation of tight cell-supported membrane junctions. These clusters grow and coalesce during cell-supported membrane contact.

Figure 9:
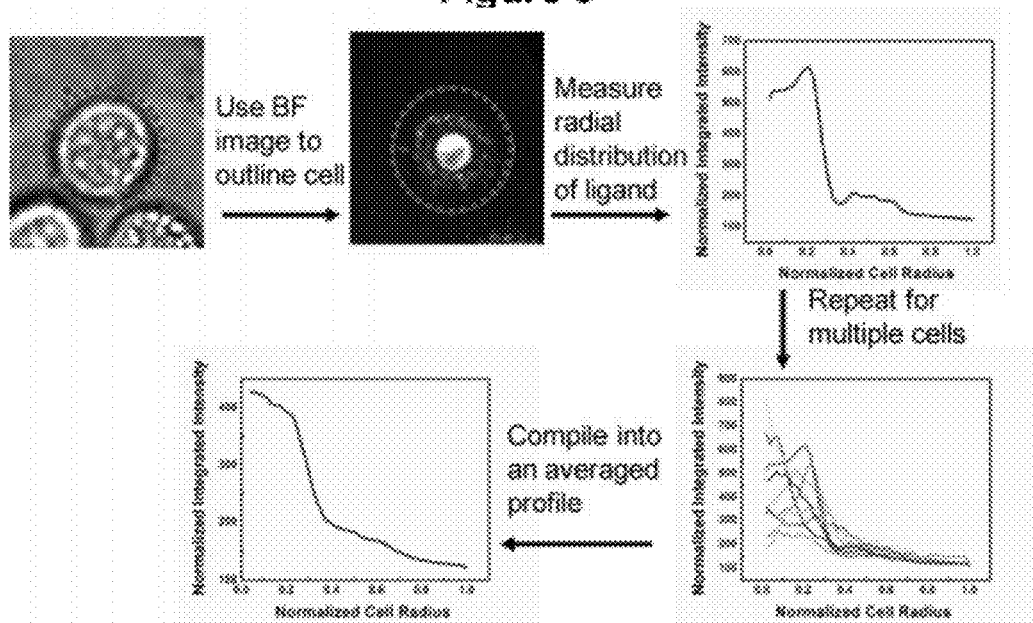

FIG. 9 shows a scheme for quantifying the radial distribution of ephrin-A1 as a result of cell-driven reorganization.

Figure 10:
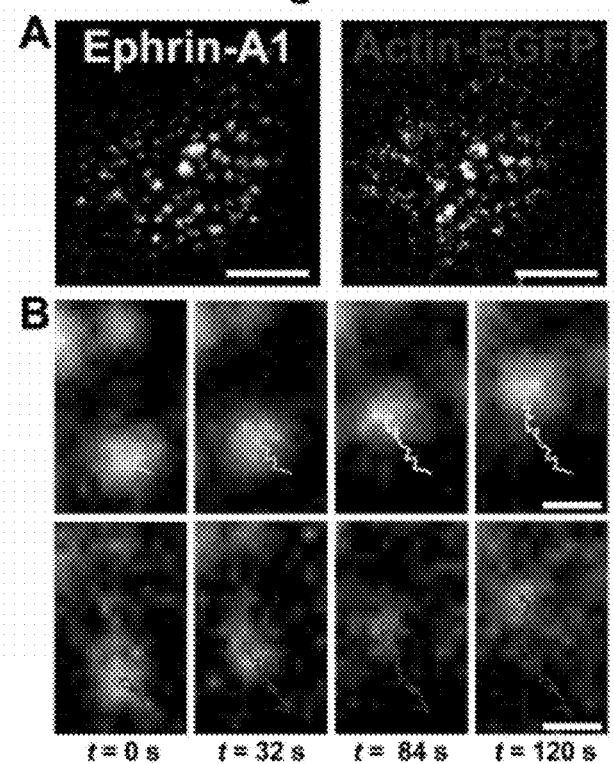

FIG. 10. Ephrin-A1 is transported with actin. (A) MDA-MB-231 cells were transfected with actin-EGFP and allowed to engage fluid supported membranes displaying ephrin-A1 labeled with Alexa Fluor 647. Scale bar is 12 µm. (B) Actin-EGFP (red) and ephrin-A1 (yellow) clusters were imaged every 4 seconds over 10 minutes. Scale bar is 2 µm.

Figure 11:
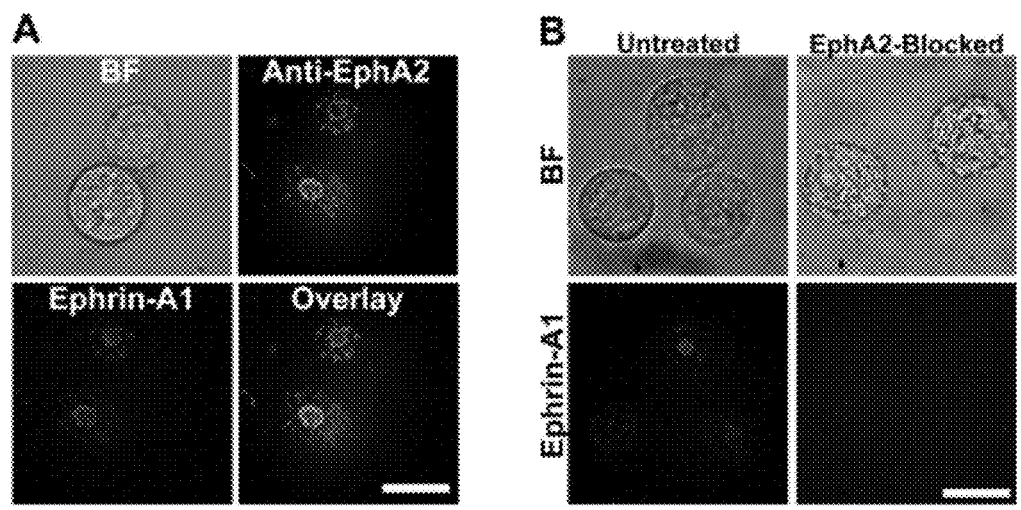

FIG. 11. EphA2 binding to ephrin-A1 leads to receptor-ligand clustering. (A) Receptor-ligand colocalization was characterized using immunofluorescence imaging. Live MDA-MB-231 cells were treated with anti-EphA2 after plating for 15 min at 37° C. on ephrin-A1-presenting supported membranes. (B) When blocking anti-EphA2 antibodies were used to treat MDA-MB-231 cells, ephrin-A1 was not clustered and cells did not adhere to supported bilayers. Scale bars are 20 µm FIG. 12. ZR-75-1 cells displaying ephrin-A1 (labeled with Hoechst 33342 nuclear stain) were cultured on a confluent layer of MDA-MB-231 cells displaying EphA2 for 1 hr. Cells were fixed and stained for ephrin-A1 and EphA2, using isotype-matched fluorescent secondary antibodies. Transport of EphA2 and ephrin-A1 to the cell-cell interface was observed.

Figure 13:
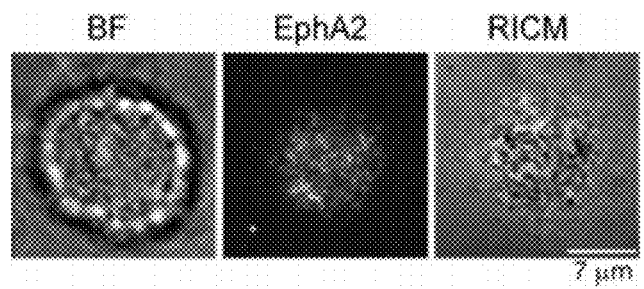

FIG. 13. When ZR-75-1 cells expressing ephrin-A1 were cultured on a supported membrane functionalized with the extracellular domain of EphA2, they formed microclusters of EphA2, but did not radially transport EphA2-ephrin-A1 complexes.

Figure 14:
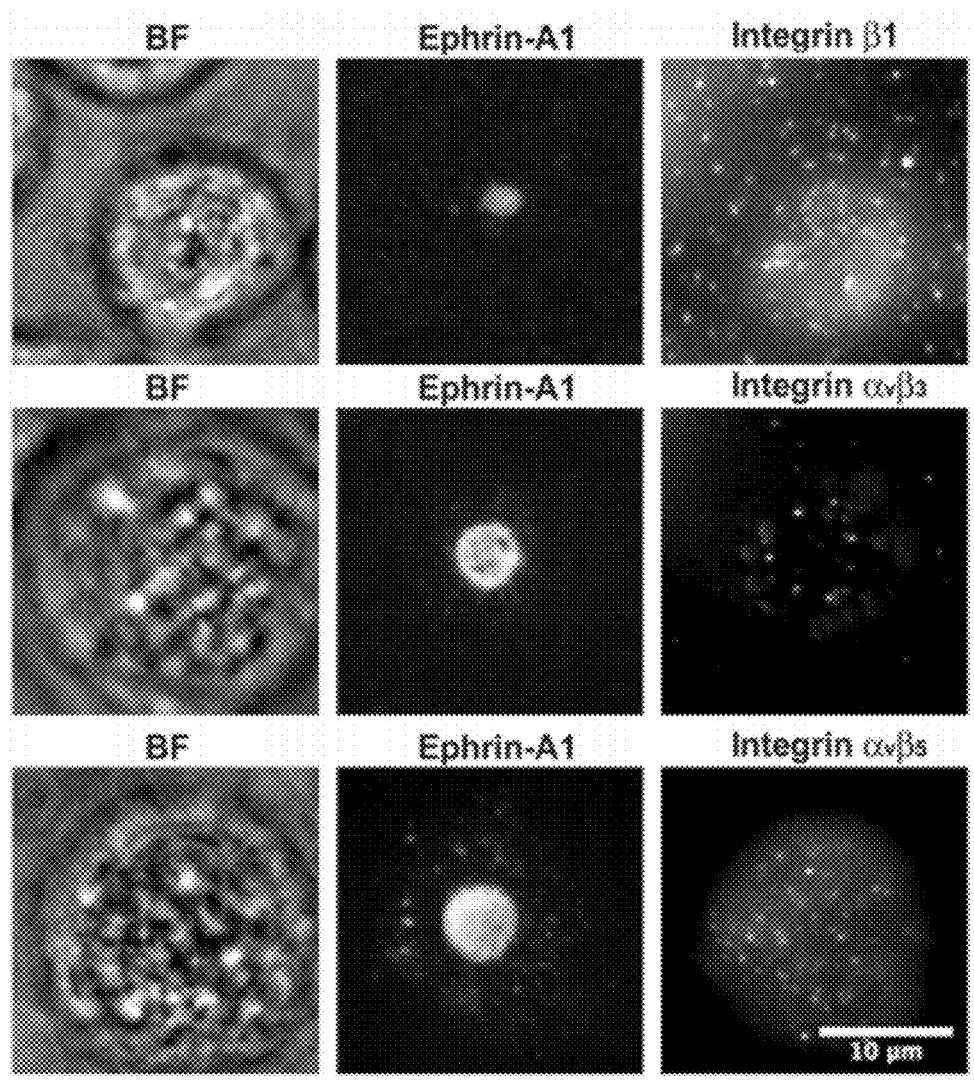

FIG. 14. Integrins $\beta_1$, $\alpha_v\beta_3$, and $\alpha_v\beta_5$ all show no significant colocalization with ephrin-A 1.

Figure 15:
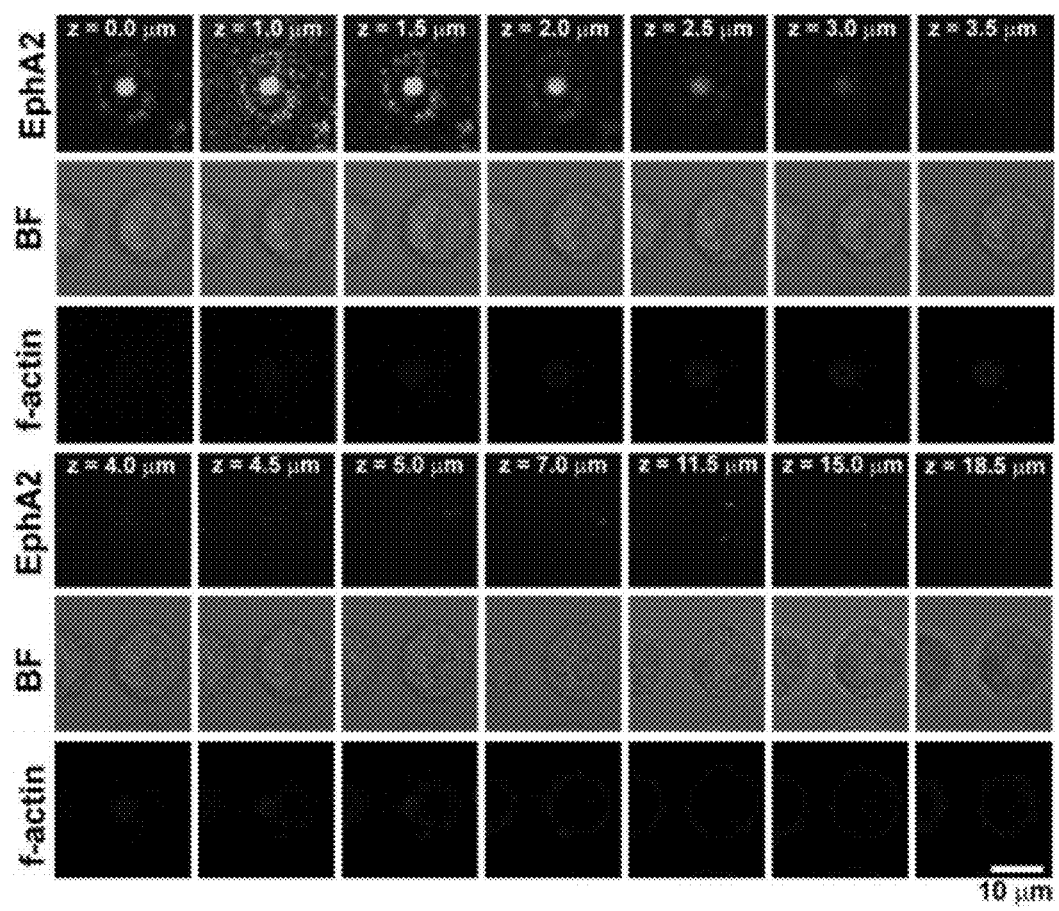

FIG. 15. 3D structure of EphA2 and f-actin in MDA-MB-231 cell after 1 hr of contact with a fluid supported membrane displaying ephrin-A1. Z-stack of confocal images. EphA2 was visualized using immunofluorescence and f-actin was visualized using Alexa Fluor 350-conjugated phalloidin. Z-axis step size is 0.5 µm.

Figure 16:
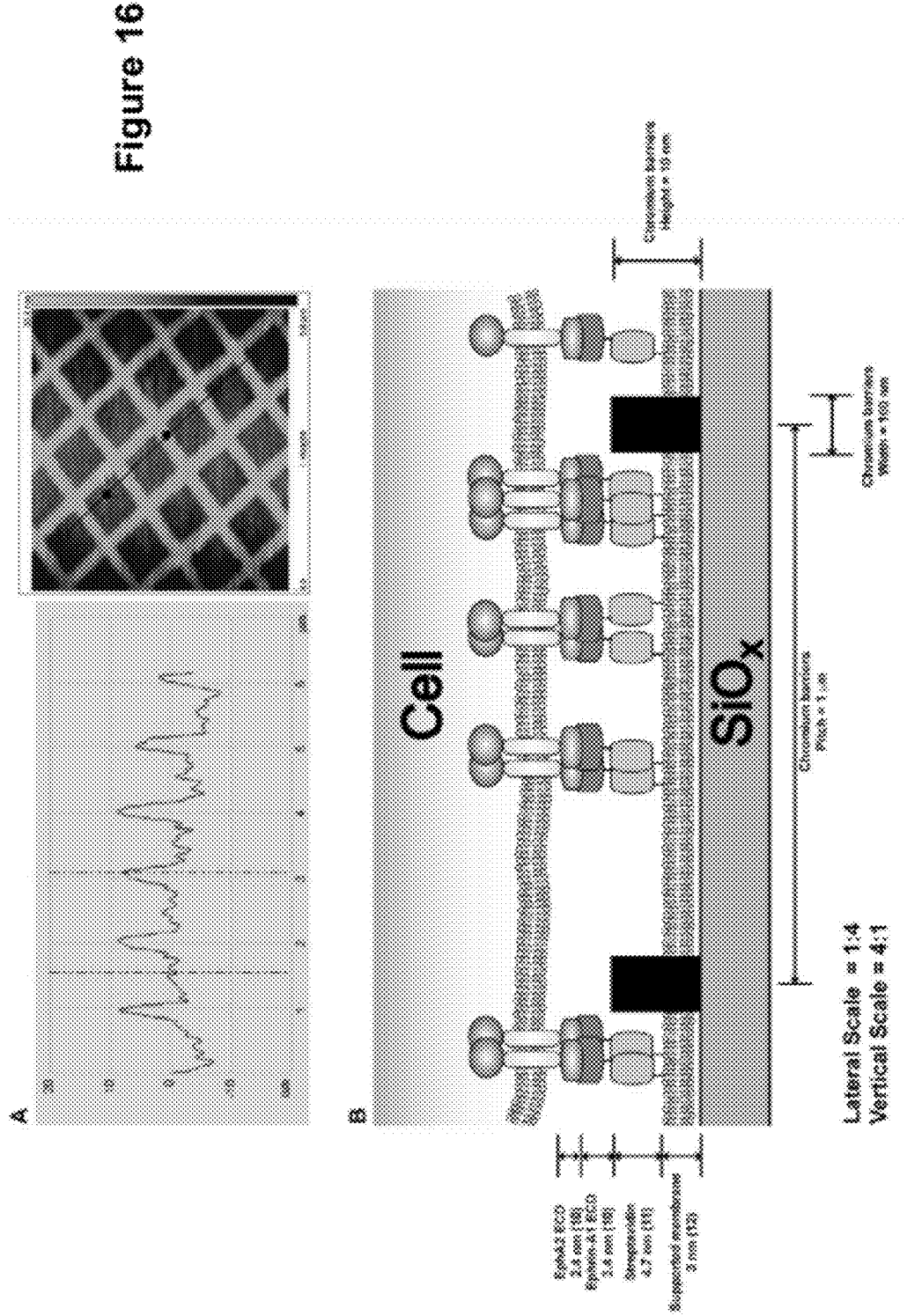

FIG. 16. The patterned chromium barriers do not alter the topography of the functionalized supported membrane surface. (A) An atomic force microscopy (AFM) image and corresponding line scan of chromium grids with a 1 μm pitch showing barrier heights of approximately 10 nm Filled circles on AFM image denote points corresponding to dashed lines on line scan. (B) Schematic diagram of cell-supported membrane interface drawn to scale. References for protein and membrane dimensions are shown in parentheses.

Figure 17:
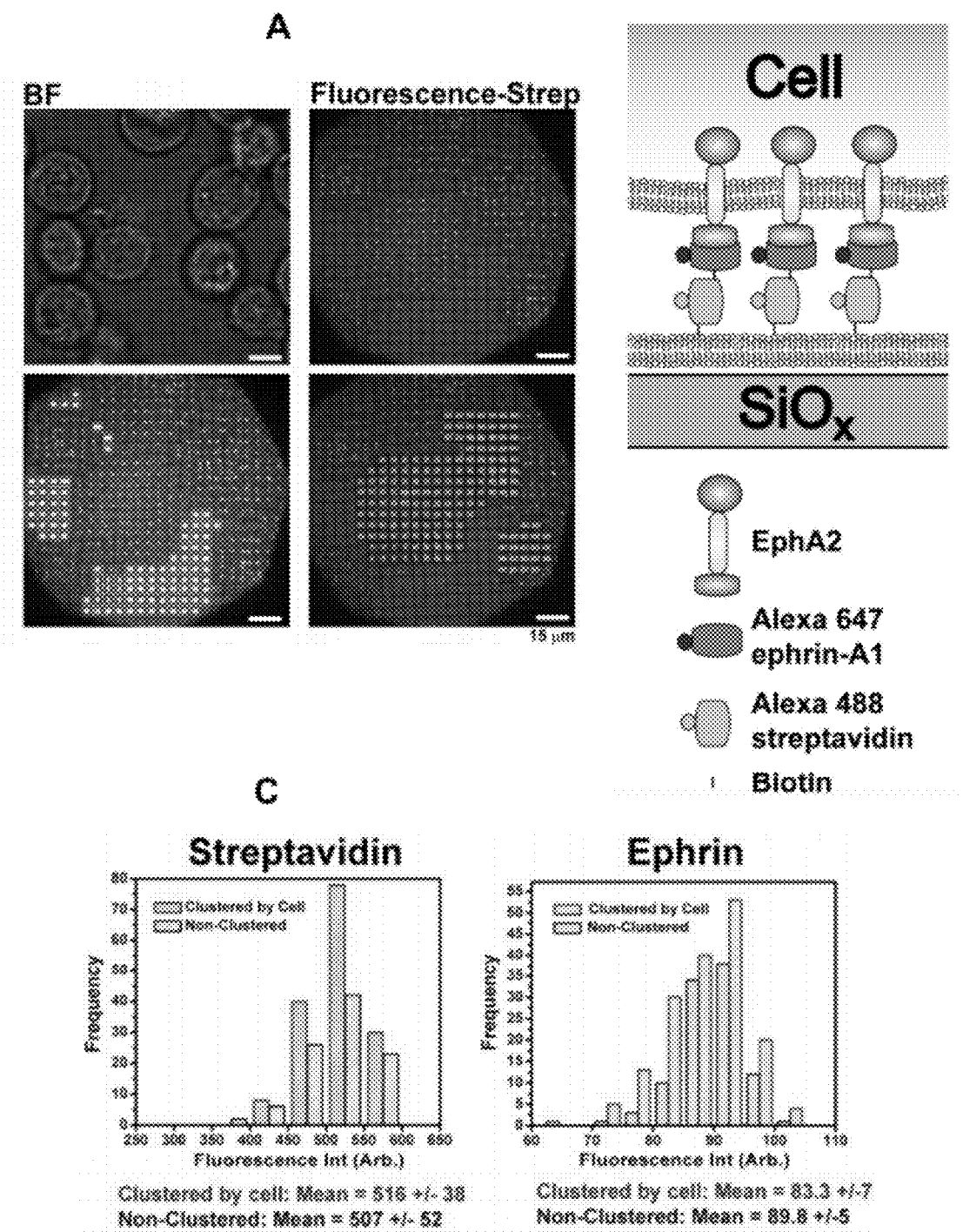

FIG. 17. Cell-driven ephrin-A1 clustering does not change the integrated fluorescence intensity measured from each nanopatterned box. Fluorescently-labeled ephrin-A1 and streptavidin were both used to functionalize a supported membrane. Cells were allowed to engage the surface for 1 hr, and then the fluorescence intensity was measured and integrated for each Cr-grid defined box. Histograms of integrated measurements are shown (lower) and indicate that the intensities from all boxes are within experimental error.

FIG. 18. Protein localization to EphA2 central assembly is highly specific. Immunofluorescence was used to probe the colocalization of pY and HCAM to EphA2 central assembly. Cyclic-RGD functionalized supported membranes were used as a control promoting cell adhesion. (A) The central assembly of EphA2-ephrin-A1 is highly phosphorylated. (B) CD44 anti-localizes with the ephrin-A1 central assembly.

FIG. 19. EphA2 association with ADAM10 as a function of time. Ephrin-A1 stimulated cells were fixed and stained for ADAM10 and for EphA2 using primary and secondary antibodies. At early time points, the fluorescence intensities of both ADAM10 and EphA2 were very low. However as ligand stimulation proceeds, both the amount of ADAM10 recruited to the interface and the degree of ADAM10 localization to EphA2 (as measured by Pearson's correlation values±SE), increased.

FIG. 20. Selective recruitment of ADAM10 to central assemblies of Eph-ephrin complex is independent of RGD-mediated flattening of the cell-supported membrane interface and subsequent signaling.

Figure 21A:
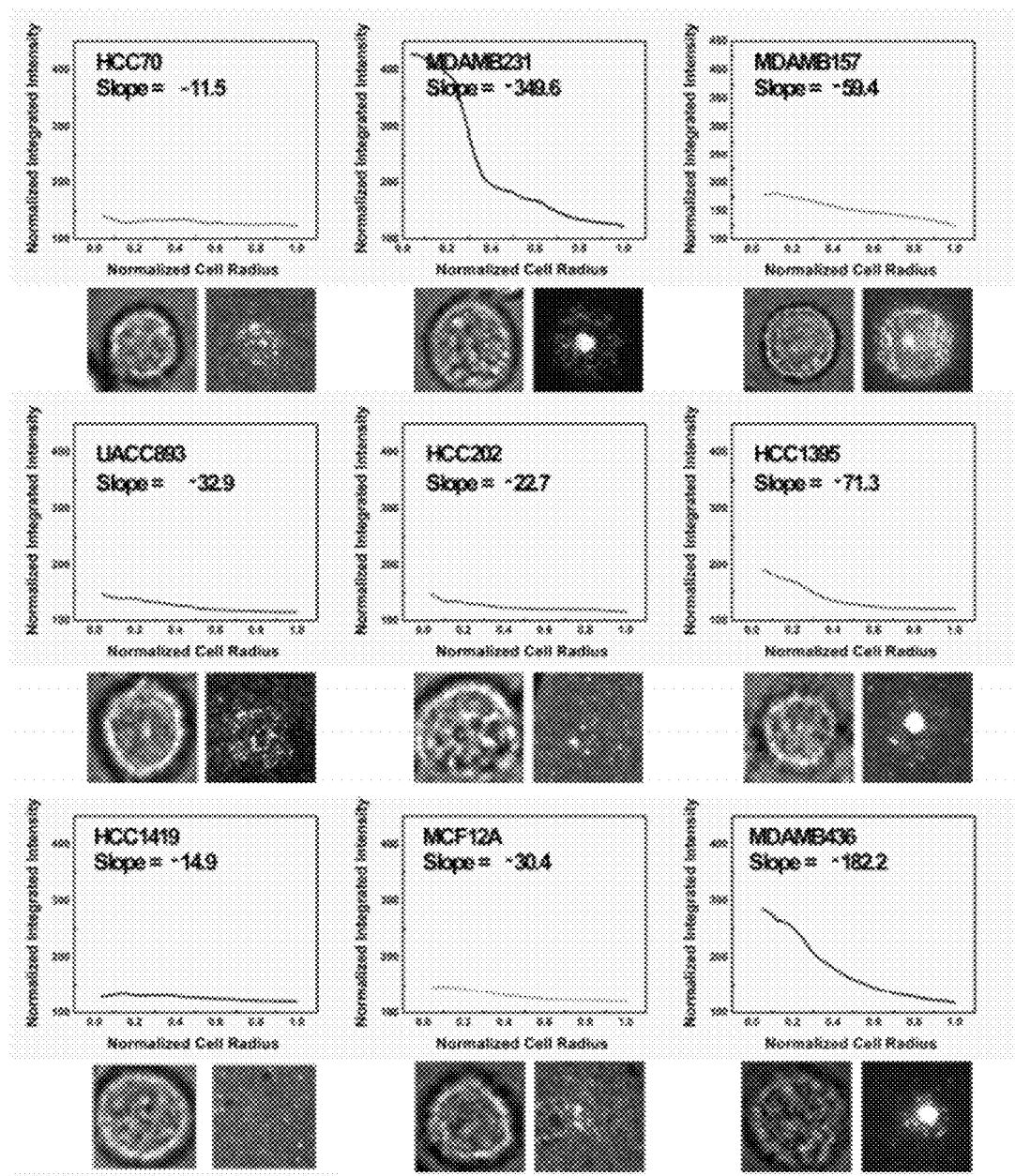
Figure 21B:
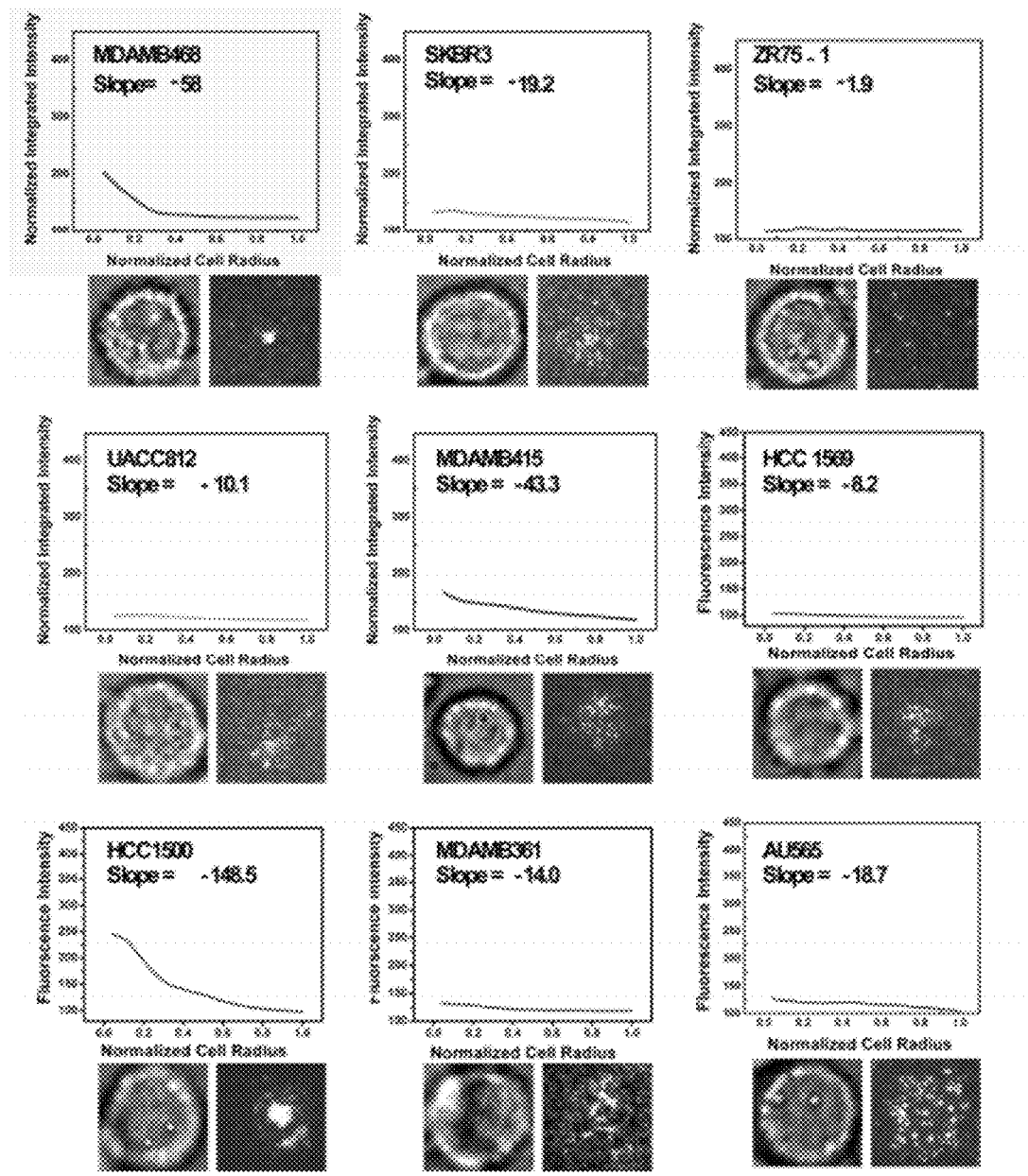
Figure 21C:
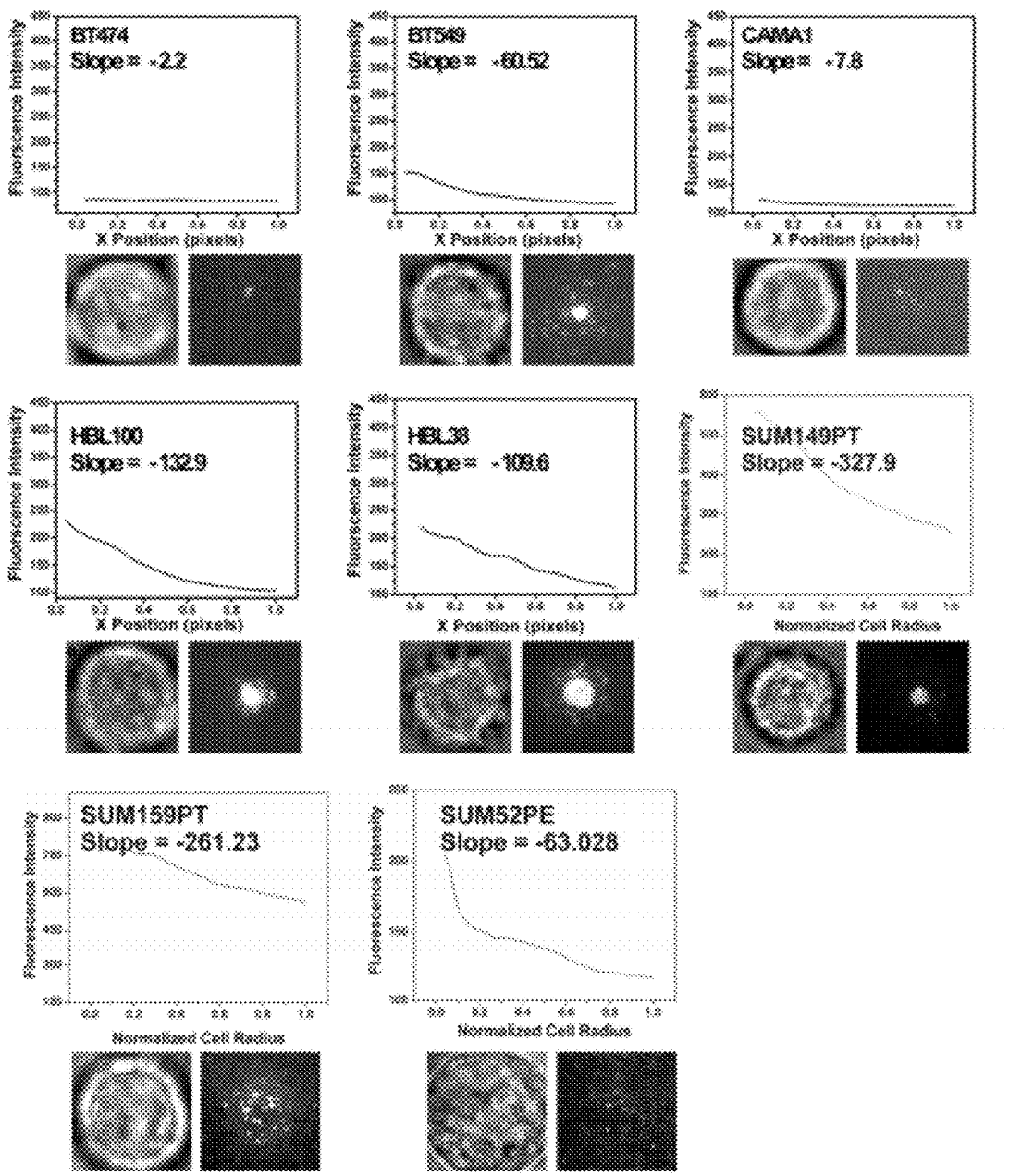

FIG. 21A-C. Radial distributions and representative fluorescence images of cells from each cell line that were allowed to engage ephrin-A1-functionalized supported membranes for 1 hr.

Figure 22:
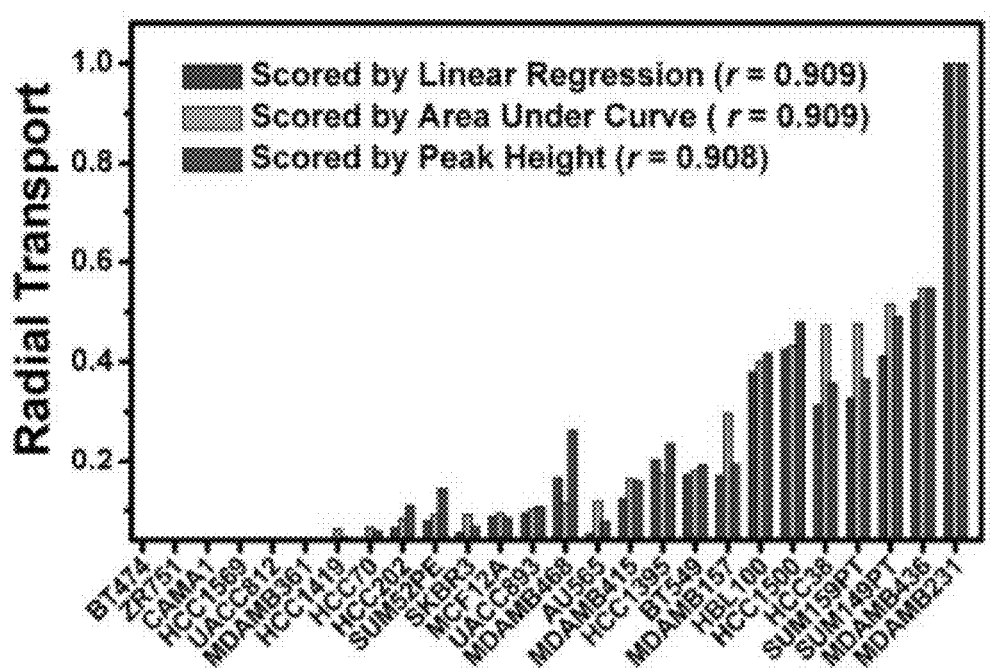

FIG. 22. Normalized radial transport scores for 26 unique breast cancer cell lines.

Table 1. 141 mRNA transcripts (158 probesets) displayed significant correlation ($p<1\times10^{-4}$, $FDR<5\times10^{-3}$) with EphA2 radial transport phenotype. Their respective correlations with invasion potential are also shown. All selected mRNA biomarkers display the same type of correlation with the EphA2 reorganization phenotype as with invasion potential.

Table 2. 37 proteins displayed significant correlation ($p<0.1$) with EphA2 radial transport phenotype. Their respective correlations with invasion potential are also shown. All selected protein biomarkers display the same type of correlation with the EphA2 reorganization phenotype as with invasion potential.

Table 3. 15 KEGG pathways displayed significant correlation ($FDR<5\%$) with EphA2 radial transport phenotype.

Table 4. 13 Biocarta pathways displayed significant correlation ($FDR<5\%$) with EphA2 radial transport phenotype.

DETAILED DESCRIPTION

In one embodiment, an assay comprising: a live cell having a plurality of receptor or cell-surface molecules or proteins on the cell surface, the receptors or cell-surface molecules capable of binding a ligand. The assay comprising a physical context adapted to facilitate ligand binding and distribution on the cell surface of the cell surface molecules or receptors upon binding with the ligand. After introducing the ligand to the cell and allowing the cell surface molecules or receptors to interact and bind to form a receptor-ligand or ligand-cell surface molecule binding complexes. Once receptor activation occurs, these binding complexes redistribute or cluster on the cell surface in a reproducible or predictable pattern. Thus, receptor activation can be detected as a reorganization or redistribution "signature" as manifested by clusters of ligand-receptor binding pairs on a live cell and such signature pattern of distribution of bound molecules on the surface of the cell can be correlated to a specific state or indication of a single cell.

The assay of the invention can be conducted in a physical context that allows the live cell to remain intact, and the ligand to remain accessible to the receptor on the surface of the cell. Furthermore, the physical context should be adapted to allow the receptor to respond to the ligand. This may mean that the cell-surface molecule will form an activation complex with the molecule, or molecules (and multiple receptors may be involved in a single activation complex), and it may mean that the receptor (and so the activation complex) will relocate on the cell surface.

In some embodiments, the assay comprising: a live cell derived from a source having a condition, the live cell having a plurality of a receptors on a cell surface, the receptor capable of binding a ligand, the assay including a physical context adapted to facilitate ligand binding and distribution on the cell surface of a bound receptor, wherein a pattern of receptors distributed on the surface of the cell comprises a signature for the condition.

The cell used in the assay is a preferably a live cell, whereby the cell is able to respond to stimuli with native-like responses that include changes in transcription, translation, expression, appearance of the cell, and component organization within the cell. Most importantly for the purposes of using a live cell in the current assay, the live cell needs to be responsive to activation through an interaction of external stimuli with the cell-surface molecule expressed on the cell. Confirmation that the receptor distribution on the cell surface is made by detecting one or more transcriptional events "downstream" after receptor redistribution, such as genes that form a genetic profile for the condition.

The physical context of the assay, e.g., the assay conditions and platform of the assay, allows a binding ligand residing external to the live cell, to bind a cell-surface molecule, e.g., a receptor or ligand, present on the surface of the live cell. Although the events that follow can include any number of binding and activation events, typically a complex of several bound molecules, e.g., receptors bound to ligands, is formed on the cell surface. The complex is identified by the assay as an activation complex. Cell activation can be confirmed by detection of "downstream" gene expression of genes as a result of the ligand binding the receptor.

The activation complex may do a number of things after forming. In one embodiment, the assay captures the activities of the cell-surface molecule, and uses the changes of location of the receptor on the cell surface as a readout or signature that can be correlated to the condition of the tissue from which the cell was derived. The ligand may be a cell surface molecule also, and as such is able to bind the cell surface receptor on the target cell.

In one embodiment, the assay is conducted in an environment that functions for combining the soluble lipid bilayer with an attached labeled ligand, where the labeled ligand will specifically bind a receptor or cell-surface molecule present on a live cell to form an activation or binding complex. Possible environments can be any environment that allows the receptor on the cell to contact the ligand on a substrate or in a solution, and which will allows detection of the binding or activation complex, and identification of the downstream signaling molecules on the cell.

In some embodiments, environments for the assay can include a solid substrate like a microplate or bead, a liquid environment such as a solution, a vessel such as a tube the inner surface of which can be a substrate, and other configurations. In another embodiment, a microplate having a plurality of nanobarriers that act as diffusion barriers for receptor-ligand complexes is used. Detection of labeled ligands at nanobarriers on the microplate indicates active receptor transport. The nanobarriers can be a grid as shown in FIGS. 3, 16 and 17.

In another embodiment, a supported lipid bilayer is used for presenting the ligand to the live cell. In one embodiment, the assay employs a supported lipid bilayer (SLB) to direct live cells to display nanopatterns at artificial membrane synapses. In one embodiment, the present invention provides a hybrid live cell soluble lipid bilayer (SLB) assay for identifying cell-surface receptor activation comprising a synthetic fluid membrane lipid bilayer. The lipid bilayer comprises a labeled cell-surface ligand capable of binding and activating the cell-surface receptor. The receptor activation is detected as a reorganization or redistribution "signature" that is manifested in clusters of ligand-receptor binding pairs on the live cell. For example, in a specific example of breast cancer the EphA2 receptor and its ligand can form clusters on the surface of breast cancer cells. The assay will typically include the live cell of interest (e.g. a diseased cell) expressing a cell-surface receptor.

In another embodiment, the substrate is a microplate having a plurality of nanobarriers that act as diffusion barriers for receptor-ligand complexes is used. Detection of labeled ligands at nanobarriers on the microplate indicates active receptor transport. Use of nanobarriers on microplates to create nanopatterns was a technique designed into a SLB assay as a tool to investigate and manipulate T-cell receptor (TCR) signaling at the immunological synapse (See e.g. U.S. patent application Ser. No. 12/151,553; and K. D. Mossman, G. Campi, J. T. Groves, M. L. Dustin, *Science* 310, 1191 (November, 2005), both hereby incorporated by reference in their entireties). The SLB nanopattern forming assays achieved both native and non-native synaptic configurations. In addition, for this biological pathway, nanopattern formation was found to be directly caused by downstream signals that were detected in the assays.

Co-pending parent U.S. patent application Ser. No. 12/151,553, filed on Jul. 21, 2008, entitled, "A Fluid Membrane-Based Ligand Display System for Live Cell Assays and Disease Diagnosis Applications," hereby incorporated by reference in its entirety, discloses detection of cell phenotypes in an SLB assay using soluble signaling ligands attached to the lipid bilayers. Other SLB assays are described in U.S. Pat. No. 6,228,326, which is incorporated by reference in its entirety. Co-pending U.S. patent application Ser. No. 10/076,727, incorporated by reference in its entirety, describes use of SLB assays to effect and modulate cell adhesion. All these related publications and patent applications are incorporated by reference in their entirety, especially for the purposes of enabling and exemplifying aspects of the present invention that had been developed in previous work conducted by some of the same inventors.

Various supported membranes can be made that display the various cell surface signals encountered in normal tissue. Similarly, a plurality of various supported membranes can be made that display the various cell surface signals from cell lines of a type of cancer, or various cancers, etc. Biopsy cells from an individual patient or a population of patients are cultured on this artificial cell surface, and their behavior under the influence of various drugs is examined Key to this strategy is the ability to functionally reconstitute the appropriate cell surface signals so that critical behaviors, such as invasion, are accurately revealed. Others have shown that different environments such as 3-D cell culture systems drive cells to behave in completely different ways comparing to typical 2-D cell culture environments. This becomes critical when one needs to replicate in vivo experimental results on a bench top.

The naturally fluid state of the supported membrane, which allows surface-linked ligands to diffuse freely in two dimensions, allows ligands to become reorganized beneath cells, by reaction-diffusion processes, and can reflect spatial configurations of the cognate receptors on the cell surface.

The substrate of the assay system preferably comprises any material with a lipid-compatible surface such as $SiO_2$, $MgF_2$, $CaF_2$, mica, polydimethyl siloxane (PDMS), or dextran. $SiO_2$ is a particularly effective substrate material, and is readily available in the form of glass, quartz, fused silica, or oxidized silicon wafers. These surfaces can be readily created on a variety of substrates, and patterned using a wide range of micro- and nano-fabrication processes including: photolithography, micro-contact printing, and electron beam lithography, scanning probe lithography, optical phase-shift lithography and traditional material deposition and etching techniques. Detection of these surfaces can be accomplished by typical biochemical and electrochemical detection processes known in the art.

The array format, having barrier materials, provides separate compartments in the array for quantification purposes. Bilayer barrier materials can include polymers, such as photoresist, metals, such as chrome and gold, and minerals such as aluminum oxide. Alternatively, effective barriers between membrane corrals can be achieved by leaving portions of the substrate free of membrane. The resulting gap serves as a barrier that prevents diffusive mixing between separate corrals.

The supported bilayer of the assay system comprises a lipid bilayer. In one embodiment, the primary ingredient of the lipid bilayer is a dioleoylphosphatidylcholine (PC) membrane. In the absence of dopants, cells do not adhere to this membrane. Other suitable lipids that do not permit cell adhesion include pure phosphatidylcholine membranes such as dimyristoyl-phosphatidylcholine or dipalmitoylphosphatidylcholine. Another suitable primary lipid component is phosphatidylethanolamine (PE), which is also, in addition to PC, a primary component.

The lipid composition in the supported lipid bilayer can comprise dopants to vary bilayer properties. Preferred dopant lipids are a negatively, positively or neutrally charged lipid. In one embodiment, the dopant lipid is the negatively charged lipid phosphatidylserine (PS). Other potential dopants can be dipalmitoylphosphatidic acid (PA), distearoyl-phosphatidylglycerol (PG), phosphatidylinositol,1,2-dioleoyl-3-dimethylamonnium-propane, 1,2 dioleoyl-3-trimethylammonium-propane (DAP), dimethyldioctadecylammonium bromide (DDAB), 1,2-dioleoyl-sn-glycero-3-ethylphosphocholine (ethyl-PC), N-(7-nitrobenz- 2-oxa-1,3-diazol-4-yl)-1,2-dihexadecanoyl-sn-glycero-3-phosphoethanolamine ammonium salt (NDB-PE). Suitable neutral lipid dopants include cerebrosides and ceramides. The amount of the dopant is selected based on the property of the dopant. For a lipid dopant 2 to 20% is preferred.

The planar supported bilayers are formed by fusion of small unilamellar vesicles (SUV) with clean silica substrates according to the methods described in Salafsky, J., J. T. Groves, and S. G. Boxer, Architecture and function of membrane phospholipids in erythrocytes as factor in adherence to endothelial cells in proteins, *Biochemistry*, 1996, 35: 14773-14781, and U.S. Pat. No. 6,228,326, both of which are hereby incorporated in their entirety.

Generally, a lipid solution in chloroform is evaporated onto the walls of a round bottom flask that is dried under nitrogen. Lipids are resuspended in distilled water by vortexing moderately for several minutes. The lipid concentration at this point should be around 2-4 mg/ml. The lipid dispersion is then extruded through 100 nm-sized pore filters, yielding small unilamellar vesicles (SUV). SUVs are stored at 4° C. and typically are stable for a few weeks to several months. The SUVs are fused onto the aqueous phase on the substrate. The vesicles spontaneously assemble in a matter of seconds to form a continuous single bilayer on the substrate. Excess vesicles are rinsed away while maintaining the membrane bilayer under bulk aqueous solution at all times. The ligand for the SLB assay can be a membrane-anchored signaling ligand attached to both an affinity tag with a known binding partner and a detectable label.

The ligands or test ligands can include any ligand, e.g. proteins, antibodies, peptides, nucleic acids, small molecules, drugs, carbohydrates, and any molecule capable of binding the receptor on the cell. Typically, in vivo, such a ligand will be presented to the cell expressing the receptor in a cell membrane of a neighboring cell. The ligand can be a test drug.

A lipid bilayer works well in the assay because it can mimic the flexibility and availability that the molecule would otherwise have if presented on the membrane of a different cell, e.g. on the surface of a partnering cell, or in a complex of several ligands or chemical actors. The lipid bilayer works well also because the optically detectable means can be read from a microscope adjusted to just the correct plane of view on a side of the cell that is held under glass. Other presentation means (in other physical contexts) could include a solution which would require optically detecting a redistributed receptor on the cell surface where the microscope or other reader is adjusted to receive information from the cell in 360 degrees, or in a defined field of view, or by a specified cross-section of the solution, for example.

In some embodiments, a cell-surface ligand is presented on the substrate. The ligand is adapted to form a complex with a cell-surface receptor of a live cell (i.e., a binding pair with a one-to-one binding ratio, or a complex where more than two binding molecules are involved). The live cell is introduced to the ligand, and the available ligands and receptors form binding pairs or complexes of binding molecules. The complexes comprising at least the receptor and ligand binding interaction. The resulting distribution pattern of the complexes comprises a signature for that cell. In one embodiment, the distribution pattern can be combined with the intensity of the label that tracks the receptor.

The distribution of the receptor should be detectable in the assay. In order to gather useful information across populations of cells, patients, and drugs, tissues, and conditions, the "activation" has been quantified. For example, in the exemplary case of a live cell having a receptor that binds a ligand or multiple ligands, and relocates in activation complexes that form clusters on the cell surface, optical intensity of the clustered cell-surface molecules is measured. Activation, in this example, is therefore measured by the optical density of receptors on the cell surface. A region of the cell surface is identified for the purpose of quantifying activation in the assay, and is some portion of the cell surface that amounts to less than the whole cell surface. So, for example, where a whole cell is typically 10 microns across when flattened under glass, the portion of that area used for quantification of cell-surface mediated cell activation is any portion size from about 1 nanometer to about 10 microns, and all sub-portion sizes in between that distance span. Generally, an assay protocol will select a portion size for the quantification and detection receptor distribution that remains consistent, such as an approximate 5 nm span, or a sphere of about 100 nm. Critical to effective optical detection in this exemplary scenario, is that the optical detection means (e.g. a microscope or other viewer and magnifier) can be positioned to receive visual information in the field of view of the cell surface where the clusters of activation complexes comprising the ligands and receptors are expected to be. Also a critical pre-event to the data collection, is gathering baseline (control) measurements of receptors (quantity and location) before activation.

Detection of receptor relocation can be accomplished by any suitable means, for example by fluoroscopy using a microscope to detect fluoroscopically labeled receptors and other entities. Other microscope based detection systems may also be adapted to the experiments to view labeled receptor relocation, e.g. including electron microscopy, transmission electron microscopy, and scanning electron microscopy.

In another embodiment, a signature is identified and devised from quantifying receptor distribution on a cell surface after binding a ligand. A "signature" as used herein is a pattern of receptor distribution on the surface of a cell. In one embodiment, the assay using live cells or cells from biopsies or other tissue samples of patients.

Thus in one embodiment, the invention provides an assay and method for establishing a signature for a cell by detecting complexes of at least one receptor-ligand binding interaction in a particular (characteristic) distribution pattern on the live cell surface. The signature or distribution pattern minimally indicates receptor activation. In another embodiment, the signature detected provides an identifier of the state or condition of the cell. For example each type of diseased cell may have a different signature in the assay. Also, by example, different stages of the same disease may have different signatures. Accordingly, live cells derived from different cancers should exhibit different signatures, and live cells derived from different stages of cancer of the same type will exhibit different signatures in these assays.

The ligand distribution or signature can be detected any number of ways, but most conveniently the distribution is detected optically, by a visual means such as a microscope. This requires both that a label is attached on the receptor (or attached to a molecule that is attached to the receptor) and that the label is detectable.

Methods of labeling molecules are well known to those of skill in the art. Preferred labels are those that are suitable for use in in situ hybridization or binding reactions. The ligand-chimera may be detectably labeled prior to the hybridization or binding reaction. Alternatively, a detectable label which binds to the hybridization product may be used. Such detectable labels include any material having a detectable physical or chemical property and have been well-developed in the field of immunoassays.

As used herein, a "label" is any composition detectable by spectroscopic, photochemical, biochemical, immunochemical, or chemical means. Useful labels in the present invention include radioactive labels (e.g., $^{32}$P, $^{125}$I, $^{14}$C, $^{3}$H, and $^{35}$S), fluorescent dyes (e.g. fluorescein, rhodamine, Texas Red, etc.), electron-dense reagents (e.g. gold), enzymes (as commonly used in an ELISA), colorimetric labels (e.g. colloidal gold), magnetic labels (e.g. Dynabeads™), and the like. Examples of labels which are not directly detected but are detected through the use of directly detectable label include biotin and dioxigenin as well as haptens and proteins for which labeled antisera or monoclonal antibodies are available. The particular label used is not critical to the present invention, so long as it does not interfere with the in situ hybridization of the stain. In one embodiment, the detectable label is a fluorescent label. In a specific embodiment, Alexa Fluor 647, NBD and Hoechst 33342 are preferred for use with the supported bilayer assay system.

In addition to detection of labeled molecules and clusters to determine a signature for a cell, the invention provides a mechanism to quantify the signature by quantifying the receptor redistribution on the cell surface. Quantification of the signature can be made by detecting an intensity of label that tracks the receptor to a pre-determined region on the cell surface.

Quantification of normalized radial transport scores can be calculated through various means as is known in the art such as by linear regression, area under the curve, peak height, etc. FIG. 9 shows a scheme whereby the radial distribution of cells can be quantified. Quantifying the radial distribution of ephrin-A1 as a result of cell-driven reorganization. The outline of each cell was defined using the bright field image of each cell. The radial distribution of fluorescence intensity was then measured for each cell using software analysis package ImageJ. The radial distributions are then normalized for the cell radius to account for differences in cell size, and then averaged for each unique cell line to generate a signature average radial distribution function. FIG. 22 shows a bar graph of quantification of normalized radial transport scores for 26 unique breast cancer cell lines and FIG. 21 A-C shows the radial distributions determined for each of the breast cancer cell lines.

Both the pattern of the receptor redistribution (the signature) and the quantification of the receptor activation (the radial transport or cell activation score) can be used together to provide a live-cell-assay-derived classification or index for the condition from which the cell came. In turn that information can be used for such downstream events or uses as diagnosis, prognosis and screening for efficacious drugs to treat the condition. Thus the invention can be used to compare signatures in cells for various cell types and various conditions, and accordingly be used for developing diagnostic and prognostic assays for a particular disease, and also for screening for drugs to treat the disease. For example, likely candidate therapeutic molecules can be screened for an ability to specifically target and modulate (i.e. inhibit or attenuate or enhance) receptor activation and the downstream effects of that activation—activation of the cell. The test drug can bind the receptor, or inhibit binding of the receptor and ligand, or inhibit clustering of the activation complex once formed.

In another embodiment, a useful research tool for analyzing a multitude of cell types and tissue conditions, against any number of ligands. Information that can be yielded from the assay includes differentiation of activation pathways, and other useful research objectives. Quantification of receptor activation by quantifying the distribution of receptors (by label intensity) that redistribute to a pre-defined region on the cell surface also provides a score for cell activation. Combined with an optically detected signature correlated to the condition of the tissue, the assay can be applied to diagnosis, prognosis, and drug screening, which relate directly to patient care.

A suite of hybrid live cell assays can be created that comprehensively reconstitute numerous functional aspects of a particular cancer. Interactions between live cells from the patient with cell surface signals (e.g. displayed on a supported membrane) can create a personalized assay, with which potential therapeutic agents can be characterized. This type of micro high throughput live cell assay can form an integral part of a comprehensive diagnostic process, which would also involve extensive genetic and protein expression profiling.

An assay as described above can be used to analyze a collection of more than 60 human breast cancer cell lines in which protein expression profiling is significantly diverse. A set of behavior responses to a specific supported membrane comprising displayed signals is established, and drug effects on the control behavior can be studied in the assays and using the methods of the invention. Efficacy in the assay serves to predict therapeutic value of a given test drug. A set of live cell assays for cancer drug discovery is a useful tool for drug discovery. Development of small scale assays for diagnostic applications on patient biopsy samples can be followed by development of larger scale assays to address the entire population of patients in a group defined by a specific cancer condition.

For example, FIG. 1 depicts EphA2 receptor activation achieved through a supported lipid membrane functionalized with the extracellular domain of the ephrin-A1 ligand using a biotin-streptavidin anchor. See J. M. Nam, P. M. Nair, R. M. Neve, J. W. Gray, J. T. Groves, *Chembiochem* 7, 436 (March, 2006) and Example 1 below for a detailed description of how to functionalize the extracellular domain of this ligand on a supported lipid membrane using a biotin-streptavidin anchor). The biological interface of the membrane is fluid in two-dimensions and thus achieves in an in vitro environment the contact-dependent signaling activity that occurs when two cells make contact in vivo. Nano-patterns are directed by design in the assay to represent in an in vitro system the introduction of redistribution in the native receptor-ligand spatial organization (see also FIG. 1). A physiologically accurate form of receptor redistribution and receptor-mediated cell activation is quantified and manipulated with the present assay.

In one embodiment, the assay can be used to monitor single cell response to stimuli with native-like responses that include changes in transcription, translation, expression, appearance of the cell, and component organization within the cell. Methods for observing and measuring interaction of external stimuli with a cell-surface molecule expressed on the cell are also provided by the assay. Quantifying receptor distribution on the cell surface and detecting transcriptional events "downstream" after receptor redistribution, such as genes that form a genetic profile for the condition, also are enabled by the assay.

The assay also allows one to observe ligand and receptor interaction. Chemical controlled ligand receptor binding can be made by a set or panoply of molecules acting together. One or more of them may bind the receptor, ultimately together forming an activation complex comprising receptors and ligands in various combinations. The activation complex may move along the cell surface to pair and group with other like activation complexes eventually forming clusters or groups of activation complexes in central assembly domains or CADs.

Other patterns on the cell surface (in addition to CAD formation) deemed representative of a condition of the tissue from which the cell is derived, also exist, and fit into the category of distribution of the receptor. Such patterns as characteristic clustering patterns (e.g. small clumping) and other different redistributions of the receptor on the surface of the cell can provide signatures for cell activation. In addition, as shown in the examples, grids or patterns can be imposed on the cell system to artificially create patterns that represent the activation. The pattern or signature that results, once correlated to the tissue or condition, can be adopted as a signature for that tissue or condition.

Any positional or structural change to the receptor in response to stimulus in the assay can affect a readout for the condition. Typically, the cell-surface molecule is labeled, and thereby "followed" on the cell surface after interaction with the chemical environment or context provided in the assay. The "view" or "look" of the cell surface after ligand receptor binding becomes then both the readout and a "signature" identifying the condition of the tissue that the cell came from. Where a test drug is employed in the assay, the assay can be used to determine whether the test drug would be effective to either enhance ligand receptor binding and response (where that would be desired) or block ligand receptor binding (if that would be best to treat the disease, condition, and patient).

Accordingly, the present assay provides a way to allow, recognize and control cell-surface receptor binding, can be used to provide direction for therapeutic intervention, where a therapeutic agent (a test drug) can be tested for an ability to alter the "signature" that has already been established either for that patient, that condition, that tissue, or that cell. Optimally, the live cells are derived from live tissue, such as human tissue, particularly tissue that is attributed to the manifestation of symptoms in the patient that are characteristic of the condition or disease.

Confirmatory indicia of receptor distribution can be detection of mRNA transcription of genes that are upregulated by the activation, or inversely, reduced RNA transcription of genes that are turned-off by the activation. In short, transcriptional modulation, and other readouts for modulation of gene expression, and protein expression, can be used to corroborate the live cell assay read-outs that manifest in cell surface detectable receptor redistribution. The gene profile can be several genes, which together identify a propensity of the cell towards a condition as yet unconfirmed in the patient The assay can be useful to test a drug for efficacy in treating patients with a known condition. A patient's tissue is harvested in a biopsy sample, and some live cells from the tissue are used for the assay. Each cell is exposed to a different activating ligand (or set of ligands), first to establish what activates the cell, and also to establish an activation index for the ligands (or sets of ligands). Thereafter, an activation signature is determined from each of various ligands, which can be compared to one another in signatures index. The index connects receptor redistribution signatures with a score for cell activation based on distribution of receptors on a pre-defined region of the cell surface. Relative increase in cell activation would be quantified by an increase in number of cell-surface molecules at the pre-defined region. Once signatures and an index is developed for ligands and ligand sets that activate the cell, test drugs can be selected for modulating any one of those activation states.

Correlation of the disease to an activation state in the assay helps to establish signatures that can be tied to the disease, progression of the disease, various forms of the disease, and specific patient indicia of the disease. For the purposes of testing a drug (and also a panoply of drugs) against a disease generally, specific states of the disease are distinguished and also made distinct from healthy tissue. Then activation (and relative quantified activation) with a particular ligand or ligand set can be correlated to indicia and progression of the disease. A test drug modulating activation of the cell in the assay will then become a candidate drug for testing further in animals, and humans.

Broad embodiments of the invention contemplate an assay for live cell activation comprising a live cell expressing a cell-surface molecule capable of activating the cell upon interaction with an external binding ligand, wherein cell activation is optically detectable upon redistribution of a plurality of the cell-surface molecules. The assay can provide that the redistribution is detectable by detecting an optical label at a pre-defined portion of the intact cell surface, and the label quantifies the live cell activation. The assay can further include access of the cell-surface molecule to at least one external binding ligand capable of interaction with the cell-surface molecule to cause cell activation.

The activation signature of a particular cell-surface molecule expressed on a particular live cell can be correlated (and indexed or catalogued) with the ligand used (e.g. known ligand or a test drug), and also correlated (and indexed or catalogued) with the condition of the tissue (e.g. healthy, diseased, developing, healing, etc.). A diseased tissue can firstly be diagnosed as such (e.g. compared to healthy tissue). Secondly, a diseased tissue can be classified by such indicia as the stage of the disease, or a prognosis for recovery (e.g. hyperplastic, dysplastic, or neoplastic; benign, malignant, metastatic; likely responsive to certain treatment, or likely non-responsive; etc.).

The conditions of the tissue can include cancerous tissue, and accordingly any of the many types of cancer known. For example, carcinomas, adenocarcinomas, epithelial cancers, myoepithelial cancers, sarcomas, gliomas, lymphomas, leukemias, carcinoids, and any other type of cancer. Any other diseased condition, not limited to cancer, can be applied to the assay where a readout can be effected and correlated to the condition. States or conditions of tissue that the assay can detect, diagnosis, classify, differentiate, and characterized include autoimmune conditions, immune system related conditions (e.g. allergies, likely immune response to challenge), likely development of resistance to standard treatments, susceptibility or predisposition to a condition (e.g. susceptibility to diabetes, thyroid conditions, stroke, cardiovascular conditions, or liver quality, function, and degeneration, etc.), and wound healing are examples of types of conditions of the tissue from which a live cell can be derived for the assay. The types of conditions of the tissue that are possible for the assay are also exemplary of the types of information that the assay can produce. Thus, for example the assay may be able to test that an individual, while not diabetic, is none-the-less pre-diabetic based on the responsiveness of a cell derived from the patient to a selected external stimuli (i.e. a ligand).

In particular, continuing with the example of cancer, comprehensive analysis of protein expression of many cancer cell lines indicates significant diversity within cell lines of the same type of cancer. The present invention can be adapted to customize SLB assays and use them for diagnosis in cancer, and for testing to find effective therapeutic interventionsIn another embodiment, a spatial reorganization phenotype was identified in the signaling role of the EphA2 receptor. As such this technological advance demonstrates the first link between large-scale protein patterns and a condition in the tissue from which the cell came. In this case the condition that is detected by the visual read-out is metastatic progression which is shown by the work reported herein across a library of human breast cancer cell lines.

FIG. 1 demonstrates that spatial organization of receptor signaling corresponds to an accumulation of ligand-receptor complexes at Cr diffusion barriers created for the assay. EphA2-expressing cells are cultured onto a supported membrane displaying laterally mobile, fluorescently labeled ephrin-A1 ligand. Receptors engage membrane-bound ligand and form clusters that coalesce and are subsequently transported to the center of the cell forming a central assembly enriched in EphA2-ephrin-A1 complex. Nanofabricated Cr lines 10 nm tall and 100 nm wide act as diffusion barriers, impeding the transport of receptor-ligand complexes and leading to an accumulation of Eph-ephrin complex at boundaries. See FIG. 3(B).

FIG. 4 shows the correlation of the radial transport phenotype with proteomic and genomic expression and more specifically, the correlation of EphA2 radial transport to molecular and behavioral properties in breast cancer. In one embodiment, an aliquot of cells (e.g., about ~50×10$^3$ cells) is plated onto ephrin-A1-functionalized supported membranes for 1 hr for each mammary epithelial cell line. Live-cell fluorescence microscopy is used to image the resulting distribution of ligand under individual cells. In one embodiment, the imaging and distribution is measured as shown by the scheme shown in FIG. 9. These radial distributions are scored, averaged across many cells for each cell line, and used as a spatial biomarker unique to each cell line and potentially associated with genomic, proteomic or phenotypic signatures in neoplasia.

In one embodiment, the radial distribution of ligand under each cell is first normalized to account for differences in cell size. Then linear regression is used to obtain the line that best fits this radial distribution, and the slope of this line is used as a radial transport score. Radial transport can also be parameterized by integrating the area under the normalized radial distribution curve, or by taking the ratio of peak-height to peak-width at the half maximum of the radial distribution curve. These techniques were averaged across many cells in each cell line to determine a signature radial transport score for each line. As shown in FIGS. 4 and 22, these different scoring methods were robust and led to strongly correlated values across 26 breast cancer cell lines.

FIG. 4 (A) shows that EphA2 radial transport, as scored using the slope of a line fit to ligand radial distribution, is strongly linked ($r=0.91$; p-value=$7.5×10^{-8}$) to invasion potential, determined using modified Boyden chamber analysis. This further provides for methods of diagnosis and prognosis using the present spatial biomarker as a marker for invasion potential.

In one embodiment, a cell, obtained from a patient suspected of having a disease, can be assayed using the presently described ephrin-A1 SLB system and method. The first step in this procedure would be to engage cells from a patient biopsy with the ephrin-A1 SLB described herein and then measure the radial distribution of ligand underneath the cells. This value could be scored as described earlier (slope of line of best fit, area under the curve, or peak height) and then interpolated to a curve of scored EphA2 radial transport vs. invasion potential, obtained from a library of cell lines with measured invasion potentials such as that described herein. This would then yield a value for the expected invasion potential or metastatic propensity for cells derived from the patient.

The transport phenotype described herein has been applied to tissue invasion because invasive cells necessarily develop different biomechanical abilities that normal cells do not, which may include receptor transport characteristics. However, it is contemplated that the present assay may be used to diagnose or prognose other diseases or conditions. Thus, in another embodiment, a cell, obtained from a patient suspected of having a disease, can be assayed using the presently described SLB system and method, whereby a radial transport score can be obtained by observing the distribution of receptor/ligand signal for the cell, and then correlated to an index of scores which has been previously correlated to disease conditions and patient outcome.

In another embodiment, the present assay can be used to provide an index of radial transport scores of cancer cell lines in other known cancers including but not limited to, prostate, ovarian, cervical, squamous, melanoma, pancreatic, lung, epithelial cancers, etc.

In another embodiment, the spatial biomarker can be used in conjunction with measuring expression profiles of a cell to provide diagnosis or prognosis of a patient. For example, a biopsy is obtained and the expression profile of at least one of the genes in Table 1, 2 or 3 is measured. The expression level of the gene is scored by comparative genomic hybridization, which uses quantitative epifluorescence microscopy to detect differences in the number of copies of fluorescently labeled DNA sequences. Other methods of measuring gene expression, or genome copy number abnormalities that may affect gene expression, may include any of the following immunohistochemistry (IHC), methods that utilize fluorescence in situ hybridization (FISH), comparative genomic hybridization (CGH), single-nucleotide polymorphism (SNP) arrays. A commercially available IHC test is PathVysion® (Vysis Inc., Downers Grove, Ill.). A commercially available FISH test is DAKO HercepTest® (DAKO Corp., Carpinteria, Calif.). Commercially available arrays include Affymetrix 250K SNP arrays (20 Kbp resolution) (Affymetrix, Santa Clara, Calif.) and Affymetrix Molecular Inversion Probe allele-specific CGH (single gene resolution). There are several publicly-accessible, fee-for-services laboratories that will perform CGH analyses, such as the Fred Hutchinson Cancer Research Center, Seattle, Wash. Gene expression patterns can also be measured using Affymetrix U133A arrays, which are described in detail in the Examples. Other commercial kits for measuring gene transcription include assays from Luminex Corporation (Austin, Tex.) (e.g., Lumiunex's "xMAP"-brand protocol) and Panomics, Inc. (Fremont, Calif.). Methods of detecting gene expression or genome copy number such as FISH and IHC with a given nucleotide sequence are described in detail in PCT/US2006/002202.

Once the radial transport score is determined, using a standard curve or index, based on the invasion potential for a panel of cell lines, one could interpolate what the invasion potential of the cell is as well as the likely outcome of the patient.

In another embodiment, the radial transport score of a cell or each cell line is correlated with proteomic and genomic expression using a system-wide linear spline analysis as described more fully in D. Das, Z. Nahle, M. Q. Zhang, *Mol. Sys. Biol.* 2, 0029 (2006), U.S. Patent Application Publication No. US2009/0177450, both of which are hereby incorporated by reference. Adaptive linear splines proceed by searching for optimal partitions in the parameter space, characteristic of multiple classes, and fitting a linear model within each partition. The fitted function is continuous, resulting in a single optimization problem. Thus, adaptive splines can simultaneously account for class information and magnitude of response in a single framework. Briefly, the response data is expressed as a sum of linear splines, where the predictor variable is the specific molecular profile of the candidate marker. For a fixed number of knots, which define the partitions, the algorithm enumeratively searches for the best location of knots by minimizing the residual sum of squares. A central challenge in predicting response in small N (cell-lines), large P (predictors) problems, is that the noise can be very strong leading to over-fitting problems. This can be controlled for by using leave-one-out cross-validation (LOOCV). LOOCV can be used to determine the optimal model size, i.e. the number of knots. A monte carlo cross-validation can be used to achieve a better control on over-fitting effects. Goodness of fit can be assessed by computing the p-value corresponding to an F-statistic.

In another embodiment, the radial transport score of a cell or each cell line is correlated with proteomic and genomic expression using the correlation of expression of genes in the cell lines before radial transport. The genes can beidentified using Affymetrix probes. Significant correlation means that in any given cell line, correlations were looked for that showed either an increase of expression parallel with radial transport in the cell, or a decrease of expression parallel with radial transport in the cell, or the opposite expression (increased when radial transport is decreased or decreased when the radial transport is increased). The statistical variations of these 3 options are computer simulated out 1000 times (Pearson 1000 permutations test) to generate a true correlating gene, or to reject it. Genes expressed in a cell that are either upregulated or downregulated in conjunction with radial transport are examined by Pearson correlation test. The correlations of expression patterns in all multiple cell lines are added together and the result is a network of genes, the expression patterns of which were specific to the radial transport phenotype. The list of genes can be selected using the Pearson Correlation Coefficient in Affymetrix expression microarray data generated from a panel of multiple human cancer cell lines. The correlation cut-off is determined by 1000 permutations test.

In another embodiment, patient response to a treatment can be determined by treating cells from a patient biopsy with a panel of potential therapeutic agents and observing which agents reverted the EphA2 transport phenotype from malignant to normal scores. Patients could then be prescribed only those agents which first show success in reverting the malignant phenotype in vitro, sparing the patient from ineffective and likely harmful therapeutic treatments.

A cell can be scored for activation with expression of downstream genes after receptor-mediated cell activation using specific genes such as EphA2, EFNA1, GRB7, ITGB1, ITGB2, CAV2, LYN and ADAM10 for the specific receptor and ligand pair studied.

The mRNA sequence for *Homo sapiens* epidermal growth factor receptor (EGFR) is found at GenBank Accession Nos. NM_005228.3 GI:41327737, NM_201284.1 GI:41327735, NM_201283.1 GI:41327733, and NM_201282.1 GI:41327731.

The mRNA sequence for *Homo sapiens* ephrin-A1 (EFNA1) is found at GenBank Accession Nos. NM_004428.2 GI:33359681 and NM_182685.1 GI:33359679.

The mRNA sequence for *Homo sapiens* growth factor receptor-bound protein 7 (GRB7), is found at GenBank Accession Nos. NM_001242443.1 GI:334883160, NM_001242442.1 GI:334883158, NM_001030002.2 GI:334883157, and NM_005310.3 GI:334883156.

The mRNA sequence for *Homo sapiens* integrin, beta 1 (fibronectin receptor, beta polypeptide, antigen CD29 includes MDF2, MSK12) (ITGB1), is found at GenBank Accession Nos. NM_002211.3 GI:182519230, NM_133376.2 GI:182507162, and NM_033668.2 GI:182507160.

The mRNA sequence for *Homo sapiens* integrin, beta 2 (complement component 3 receptor 3 and 4 subunit) (ITGB2) is found at GenBank Accession Nos. NM_000211.3 GI:188595673, and NM_001127491.1 GI:188595676.

The mRNA sequence for *Homo sapiens* caveolin 2 (CAV2)) is found at GenBank Accession Nos. NM_001206747.1 GI:332164663, NM_198212.2 GI:332164662 and NM_001206748.1 GI:332164665.

The mRNA sequence for *Homo sapiens* v-yes-1 Yamaguchi sarcoma viral related oncogene homolog (LYN) is found at GenBank Accession Nos. NM_001111097.2 GI:340745348 and NM_002350.3 GI:340745347.

The mRNA sequence for *Homo sapiens* ADAM metallopeptidase domain 10 (ADAM10) is found at GenBank Accession Nos. NM_001110.2 GI:73747882.

As described above, various methods are well-known in the art for detecting and measuring gene expression profiles in a cell using the mRNA sequences provided at the identified GenBank Accession Numbers, the contents of which are hereby incorporated in their entirety.

EXPERIMENTAL

Example 1

Many aspects of cancer result from aberrant signal transduction at the cell surface. Metastasis is one of the most deadly processes of cancer, and each of its phases (detachment, migration, invasion, growth, and survival) is regulated by cell-cell contact interactions and the associated signaling systems. For example, recent studies have found the EphA2 receptor tyrosine kinase (RTK) to be frequently over expressed and functionally altered in aggressive tumor cells (40% of breast cancers [B. L. Jackson, J. T. Groves, J. Am. Chem. Soc. 126, 13878 (2004)]), and that these changes promote metastatic character (FIG. 2A) [M. M. Davis et al., Annu. Rev. Biochem. 72, 717 (2003)]. EphA2 is one of the Eph receptors, which constitute the largest family of RTKs in the human genome and, together with their membrane-bound ephrin ligands, regulate a broad range of signaling processes at intercellular junctions. In addition to metastasis, Eph receptors are involved in oncogenic transformation and tumor-driven induction of angiogenesis. Since both the Eph receptors and their ephrin ligands are associated with the cell membrane, this family of cell surface signaling molecules are ideally suited to reconstitution into the hybrid live cell—supported membrane configuration.

Previously, to test the ability of the SLB platform to distinguish between metastatic and non-metastatic cells, an ephrinA1-functionalized supported lipid bilayer (EA1-SLB) was designed. This environment was then presented to various cancer cell lines. Decreased spreading was observed when metastatic cancer cells (MDA-MB-231) displaying the EphA2 receptor were cultured in this environment. When non-metastatic cancer cells (T47D) not displaying the EphA2 receptor were cultured under the same conditions, no change in behavior was observed.

For Examples 1-9, the following Materials and Methods were used.

Supported Membrane Preparation. Phospholipid vesicles were prepared using existing methods (D. E. Discher, P. Janmey, Y. L. Wang, Science 310, 1139 (2005)). In short, the desired lipids were mixed in a chloroform solution and then the chloroform was evaporated using a rotary evaporator. The lipids were thoroughly dried under a stream of $N_2$ and hydrated with 1.5 mL of DI water. The hydrated lipids were then extruded through 100 nm-sized polycarbonate pore filters and stored at 4° C. Fluid bilayers were made from vesicles containing 99.9% DMPC (1,2-dimyristoyl-sn-glycero-3-phosphocholine) or DOPC (1,2-dioleoyl-sn-glycero-3-phosphocholine), and 0.1% biotin-DPPE (1,2-dipalmitoyl-sn-glycero-3-phosphoethanolamine-N-(cap biotinyl)). Fluorescence recovery after photobleach experiments were performed with bilayers containing 3% NBD-PC (1-acyl-2-{12-[(7-nitro-2-1,3-benzoxadiazol-4-yl) amino]lauroyl}-sn-glycero-3-phosphocholine), 96.9% DMPC, and 0.1% biotin-DPPE. Quantitative fluorescence standard solutions are described below. Unless otherwise noted, all lipids were acquired from Avanti Polar Lipids, Inc., Alabaster, Ala. Vesicles were allowed to warm to room temperature and mixed in a 1:3 ratio with 1× phosphate-buffered saline (PBS; Sigma-Aldrich, Inc., Saint Louis, Mo.) to a final concentration of 1 mg/ml.

For experiments performed in 96-well plates, each well was pre-treated with 1 M NaOH for 1 hour and then thoroughly rinsed with DI water. 100 µl of the lipid vesicle solution in PBS was then added to each well and excess vesicles were subsequently rinsed. For experiments performed on microscopic cover glass, substrates were cleaned using a piranha etching protocol ($H_2SO_4$ and $H_2O_2$ mixed in a 3:1 ratio) for 15 min, and then rinsed and dried under a stream of $N_2$. Lipid vesicle solutions were then spread over these substrates. The resulting lipid-bilayer functionalized substrate was immersed in PBS and sealed in an Attofluor cell chamber (Invitrogen Corp., Carlsbad, Calif.)

Non-fluid supported membranes were generated from lipid vesicles that were composed of 99.9% DPPC and 0.1% biotin-DPPE. In order to facilitate vesicle rupture and spreading, lipid solutions were extruded through 100 and 30 nm-sized pore filters and all solutions and substrates were heated to 50° C.

Surface Functionalization. After lipid bilayer deposition, substrates were incubated for 45 min with a 0.01% bovine serum albumin (BSA; Sigma-Aldrich, Inc.) solution to minimize non-specific protein adsorption. The supported membranes were then incubated with a 17 nM solution of streptavidin (Fisher Scientific, Pittsburgh, Pa.) for 45 minutes. For experiments that quantify protein surface density, streptavidin conjugated to Alexa Fluor 488 (Invitrogen Corp.) was substituted for the unlabeled protein. The supported membrane was then thoroughly rinsed and substrates were incubated for 45 min with a 50 nM solution of ephrin-A1 (R&D Systems, Minneapolis, Minn.), which had been biotinylated (Fisher Scientific) and conjugated to Alexa Fluor 594 or Alexa Fluor 647 (both from Invitrogen Corp.). RGD-functionalized supported membranes were generated by incubating streptavidin-functionalized membranes with a cyclic peptide [Arg-Gly-Asp-d-Phe-Lys(Biotin-PEG-PEG)] where PEG=8-Amino-3,6-Dioxaoctanoic Acid (PCI-3697-PI, Peptides International, Louisville, Ky.) at the molar concentrations indicated.

In all cell experiments, the PBS solutions were exchanged by rinsing the substrate with DMEM cell media (GIBCO) at 37° C. Cells were then added to the substrates and allowed to engage and interact with the surface at the conditions indicated.

Optical Microscopy. We used Nikon Eclipse TE2000-E and TE300 inverted microscopes with mercury arc lamps for epifluorescence illumination and 12 V, 100 W halogen lamps for bright field illumination. Total internal reflection fluorescence (TIRF) illumination was provided using a krypton/argon ion laser for 647 nm excitation, and an argon ion laser (Stabilite 2018 and Model 177 respectively, both from Spectra-Physics, Mountain View, Calif.) for 488 nm excitation. All epifluorescence microscope images were taken with a Quantix CCD camera and TIRF microscope images were taken using a Cascade 512B EMCCD camera. All cameras were purchased from Roper Scientific, Ottobrunn, Germany. MetaMorph (Molecular Devices Corp., Downington, Pa.) software was used to drive microscope and collect the images. Alexa Fluor 647 was imaged using a Cy5 filter cube, Alexa Fluor 594 and Texas Red were imaged using a TR filter cube, Alexa Fluor 488 and NBD were imaged using an NBD/HPTS filter cube, and Alexa Fluor 350 and Hoechst 33342 were imaged using a DAPI/Hoechst/AMCA filter cube. Reflection interference contrast microscopy (RICM) images were collected using a dedicated RICM filter cube. All filter cubes were acquired from Chroma Technology Corp., Rockingham, Vt. Alexa Fluor 647 Ephrin-A1 and EGFP-actin tracking was performed using a DualView (Photometrics, Tucson, Ariz.) image splitter fitted with a dual-band pass emission filter interposed between the body of the microscope and the camera. Time-lapse images were collected using a Physitemp TS-4 thermal microscope stage (Physitemp Instruments, Inc., Clifton, N.J.), in conjunction with a home-built heating element attached to the microscope objective, to maintain the sample temperature at 37° C. over the course of the experiment.

Quantitative Epifluorescence Microscopy. The surface density of ephrin-A1 on supported membranes was measured using a recently developed quantitative fluorescence microscopy technique (2). First, vesicles containing 0.1 mol % TR-DHPE (Texas Red-1,2-dihexanoyl-sn-glycero-3-phosphoethanolamine, Invitrogen Corp.) and 99.9 mol % DMPC (1,2-dimyristoyl-sn-glycero-3-phosphocholine) were added to PBS in varying proportions yielding solutions whose final concentrations ranged from 0-0.74 µM Texas Red. These solutions were used to establish a bulk lipid calibration plot where fluorescence intensities, as measured using a Nikon TE300 microscope, were plotted against the concentration of the TR-DHPE. The data were fit to a straight line with a y-intercept of 0 and this slope was designated as $I_{solu(lipid)}$.

Subsequently, a bulk protein calibration plot was generated from a serial dilution of Alexa Fluor 594 (Invitrogen)-labeled ephrin-A1 (594-EA1) where the solution concentrations ranged from 0-0.305 µM. Fluorescence from these solutions was measured using the same acquisition settings as the ones used for the lipid vesicle standards. Fluorescence intensity was plotted against [594-EA1] and fit to a straight line with a y-intercept set to 0, and the calculated slope was designated as $I_{solu(sample)}$. From these bulk calibration standards, a scaling factor was calculated to express the difference in fluorescence intensities between fluorescent lipids and proteins: $F = I_{solu(sample)} / I_{solu(lipid)}$.

On the day of the experiment, a surface bilayer calibration curve was generated using lipid membranes that were doped with TR-DHPE at concentrations that ranged from 0 to 0.62 mol % TR-DHPE. Bilayer fluorescence was measured and plotted against the molecular density of Texas Red per $\mu m^2$, by using 0.569 $nm^2$ as the average footprint of each lipid molecule (3). These data were fit to a straight line with a y-intercept of 0, and the calculated slope was labeled as $I_{bilayer(lipid)}$. The scaling factor was applied to obtain the slope of a line describing fluorescence intensity versus the number of 594-EA1 molecules per $\mu m^2$, $I_{bilayer(sample)} = F*I_{bilayer(lipid)}$.

Then, using the same acquisition settings, the fluorescence intensities of unknown bilayers containing 594-EA1 were measured. The measured fluorescence intensities was plotted on a line with slope $I_{bilayer(sample)}$ and y-intercept 0, allowing for a determination of the corresponding molecular density of 594-EA1 per $\mu m^2$. Using this quantitative fluorescence technique, the concentration of 594-EA1 in the bilayer was tuned to 800±200 molecules/$\mu m^2$, when the concentration of biotinylated lipids in the bilayer was 0.1 mol %.

Quantitative TIRF Microscopy. In order to account for differences in illumination intensity across the visualized area between 488 nm and 647 nm laser TIRF excitation, a calibration bilayer was used. The calibration bilayer contained 99.9% DOPC and 0.1% biotin-modified DHPE and was incubated for 45 minutes with a 1:1 mixture of Alexa Fluor 488 streptavidin and Alexa Fluor 647 streptavidin, each with a F/P ratio of 2. The bilayer was then rinsed with PBS. Several unique areas of the calibration bilayer were imaged in the 488 nm and 647 nm excitation channels. An average, background-subtracted image was obtained for each channel. Background-subtracted sample images from each channel were divided by the average background-subtracted calibration image for the same channel, yielding sample images with normalized illumination intensities that could be quantitatively compared between the 2 channels for the entire field of view.

The ratio of signal from the ADAM10 channel to signal from the EphA2 channel was calculated independently for each cell. The Pearson's coefficient for these two channels was also calculated independently for each cell. These quantities were obtained using image analysis software package ImageJ (Rasband, W. S., ImageJ, U.S. National Institutes of Health, Bethesda, Md., USA, <http://rsb.info-.nih.gov/ij/>, 1997-2009). Average values for these quantities±SE are displayed in FIG. 4B.

Flow Cytometry. EphA2 expression on the surface of MDA-MB-231 cells was measured using flow cytometry. Briefly, cells were detached from cell culture flasks using trypsin-EDTA and incubated for 30 minutes in a 1% solution of bovine serum albumin in PBS to minimize non-specific antibody binding. Cells were incubated for 1 hour in a 1.25-5 µg/ml solution of mouse $IgG_{2A}$ anti-EphA2 antibody (MAB3035, R&D Systems). Primary antibodies were rinsed away with PBS and cells were incubated for 30 minutes in a 5-10 µg/ml solution of goat anti-mouse $IgG_{2A}$ antibody conjugated to fluorescein isothiocyanate (FITC). Secondary antibodies were rinsed away with PBS and cell solutions were analyzed using a Beckman-Coulter EPICS XL Flow Cytometer. Least squares analysis was performed on flow cytometry measurements of silica microspheres conjugated to known quantities of FITC (Bangs Laboratories, Inc., Fishers, Ind.) to determine the curve that best fit fluorescence intensity vs. number of fluorophores. Flow cytometry measurements of EphA2-labeled cells were then collected and fit to the calibration curve, yielding the average number of fluorophores on each cell (6.43×10$^5$ fluorophores per cell). This quantity was then divided by the labeling ratio of FITC-conjugated antibody and the average surface area of a cell to determine the average number of EphA2 molecules per $\mu m^2$ (~400 EphA2 molecules/$\mu m^2$).

Electron-beam Lithography. Chromium designs were fabricated on 25 mm diameter round glass coverslips. Coverslips were etched for 2 minutes in piranha solution (3:1 $H_2SO_4:H_2O_2$), then spin-coated at 1000 RPM with EB-resist (ZEP-520A, Zeon) and conductive polymer (Aquasave, Mitsubishi Rayon). Resist was exposed via electron beam lithography (CABL9510CC, Crestec) at 100-150 µC/cm$^2$. Patterns fabricated were square grids with spacing 0.5, 1, 3, 5 and 20 µm and crosses with spacing 3 µm. Conductive polymer was removed by deionized water rinse and resist was developed by sonication for 1 minute in isoamyl acetate. Chromium was deposited by electron beam evaporation and resist mask was lifted off by sonication in methylene chloride. Patterns exhibited film thicknesses of 10 nm and grid line widths of 100 nm, as verified by AFM measurements (FIG. 16).

Radial Transport Analysis. Bright field microscopy was used to determine the area occupied by each cell. The corresponding areas in the fluorescence channel were then analyzed using the Radial Profile plugin from ImageJ, yielding a plot of normalized fluorescence intensities versus radial distance from the cell center. Plots were then normalized for cell size and averaged. Least squares analysis was then performed on the average normalized radial distribution using Origin 7.0 (OriginLab, Northampton, Mass.), and the slope of the calculated line was used as a score for propensity to radially transport ephrin-A1.

Cell fixing and membrane permeabilization. For immunofluorescence experiments cells were cultured on substrates for 1 hour. Cells were then rinsed with cold Dulbecco's PBS (Invitrogen Corp.) and fixed with 4% paraformaldehyde (EMD Chemicals, Inc., Gibbstown, N.J.) in PBS (Invitrogen Corp.) for 12 minutes. When noted, cells were permeabilized with 0.1% Triton-X (EMD Chemicals, Inc.) in PBS for 5 minutes. Cells were then incubated overnight at 4° C. in PBS containing 1% BSA to block non-specific antibody binding.

Cell Staining. After fixing, cells were stained for 40 minutes with primary antibodies against a variety of target molecules. Anti-integrin $\alpha_v\beta_3$ (MAB3050, R&D Systems Inc.) and anti-integrin $\alpha_v\beta_5$ antibodies (MAB 2528, R&D Systems, Inc.) were incubated at 10 µg/ml and anti-integrin $\beta_1$ (sc-9936) was incubated at 2 µg/ml. For EphA2, ephrin-A1, ADAM10, phosphotyrosine, CD44 and F-actin staining, cells were permeabilized before antibody or phalloidin addition. Anti-EphA2 antibody (sc-924) and anti-ADAM10 (sc-48400) antibodies were incubated at 2 µg/ml. Anti-phosphotyrosine (05-321, Millipore, Temecula, Calif.) and anti-CD44 (sc-51610) antibodies were incubated at 1 µg/ml. For co-culture experiments, anti-ephrin-A1 (sc-20719) was incubated for 20 minutes at 4 µg/ml. Unless otherwise noted, antibodies were purchased from Santa Cruz Biotechnology, Inc., Santa Cruz, Calif.

After primary antibody incubation, excess antibody was rinsed away with PBS containing 1% BSA and isotype-matched secondary antibodies conjugated to either Alexa Fluor 488 or Alexa Fluor 647 (Invitrogen Corp.) were incubated at a concentration of 2 µg/ml for 20-30 minutes. Excess secondary antibody was rinsed away with PBS.

F-actin was stained using phalloidin conjugated to Alexa Fluor 350, Alexa Fluor 488, or Alexa Fluor 647 (Invitrogen Corp.), according to manufacturer protocols.

For EphA2-blocking studies, cells were pre-treated with anti-EphA2 antibody raised against an epitope on the extracellular domain of EphA2 (MAB3035, R&D Systems, Inc.). Excess antibody was rinsed away with cell culture media, and isotype-specific secondary antibody conjugated to Alexa Fluor 488 was added to the cell solution as before. Excess secondary antibody was rinsed away with cell culture media, and cells were cultured on ephrin-A1-functionalized supported membranes as described earlier.

ROCK Inhibition. Cells were detached from cell culture flasks using trypsin-EDTA and incubated at 37° C. for 2 hrs in media containing ROCK inhibitor Y-27632 (Sigma-Aldrich, Inc.) at concentrations ranging from 1-50 µM. Trypan blue staining and cell counting indicated no adverse effects in terms of cell viability under these conditions. Cells were cultured in drugged media for one hr on well plates containing Alexa Fluor 647-labeled ephrin-A1 functionalized supported bilayers. Cells were fixed, stained and imaged with epifluorescence microscopy as described above.

Colocalization Analysis. After culturing cells on substrates for 1 hour, cells were fixed, cell membranes were permeabilized, and target molecules were stained and then imaged using TIRF microscopy as described above.

Areas occupied by cells (20 µm×20 µm in size) were chosen using bright field images. These same areas were designated as regions of interest in ImageJ and cropped for further analysis. To calculate the ratio of ADAM10/EphA2 signal, the net intensity in the ADAM10 (488 nm excitation) channel was divided by the net intensity in the EphA2 (647 nm excitation) channel. To calculate the Pearson correlation coefficient, intensity of each pixel in the ADAM10 channel was plotted against pixel number. Similarly, intensity of each pixel in the EphA2 channel was plotted against pixel number. Least squares analysis was performed to fit a straight line to intensity values from each channel. The Pearson correlation coefficient was determined as the correlation coefficient between these 2 lines.

Cell Culture. Cells were provided by the Gray Lab (Lawrence Berkeley National Laboratory) and cultured using media, supplements, and conditions provided by the Integrative Cancer Biology Program (<http://icbp.lbl.gov/breastcancer/cellines.php>). The day of the experiments, cells were treated with trypsin-EDTA, centrifuged, resuspended in media, counted, and aliquoted as needed. Aliquots were kept in a 37° C., 5% $CO_2$, 100% humidity incubator until they were added to supported membranes.

EGFP β-actin Transfection. MDA-MB-231 cells were transfected with a plasmid containing an enhanced green fluorescent protein (EGFP) β-actin fusion construct (C. S. Chen, J. Cell Sci. 121, 3285 (2008); construct (M. J. Dalby et al., Nat. Mater. 6, 997 (2007))) using Lipofectamine 2000 (11668-019, Invitrogen Corp.) according to manufacturer protocols. Cells were harvested 24 hrs after transfection.

Co-culture Experiments. For the studies to observe ligand and receptor assembly formation at live cell-cell contacts, EphA2-expressing MDA-MB-231 cells were grown in co-culture with ephrin-A1-expressing ZR-75-1 cells. First, MDA-MB-231 cells were cultured to confluency in wells containing RPMI cell media. Then, ZR-75-1 cells were labeled with the nuclear stain Hoechst 33342 (Invitrogen Corp.) at a concentration of 1 µg/ml for 30 minutes, then added to wells containing MDA-MB-231 cells. Cells were grown in co-culture for 1 hour, the time at which ephrin-A1 macrocluster formation was visually complete on supported membranes. Cells were then fixed for 20 minutes with 4% paraformaldehyde and stained with primary antibodies specific for ephrin-A1. Then the cells were imaged using bright field and epifluorescence microscopy, as described above.

Western blotting. Western blots were performed on lysates collected from ~$1\times10^5$ cells cultured on supported lipid membranes for 2 hours. To collect the cell lysates, each sample was placed on ice and supernatant from each substrate was collected. Each substrate was rinsed with 2 ml of cold Dulbecco's PBS and the rinses were added to the supernatant fractions. The combined rinses and supernatant from each substrate were centrifuged at 250 g for 5 minutes at room temperature and the supernatant was aspirated. Each cell pellet was then resuspended in 50 µl of NP-40 buffer. 100 µl of NP-40 buffer was added to each substrate and adhered cells were scraped off the substrate and added to the cell pellet previously resuspended, as was the NP-40 remaining on the substrate surface. The solution was then centrifuged at 15000 g for 15 minutes at 4° C. and the supernatant was collected and stored in at −80° C. until the day of blotting.

Western blots were labeled with primary antibodies specific to EphA2 (05-480, Millipore), phosphotyrosine (05-321, Millipore), and actin (sc-1616, Santa Cruz Biotechnology, Inc.). Samples were labeled with isotype-matched secondary antibodies conjugated to Alexa Fluor 680 or Alexa Fluor 780 (Invitrogen Corp.), and imaged using an Odyssey Infrared Scanning System (LI-COR Biotechnology, Lincoln, Nebr.).

Identification of molecular predictors of the EphA2 radial transport phenotype. The slope of the radial distribution function characteristic of the receptor reorganization phenotype was correlated with the expression levels of mRNA transcripts and proteins across the panel of breast cancer cell lines (C. Ballestrem, B. Wehrle-Haller, B. A. Imhof, J. Cell Sci. 111, 1649 (1998)) using an in vitro systems approach. The approach was comprised of evaluating each transcript and protein individually to determine whether it was significantly correlated with EphA2 radial transport, and to identify the signaling pathways that are enriched among these predictors. In these analyses, we used 26 breast cell lines for which both phenotype and expression data were available. The statistical significance of the correlation was assessed using F-statistic (R. M. Neve et al., Cancer Cell 10, 515 (2006)), and the p-values were corrected for multiple hypotheses testing using the false discovery rate (FDR) method (D. Das, Z. Nahle, M. Q. Zhang, Mol. Sys. Biol. 2, 0029 (2006)). Our analysis led to 141 mRNA transcripts ($p<1\times10^{-4}$, FDR$<5\times10^{-3}$; 158 probesets, Table 1) and 37 proteins (p<0.1, table S2) that are significantly associated with the EphA2 reorganization phenotype. We applied the DAVID analysis program to the significant proteins to identify the enriched pathways from the KEGG (Table 3) and BioCarta (Table 4) databases (J. D. Storey, R. Tibshirani, Proc. Nat. Acad. Sci. USA 100, 9440 (2003)). We used a stringent FDR cutoff of 5% to ascertain statistical significance of the pathways. Many mRNAs do not have pathway association, which prevented us from performing equivalent pathway enrichment analysis for the mRNAs. However, unsupervised hierarchical clustering of mRNA expression levels of the 141 significant genes led to two distinct clusters of breast cell lines—one with large slope (magnitude), and the other with low slope (FIG. 3C), demonstrating that the mRNAs can collectively predict the EphA2 reorganization phenotype.

Example 2

Activation of the EphA2 receptor tyrosine kinase by ephrin-A1 ligands presented on apposed cell surfaces plays important roles in development and exhibits poorly understood functional alterations in cancer. Here, we reconstitute this intermembrane signaling geometry between live EphA2-expressing human breast cancer cells and supported membranes displaying laterally mobile ephrin-A1. Receptor-ligand binding, clustering, and subsequent lateral transport within this junction are observed. EphA2 transport can be blocked by physical barriers nanofabricated onto the underlying substrate. This physical reorganization of EphA2 alters the cellular response to ephrin-A1, as observed by changes in cytoskeleton morphology and recruitment of the protease ADAM10. Quantitative analysis of receptor-ligand spatial organization across a library of 26 mammary epithelial cell lines reveals characteristic differences that strongly correlate with invasion potential. These observations reveal a mechanism for spatio-mechanical regulation of EphA2 signaling pathways.

A supported fluid membrane doped with 0.1% biotin-functionalized lipid was used to generate an artificial laterally mobile ephrin-A1 presenting cell surface. The density of ligand was adjusted to 300±30 molecules/mm$^2$ or 800±200 molecules/μm$^2$ (W. J. Galush, J. A. Nye, J. T. Groves, *Biophys. J.* 95, 2512 (2008)), which is comparable to the density of the EphA2 receptor (200-600 molecules/mm$^2$) on the surface of a representative invasive breast cancer cell line, MDA-MB-231.

When EphA2-expressing cells make contact with functionalized supported membranes displaying fluorescently labeled ephrin-A1, ephrin-A1 becomes organized into microclusters over the course of 15 min (FIG. 2A, B). The receptor engages in ligand forming receptor-ligand complexes that are then subject to cell-driven lateral organization and transport. Real-time live-cell fluorescence imaging indicates that immediately upon receptor-ligand binding, clusters form within the cell-bilayer interface (FIG. 2A). The dimerization and oligomerization of Eph receptors upon ligand stimulation is well-documented. Higher-order clusters have been proposed and shown to exist based on structural studies of the molecular interfaces in Eph-ephrin complexes.

The formation of such clusters was observed, and within minutes of ligand engagement these clusters nucleate the growth of larger aggregates that coalesce and are subsequently transported laterally to the center of the cell-membrane interface, thus forming a large-scale domain of Eph-ephrin complex (FIG. 2A, FIG. 1). The circular multi-micron structure is called the central assembly domain (CAD) (FIG. 1). The typical dynamics of CAD formation were recorded by measuring the radial distribution of ligand as a function of time for 80 cells over a period of 90 min (FIG. 2A). Note that CAD formation is not an artifact of the supported membrane platform, as both ligand (FIG. 2B) and receptor (FIG. 1) are actively driven into a central assembly at live cell-cell junctions (FIG. 2B).

We additionally observe the microclusters to undergo inward radial transport while still bound to the supported membrane, as confirmed by live-cell fluorescence imaging and reflection interference contrast microscopy (RICM), which reveals cell-substrate contact distances (H. Verschueren, *J Cell Sci* 75, 279 (1985)) (FIG. 8). Radial transport characteristics can be quantified for a population of cells by averaging the radial distribution of ligand underneath each cell at defined time points (FIG. 2B, 9). Two-color total internal reflection fluorescence microscopy (TIRFM) tracking of ephrin-A1 and enhanced green fluorescent protein (EGFP) β-actin reveals significant co-movement between image pairs, suggesting association of the actin cytoskeleton with EphA2 clusters (23) (FIG. 10). Further experiments with a Rho kinase inhibitor (detailed below) confirm EphA2 transport is driven by actomyosin contractility.

Example 3

The fluidity of the membrane is critical for observing CAD formation, and fully saturated 1,2-dipalmitoyl-sn-glycero-3-phosphocholine (DPPC) lipids that are non-fluid at 37° C. do not allow the coalescence of microclusters and their subsequent transport into the CAD (FIG. 2E).

To evaluate how the supported membrane affects EphA2 activation, we measured the degradation of EphA2, which is a direct consequence of ligand-induced receptor stimulation. Western blots measuring EphA2 degradation (FIG. 2D), indicate that membrane-bound ephrin-A1 activates EphA2 to the same degree as soluble ligand stimulation (1 ng/ml). However, ephrin-A1 anchored to non-fluid DPPC membranes can only activate EphA2 to ~50% of the maximum achieved with fluid membranes (FIG. 2D). These results clearly indicate that the activity of chemically identical ligands can be modulated by altering membrane fluidity, thus suggesting an additional level of finely tuned responses in Eph-ephrin signaling.

This correlated with differences in EphA2 signaling as measured by receptor phosphorylation and degradation, which are hallmarks of ligand-induced activation (J. Walker-Daniels, D. J. Riese, M. S. Kinch, *Mol. Cancer Res.* 1, 79 (2002)). When identical numbers of cells (~1×10$^5$) were plated onto fluid and non-fluid supported membranes doped with an identical density of ephrin-A1 binding sites (1:1000 biotin-DPPE), the ephrin-A1 tethered to non-fluid DPPC membranes induced approximately 50% less EphA2 degradation, and approximately 40% less tyrosine phosphorylation than did ephrin-A1 tethered to control fluid membranes (FIG. 2F). Furthermore, on fluid membranes, ephrin-A1 clusters colocalized with the areas of highest tyrosine phosphorylation and radial transport of Eph-ephrin complexes coincided with significant f-actin reorganization (FIG. 2C, 15).

Example 4

To determine how central assembly formation influences adhesion, reflection interference contrast microscopy (RICM) was used to characterize cell-supported membrane junctions (FIG. 2C). The CAD appears to colocalize with the darkest region of the RICM image, indicating that Eph-ephrin interactions support a tight junction with an intermembrane distance<30 nm. This region also colocalizes with the areas of highest tyrosine phosphorylation, indicating a significant level of kinase activity (FIGS. 2C, 15). Additionally f-actin forms an annulus around the periphery of the CAD which suggests its involvement in cytoskeletal reorganization on a global cell-wide scale.

Example 5

Figure 12:
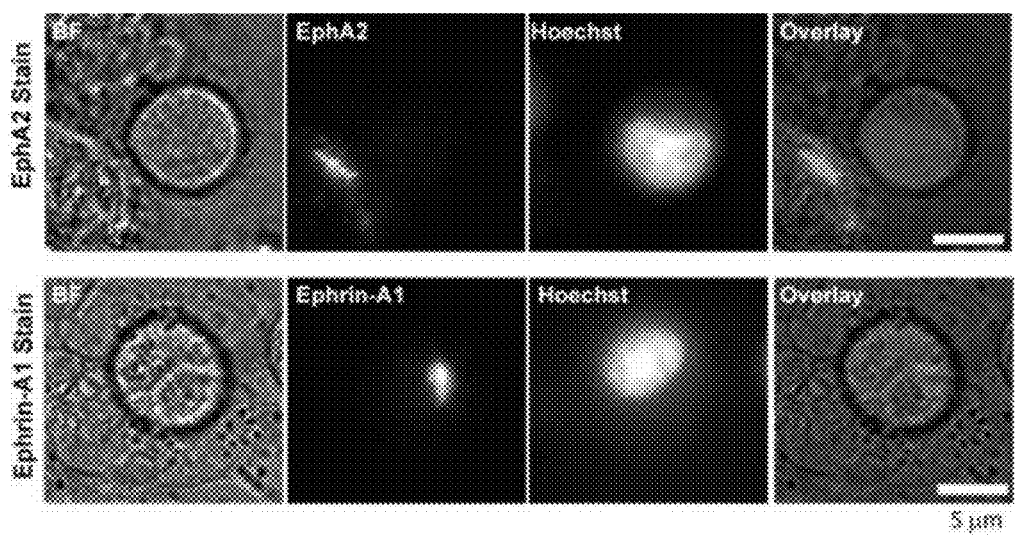

The eight different EphA receptors and the five ephrin-A ligands are known to display some promiscuous interactions, but control experiments indicate that ephrin-A1 specifically binds EphA2 (K. Kullander, R. Klein, *Nat. Rev. Mol. Cell Biol.* 3, 475 (2002)). Firstly, the EphA2 receptor was highly colocalized with ephrin-A1 (FIG. 11A). Additionally, when cells were pretreated with EphA2 antibodies that block the binding site for ephrin-A1, no ligand clustering or cell-surface adhesion was observed (FIG. 11B). Large-scale clustering of EphA2 in live cell junctions was also observed when cells that express ephrin-A1 (ZR-75-1) and cells that express EphA2 (MDA-MB-231) were brought into contact for 1 hr. Immunostaining of cellular junctions using antibodies specific to the ectodomain of either ephrin-A1 or the EphA2 receptor indicated accumulation at the contact zone between cells displaying cognate receptor-ligand pairs. Such accumulations resemble those observed in cell-supported membrane experiments (FIG. 2A, 12). Radial transport of receptor-ligand complex was not observed when ephrin-A1-expressing cells contacted EphA2-functionalized supported membranes (FIG. 13); thus receptor translocation is ligand-induced and driven only by the EphA2-expressing cells.

In the preceding experiments, Eph-ephrin binding provided the only physical link between the cell and the supported membrane. RICM confirmed that EphA2-ephrin-A1 clusters colocalize with the regions of closest intermembrane contact (FIG. 2C). To determine if the observed inward radial transport may be an indirect consequence of intermembrane anchoring, a cyclic RGD peptide-lipid conjugate was included in the supported membrane. This peptide serves as a binding partner for integrins on the cell surface (J. D. Humphries, A. Byron, M. J. Humphries, *J. Cell Sci.* 119, 3901 (2006)), and was presented as a binary mixture with ephrin-A1 on the supported membrane in varying densities. RICM images revealed progressively larger cell—supported membrane contact areas with increasing RGD peptide density, but with no change in EphA2 organization (FIG. 2D). Immunostaining for $\beta_1$, $\alpha_v\beta_3$ and $\alpha_v\beta_5$ integrins, known markers of focal adhesions, did not show colocalization with EphA2 (FIG. 14). Thus we conclude that the radial transport of EphA2 is selective and independent of integrin-mediated adhesion and signaling.

Example 6

Cytoskeleton reorganization is known to result from ligand-dependent tyrosine phosphorylation of EphA2 and subsequent downstream signaling processes (N. Carter, T. Nakamoto, H. Hirai, T. Hunter, *Nat. Cell Biol.* 4, 565 (2002). This ultimately contributes to cell contact-dependent repulsion and tissue patterning (K. Kullander, R. Klein, *Nat. Rev. Mol. Cell Biol.* 3, 475 (2002)). EphA2 can remodel the cytoskeleton through activation of the small GTPase RhoA (M. L. Taddei et al., *Am. J. Pathol.* 174, 1492 (2009)), a process implicated in the high motility and invasive ability of malignant tumor cells (P. Friedl, K. Wolf, *Nat. Rev. Cancer* 3, 362 (2003)). To explore the effects of this process on EphA2 transport we utilized the selective Rho-associated kinase (ROCK) inhibitor Y-27632 to block actomyosin contractility (P. P. Provenzano, D. R. Inman, K. W. Eliceiri, S. M. Trier, P. J. Keely, *Biophys. J.* 95, 5374 (2008)). MDA-MB-231 cells treated with inhibitor concentrations ranging from 1 to 50 µM exhibited a dose-dependent decrease in their capacity to transport EphA2-ephrin-A1 complexes to the center of the cell-supported membrane contact junction (FIG. 2G). This observation indicates that EphA2 transport is actively driven by actomyosin contractile forces.

To address the biochemical role of EphA2 spatial organization, the inventors quantify its effect on tyrosine phosphorylation (pY) since this is the key step in receptor tyrosine kinase signal transduction and regulation. This was performed by comparing pY levels of identical cells that were forced to form different patterns of EphA2. The native organization of EphA2 was prevented by nano-patterning chromium diffusion barriers into the supported membrane. These were generated using electron-beam lithography with 5-10 nm heights and 100 nm widths. Lipids and membrane-tethered proteins diffuse freely, but cannot cross barriers (K. D. Mossman, G. Campi, J. T. Groves, M. L. Dustin, *Science* 310, 1191 (Nov. 18, 2005).; N. C. Hartman, J. A. Nye, J. T. Groves, *Proc. Natl. Acad. Sci. USA* 106, 12729 (2009); J. T. Groves, S. G. Boxer, *Acc. Chem. Res.* 35, 149 (2002)) (FIG. 17). Upon binding its supported membrane-bound ephrin-A1 ligand, the EphA2 receptor and other physically associated signaling molecules become subject to the same geometrical constraints to mobility. Cells are unable to transport receptor-ligand complexes across the barriers, resulting in the accumulation of ephrin-A1 at the chromium boundaries (FIG. 17). By altering the pitch of the nano-patterned barriers, we introduce a variety of non-native spatial configurations to the central assembly. Although fluorescence imaging indicated that the CAD was heavily phosphorylated, the quantitative analysis of the ratio of total pY to ephrin-A1 indicates that pY decreases as larger scale assemblies are permitted to form. Immunofluorescence imaging of cells on grid-patterned constraints reveals that the confined EphA2 clusters remain heavily phosphorylated in all cases (unrestricted, 3, 1, and 0.5 µm pitch diffusion barriers). EphA2 is locally triggered irrespective of geometrical constraint (FIG. 3A).

In contrast, the morphology of the f-actin exhibited two discrete states as a function of the degree of physical partitioning forced onto the EphA2 receptor pattern. Cells engaging membranes with 500 nm-pitch barriers displayed a spreading morphology, with f-actin primarily in peripheral lamellipodia. This behavior is similar to that observed in cells cultured on standard glass slides or on RGD-functionalized surfaces without ephrin (FIG. 18). The actin morphology dramatically changed into an annulus immediately surrounding the EphA2-ephrin-A1 assembly when cells were exposed to substrates with grid barrier pitches of 3 µm or larger (FIG. 3A). These observed differences in f-actin morphology at identical ephrin-A1 densities indicate that physical resistance to EphA2 receptor transport can change the threshold for ephrin-A1-triggered cytoskeleton reorganization. This suggests that CAD formation may serve to attenuate ligand-dependent EphA2 activation.

Example 7

Figure 3C:
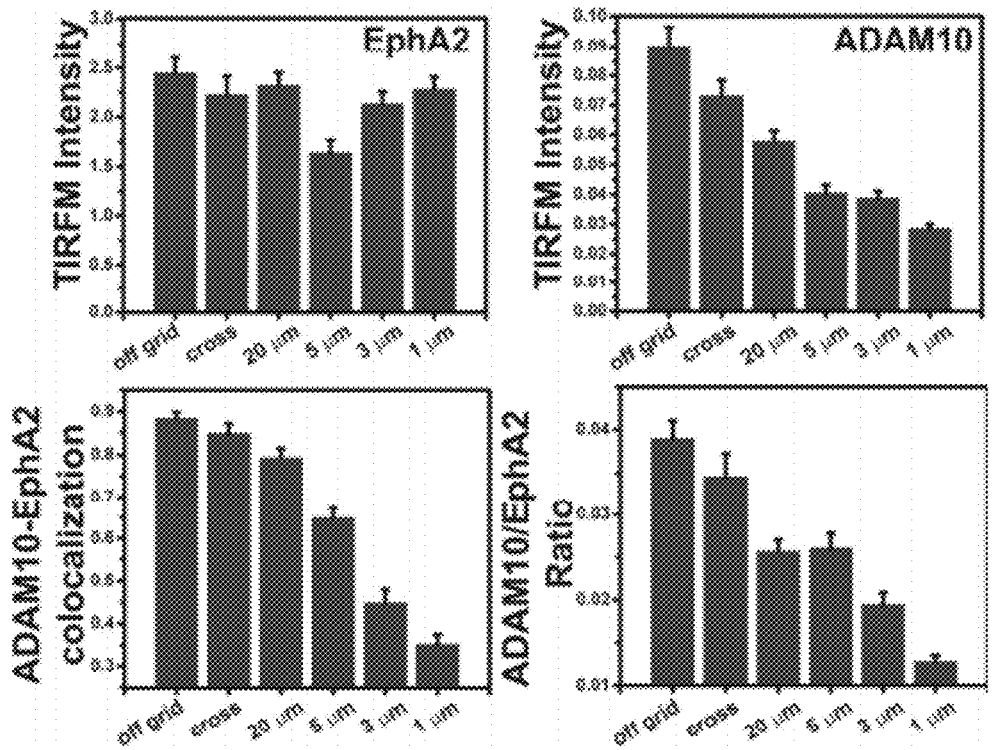

One mechanism that can explain pY dampening is the recruitment of effector molecules such as ADAM10 (A disintegrin and metalloprotease 10), a zinc-dependent transmembrane protease to the central assembly. ADAM10, is implicated in the ectodomain trans-shedding of ephrin-As as a consequence of Eph receptor binding (P. W. Janes et al., *Cell* 123, 291 (2005)). ADAM10 has been shown to weakly associate with Eph receptors at the plasma membrane and to preferentially bind receptor-ligand complexes. Proteolytic cleavage by ADAM10 occurs at the extracellular domain of ephrin-As and is hypothesized to initiate release and endocytosis of the receptor-ligand complex (Ibid). This releases the physical receptor-ligand tether between apposed cells and is hypothesized to result in the observed Eph-driven cell repulsion, rather than expected cell adhesion. When cells are cultured on patterned substrates and triggered with fluid ephrin-A1 for 1 hour and then stained for ADAM10, we observe that ADAM10 is selectively recruited to the CAD (FIG. 3B, 20). However, when the EphA2 large-scale central assembly is forced into smaller microclusters, ADAM10 staining intensity is dramatically reduced and selective colocalization with EphA2 is abrogated at the 60 min time point and mechanically hindered with metal grid patterns (FIG. 3B). Cross-shaped metal (e.g., Cr) diffusion barriers with a similar area coverage as that of grids (4% of surface area), does not impede ADAM10 recruitment and still allows ephrin-A1 radian transport. Importantly, we observe evidence of selective ephrin-A1 cleavage from the streptavidin anchor, indicating that the ADAM10 protease is active during the time span of CAD formation (FIG. 3C). These observations suggest a role for the central assembly in attenuating ephrin-A1 signals through the rapid recruitment of ADAM10 protease. After the ligand is detached from the apposed cell membrane, EphA2-expressing cells subsequently internalize and ultimately degrade the entire receptor-ligand complex, decreasing EphA2 activation. Therefore, the CAD functions to sequester ephrin-A1, attenuating its activity.

To quantify ADAM10 recruitment to receptor-ligand complexes, TIRFM was used to measure cell surface EphA2 and ADAM10 levels of an identical set of cells (n=477) that displayed a range of receptor spatial mutations. While the amount of EphA2 remained constant, the amount of recruited ADAM10 decreased with the size of the observed EphA2-ephrin-A1 clusters (FIG. 3B). In addition, the colocalization of ADAM10 with EphA2 (as measured by Pearson correlation coefficient, r) also decreased. Control experiments with cross-shaped metal lines and with 20 μm-pitch grids all confirm that these results are a consequence of receptor spatial organization and physical constraint. Cells cultured on two-component membranes displaying the cyclic RGD peptide along with ephrin-A1 displayed the same response to spatial mutations, confirming that this phenomenon is independent from RGD-mediated integrin adhesion and signaling (FIG. 20).

These spatial mutation experiments demonstrate that physical manipulation of EphA2-ephrin-A1 microcluster organization alters the cellular response to ephrin-A1. There are both spatial and mechanical aspects to these results. The cell applies force, via actomyosin contractility, to ligand-engaged EphA2 receptors. According to Newton's third law, grid barriers that block EphA2 transport in the spatial mutation must necessarily exert opposing forces on the receptor clusters. Spatial organization and mechanical forces are thus interconnected, resulting in an overall sensitivity of the EphA2 signaling pathway to spatio-mechanical aspects of the cellular microenvironment in which ephrin-A1 is displayed.

Example 8

Ephrin-A1 and mimics of it are known therapeutic agents for reversing the metastatic transformation of epithelial cells. Given the functionally altered role of EphA2 in this aggressive breast cancer cell line, the inventors decided to examine associations of spatial organization with aggressive behavior in cancer. The following protocol was applied. First, a collection of 26 human breast cancer cell lines with mutations that reflect the heterogeneity found in the disease space was selected for analysis. Second, the spatial organization of the EphA2 receptor was quantified at the single-cell level by measuring the radial distribution of ephrin-A1 within the supporting membrane (FIG. 5). A linear regression is then fit to the normalized radial distributions, and its slope was used as a CAD formation score for each cell line. Finally, this spatial organization score was then correlated to all currently available experimental data for the collection of cell lines.

Figure 4C:
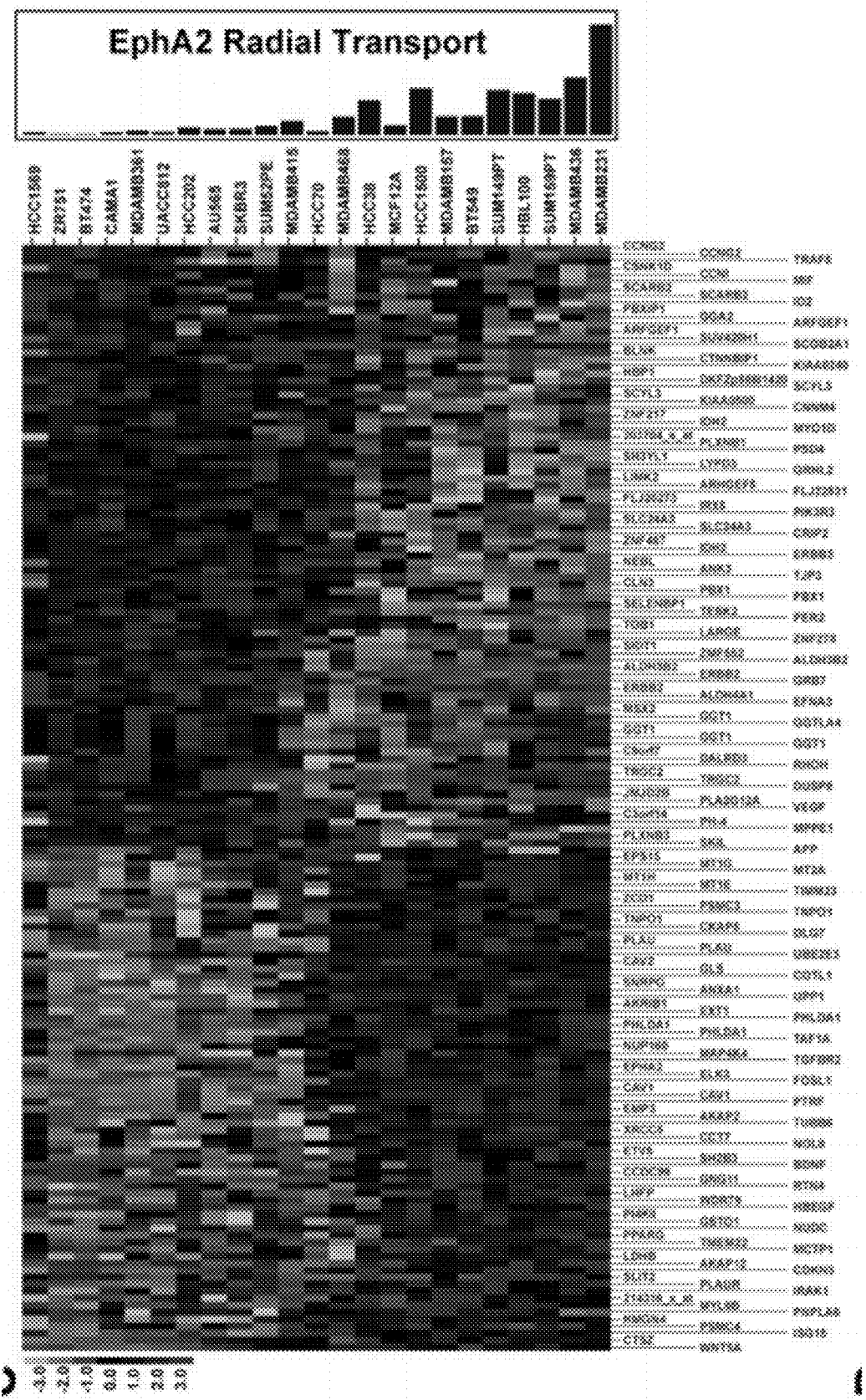

A strong correlation (r=0.91) between invasion potential, as measured using a modified Boyden chamber assay, and CAD formation was observed across the subset of the cell line library, those P-values for each gene or pathway shown in Tables 1-4. Additionally, a system-wide correlation of the spatial organization score to genomic and proteomic expression across the library predicted genes, proteins, and molecular pathways that may be involved in this phenotype (FIG. 4C, FIG. 22).

In order to investigate the generality of ligand-induced EphA2 transport beyond the MDA-MB-231 cell line, we examined a library of breast cancer cell lines. Such cell lines derived from primary tumors have been the most widely used models to elucidate how genes and signaling pathways regulate disease progression (R. M. Neve et al., *Cancer Cell* 10, 515 (2006). When a panel of cell lines is used as a system, rather than individually, it can serve as a powerful tool to identify and investigate recurrent markers for disease progression (T. Vargo-Gogola, J. M. Rosen, *Nat. Rev. Cancer* 7, 659 (2007)). Therefore, the propensity to radially transport the EphA2 receptor was characterized in 26 cell lines. An aliquot of ~50×10³ cells was plated onto ephrin-A1-functionalized supported membranes for 1 hr for each cell line. Live-cell fluorescence microscopy was used to image the resulting distribution of ligand under individual cells and a signature radial distribution function was determined for each cell type. Radial transport was not unique to MDA-MB-231, and instead, each cell line tested displayed a distinct and characteristic degree of ligand-induced receptor reorganization (FIG. 21). The diversity observed in EphA2 transport between different cell lines may result from the wide range of deregulations inherent to this library, as well as variance in EphA2 expression levels. To quantify the EphA2 radial transport phenotype, we parameterized the radial distribution functions for each cell line using linear regression, integration of area under the curve, and the ratio of peak-height to peak-width at half-maximum at t=60 min (FIG. 22). These different scoring methods were robust and led to strongly correlated values across the cell lines.

In order to identify the molecular signature of this spatial organization phenotype, we next performed large-scale analyses using the wealth of available data for the panel of cell lines. In this analysis, the measured radial transport scores serve as an unconventional spatial biomarker unique to each cell line and potentially associated with genomic, proteomic or phenotypic signatures in neoplasia. Invasion potentials, as measured using a modified Boyden chamber assay (R. M. Neve et al., *Cancer Cell* 10, 515 (2006)), were strongly linked (Pearson correlation r=0.91; p-value=7.5× $10^{-8}$) to the receptor radial transport phenotype across the library (FIG. 4A). In contrast, EphA2 mRNA and protein expression levels did not correlate as strongly with invasion potentials, and the correlation values (r) were 0.56 and 0.46, respectively, in agreement with previous reports (M. Macrae et al., *Cancer Cell* 8, 111 (2005); R. M. Neve et al., *Cancer Cell* 10, 515 (2006)). EphA2 translocation is distinct from expression, and a stronger degree of association is found between the scored receptor radial transport phenotype and invasion potentials across the breast cancer model, suggesting a link between EphA2 radial transport and tissue invasion. Additionally, a system-wide correlation of the spatial organization scores to protein and mRNA expression levels revealed 37 proteins (p-value<0.1) and 141 mRNA transcripts (p-value<1×$10^{-4}$; 158 probe sets) that are associated with this phenotype (FIG. 4B, C, tables S1-S2). Searches of the KEGG and BioCarta pathway analysis databases (G. Dennis et al., *GBE*. 4, 3 (2003)) revealed that radial transport was associated with the ErbB, p53, integrin, and MAPK signaling pathways (Tables 3-4). Notably, all of these pathways have been previously reported to associate with invasiveness and EphA2 signaling, we now show that they also associate with EphA2 spatial organization (M. Macrae et al., *Cancer Cell* 8, 111 (2005))

Example 9

Figure 4D:
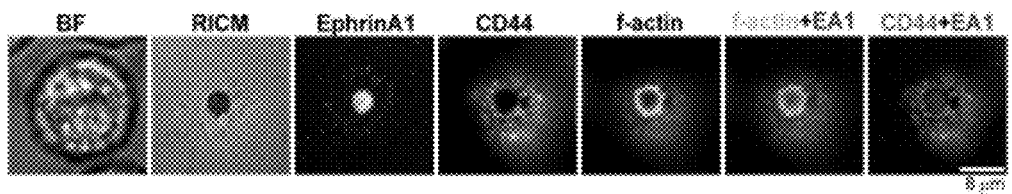

One of the proteins implicated in CAD formation is CD44 (HCAM), a cell membrane-bound glycoprotein involved in cell adhesion and migration. Interestingly, when we examined the spatial reorganization of CD44 upon supported membrane engagement, we discovered that CD44 anti-localizes with the assembly of EphA2 (FIG. 4D). This indicates that the system-wide screen was able to accurately predict the involvement of CD44 in the spatial sorting of Eph-ephrin complexes. Note that reorganization is not observed for other membrane-anchored signaling molecules such as integrin b, or caveolin 1, (FIG. 4B) even though caveolin 1 protein expression was also predicted to be involved in the pathways leading to EphA2 sorting.

In conclusion, we report a spatio-mechanical regulation of the EphA2 signaling pathway. Upon membrane-bound ligand stimulation, EphA2 is transported radially inwards by an actomyosin contractile process. Physical interference with this transport, which necessarily involves the imposition of opposing forces on EphA2, alters ligand-induced EphA2 activation as observed by the recruitment of the protease ADAM10 and cytoskeleton morphology. Quantitative measurement of centripetal receptor transport across a library of mammary epithelial cell lines reveals a high correlation with invasion potential and with specific gene and protein expression. These observations suggest that spatio-mechanical aspects of ephrin-A1 expressing cells and their surrounding tissue environment may functionally alter the response of EphA2 signaling systems and could play a contributing role in the onset and progression of cancer.

Thus, the hybrid live cell-supported membrane assay has provided the tools required for identification of an EphA2 spatial organization phenotype in a subset of breast cancer cell lines. This phenotype can be collected at the single-cell level in live cells and in a physiologically relevant manner. This discovery has yielded insight into the mechanisms for ligand-dependent EphA2 activation, thus providing a potential model for cell regulation thereof. Furthermore, CAD formation is a specific response that explains how receptors may become functionally altered without genetic or post transcriptional modifications to their fundamental chemical structure. Importantly, the ability to manipulate and measure spatial organization could become very useful in drug screening efforts aimed at personalized therapeutic approaches.

Example 10

This assay could perhaps also be used to diagnose autoimmune disorders. For example, myasthenia gravis often involves circulating antibodies secreted by the body's own immune cells that target the nicotinic acetylcholine receptor (nAChR) on the post-synaptic side of neuromuscular junctions within the body. This blocks the normal activation of this receptor, inhibiting the stimulative effects of acetylcholine and leading to fluctuating muscular weakness. One could envision presentation of CD4+ T cells, obtained from a patient suspected to suffer from myasthenia gravis, with antibodies raised against the nAChR on an SLB. Studies of the spatial organization and subsequent biochemical signaling that accompanies activation of such immune cells have been conducted (data not shown). Successful activation of T cells by these antibodies could be used to determine if the patient from whom the T cells were obtained suffered from this disorder.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended. In addition, where possible, combinations of the various embodiments, or combinations of the aspects of certain embodiments is considered to be within the scope of the disclosure.

The subject methods may include each of the activities associated with the assay and use of the information derived from the assay. As such, methodology implicit to the use of the assay and live cell device forms part of the invention. Such methodology may include using the assay or the live cell device in contexts not specifically detailed herein, and other applications. In addition, the experiments described herein can be detected by any optical means suitable for the physical context of the experiment. Accordingly, any tools or techniques such a microscopes or labels known in the art and adaptable to the context of the experiment are contemplated to accomplish the process of detecting receptor migration, position, and relocation within the cells being monitored. While the experiment limits detection to a defined region of the cell, in fact any part of the cell can be used for detection purposes, such as the whole cell or part of the cell. Typically the entire cell is viewed along with other whole cells, and detection of a single cell activity occurs in concert with detection of the activity of other neighboring cells.

More particularly, a number of methods according to the present invention involve the manner in which the assay is applied to a particular disease or condition, or cell type, or receptor-mediated activation pathway. Other methods concern the manner in which the system develops the physical context of the assay, and how the receptor redistribution is detected. Any method herein may be carried out in any order of the recited events which is logically possible, as well as in the recited order of events, or slight modifications of those events or the event order.

Also, it is contemplated that any optional feature of the inventive variations described may be set forth and claimed independently, or in combination with any one or more of the features described herein.

Reference to a singular item, includes the possibility that there is a plurality of the same items present. More specifically, as used herein and in the appended claims, the singular forms "a" and "the" include plural referents unless specifically stated otherwise. In other words, use of the articles allow for at least one molecule of the subject item in the description above as well as the claims below. It is further noted that the claims may be drafted to exclude any optional element. As such, this statement is intended to serve as antecedent basis for use of such exclusive terminology as "solely", "only" and the like in connection with the recitation of claim elements, or use of a negative limitation.

Without the use of such exclusive terminology, the term comprising in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language.

All references cited are incorporated by reference in their entirety. Although the foregoing invention has been described in detail for purposes of clarity of understanding, it is contemplated that certain modifications may be practiced within the scope of the appended claims.

TABLE 1

141 mRNA transcripts (158 probesets) displayed significant correlation ($p < 1 \times 10^{-4}$, FDR $< 5 \times 10^{-3}$) with EphA2 radial transport phenotype. Their respective correlations with invasion potential are also shown. All selected mRNA biomarkers display the same type of correlation with the EphA2 reorganization phenotype as with invasion potential.

| | EphA2 Radial Transport | | | Invasion potential | | |
|---|---|---|---|---|---|---|
| Gene ID | p-value | FDR | Type of Correlation | p-value | FDR | Type of Correlation |
| ERBB2 | 4.09E−07 | 7.59E−04 | − | 5.51E−04 | 6.32E−03 | − |
| SCYL3 | 7.43E−07 | 7.59E−04 | − | 2.40E−04 | 5.12E−03 | − |
| FOSL1 | 1.03E−06 | 7.59E−04 | + | 1.04E−06 | 1.17E−03 | + |
| SNRPG | 1.10E−06 | 7.59E−04 | + | 2.51E−03 | 1.07E−02 | + |
| HBP1 | 1.13E−06 | 7.59E−04 | − | 5.88E−02 | 4.95E−02 | − |
| ARFGEF1 | 1.95E−06 | 9.18E−04 | − | 1.42E−01 | 8.62E−02 | − |
| PLXNB1 | 2.58E−06 | 9.18E−04 | − | 1.45E−05 | 2.66E−03 | − |
| PHLDA1 | 2.65E−06 | 9.18E−04 | + | 1.14E−04 | 4.46E−03 | + |
| ALDH4A1 | 2.95E−06 | 9.18E−04 | − | 1.22E−02 | 2.20E−02 | − |
| TIMM23 | 3.17E−06 | 9.18E−04 | + | 4.70E−03 | 1.42E−02 | + |
| KIAA0240 | 3.24E−06 | 9.18E−04 | − | 3.56E−03 | 1.25E−02 | − |
| PLAU | 3.44E−06 | 9.18E−04 | + | 4.07E−03 | 1.33E−02 | + |
| GGT1 | 4.21E−06 | 9.18E−04 | − | 1.15E−01 | 7.52E−02 | − |
| MT1G | 4.36E−06 | 9.18E−04 | + | 5.04E−03 | 1.47E−02 | + |
| MT2A | 4.37E−06 | 9.18E−04 | + | 3.23E−03 | 1.20E−02 | + |
| CCNG2 | 4.50E−06 | 9.18E−04 | − | 2.95E−01 | 1.44E−01 | − |
| ARFGEF1 | 4.78E−06 | 9.18E−04 | − | 1.67E−01 | 9.60E−02 | − |
| CSNK1D | 5.15E−06 | 9.18E−04 | − | 4.09E−05 | 3.71E−03 | − |
| CRIP2 | 5.32E−06 | 9.18E−04 | − | 1.06E−03 | 7.61E−03 | − |
| CKAP5 | 6.05E−06 | 9.18E−04 | + | 3.64E−03 | 1.27E−02 | + |
| PBXIP1 | 6.12E−06 | 9.18E−04 | − | 1.11E−02 | 2.10E−02 | − |
| NEBL | 6.40E−06 | 9.18E−04 | − | 6.73E−05 | 3.88E−03 | − |
| UBE2E3 | 6.89E−06 | 9.18E−04 | + | 5.29E−03 | 1.49E−02 | + |
| ERBB3 | 7.10E−06 | 9.18E−04 | − | 1.46E−04 | 4.56E−03 | − |
| SH3YL1 | 7.32E−06 | 9.18E−04 | − | 2.54E−04 | 5.24E−03 | − |
| DKFZp586I1420 | 7.68E−06 | 9.18E−04 | − | 8.41E−03 | 1.83E−02 | − |
| SCYL3 | 7.69E−06 | 9.18E−04 | − | 7.68E−04 | 6.82E−03 | − |
| PTRF | 7.83E−06 | 9.18E−04 | + | 5.44E−04 | 6.28E−03 | + |
| ZCD1 | 8.22E−06 | 9.18E−04 | + | 6.66E−03 | 1.65E−02 | + |
| CAV2 | 8.34E−06 | 9.18E−04 | + | 2.52E−04 | 5.24E−03 | + |
| PHLDA1 | 8.87E−06 | 9.18E−04 | + | 4.06E−03 | 1.33E−02 | + |
| GRB7 | 9.28E−06 | 9.18E−04 | − | 7.04E−04 | 6.82E−03 | − |
| MYO1D | 9.33E−06 | 9.18E−04 | − | 7.92E−03 | 1.80E−02 | − |
| PI4KII | 9.42E−06 | 9.18E−04 | + | 1.25E−02 | 2.23E−02 | + |
| GGT1 | 1.04E−05 | 9.18E−04 | − | 5.12E−02 | 4.56E−02 | − |
| GRHL2 | 1.04E−05 | 9.18E−04 | − | 4.76E−03 | 1.43E−02 | − |
| FLJ22531 | 1.07E−05 | 9.18E−04 | − | 1.87E−02 | 2.68E−02 | − |
| ZNF217 | 1.08E−05 | 9.18E−04 | − | 6.06E−03 | 1.57E−02 | − |
| TAF1A | 1.09E−05 | 9.18E−04 | + | 4.33E−02 | 4.15E−02 | + |
| CCNG2 | 1.09E−05 | 9.18E−04 | − | 1.97E−01 | 1.08E−01 | − |
| CAV1 | 1.12E−05 | 9.22E−04 | + | 1.32E−03 | 8.25E−03 | + |
| GLS | 1.17E−05 | 9.32E−04 | + | 4.08E−03 | 1.33E−02 | + |
| DALRD3 | 1.19E−05 | 9.32E−04 | − | 5.85E−04 | 6.41E−03 | − |
| TGFBR2 | 1.22E−05 | 9.32E−04 | + | 2.93E−04 | 5.52E−03 | + |
| PSD4 | 1.30E−05 | 9.75E−04 | − | 1.17E−03 | 7.99E−03 | − |
| MT1H | 1.39E−05 | 1.01E−03 | + | 1.58E−02 | 2.47E−02 | + |
| CNNM4 | 1.43E−05 | 1.02E−03 | − | 8.72E−05 | 3.93E−03 | − |
| PBX1 | 1.45E−05 | 1.02E−03 | − | 7.31E−03 | 1.73E−02 | − |
| MAP4K4 | 1.74E−05 | 1.17E−03 | + | 3.42E−02 | 3.64E−02 | + |
| SCGB2A1 | 1.74E−05 | 1.17E−03 | − | 3.88E−03 | 1.30E−02 | − |
| EPHA2 | 1.81E−05 | 1.20E−03 | + | 6.29E−05 | 3.88E−03 | + |
| ELK3 | 2.01E−05 | 1.26E−03 | + | 1.16E−03 | 7.97E−03 | + |
| C3orf14 | 2.03E−05 | 1.26E−03 | − | 1.02E−02 | 1.99E−02 | − |
| BDNF | 2.10E−05 | 1.26E−03 | + | 1.53E−03 | 8.68E−03 | + |
| ERBB2 | 2.11E−05 | 1.26E−03 | − | 2.73E−03 | 1.13E−02 | − |
| DLG7 | 2.19E−05 | 1.26E−03 | + | 1.66E−03 | 8.91E−03 | + |
| TMEM22 | 2.21E−05 | 1.26E−03 | + | 7.12E−03 | 1.70E−02 | + |
| SELENBP1 | 2.21E−05 | 1.26E−03 | − | 9.06E−05 | 4.03E−03 | − |
| BLNK | 2.24E−05 | 1.26E−03 | − | 1.69E−03 | 9.03E−03 | − |
| SLC24A3 | 2.34E−05 | 1.26E−03 | − | 9.62E−04 | 7.30E−03 | − |
| EFNA3 | 2.36E−05 | 1.26E−03 | − | 1.27E−02 | 2.23E−02 | − |
| MPPE1 | 2.45E−05 | 1.26E−03 | − | 1.55E−03 | 8.69E−03 | − |
| CCNI | 2.47E−05 | 1.26E−03 | − | 1.17E−02 | 2.16E−02 | − |

TABLE 1-continued 141 mRNA transcripts (158 probesets) displayed significant correlation ($p < 1 \times 10^{-4}$, FDR $< 5 \times 10^{-3}$) with EphA2 radial transport phenotype. Their respective correlations with invasion potential are also shown. All selected mRNA biomarkers display the same type of correlation with the EphA2 reorganization phenotype as with invasion potential.

| | EphA2 Radial Transport | | | Invasion potential | | |
|---|---|---|---|---|---|---|
| Gene ID | p-value | FDR | Type of Correlation | p-value | FDR | Type of Correlation |
| MIF | 2.47E−05 | 1.26E−03 | − | 9.13E−03 | 1.91E−02 | − |
| CTSZ | 2.47E−05 | 1.26E−03 | + | 9.94E−03 | 1.96E−02 | + |
| PLXNB3 | 2.47E−05 | 1.26E−03 | − | 2.85E−03 | 1.14E−02 | − |
| SCARB2 | 2.67E−05 | 1.32E−03 | − | 6.62E−02 | 5.30E−02 | − |
| IRX5 | 2.70E−05 | 1.32E−03 | − | 1.87E−03 | 9.44E−03 | − |
| SUV420H1 | 2.73E−05 | 1.32E−03 | − | 1.21E−03 | 8.13E−03 | − |
| PLAU | 2.77E−05 | 1.32E−03 | + | 3.23E−03 | 1.20E−02 | + |
| CTNNBIP1 | 2.78E−05 | 1.32E−03 | − | 7.70E−02 | 5.82E−02 | − |
| ZNF552 | 2.89E−05 | 1.33E−03 | − | 3.74E−02 | 3.81E−02 | − |
| TRAF5 | 2.97E−05 | 1.33E−03 | − | 1.93E−02 | 2.71E−02 | − |
| ZNF467 | 2.99E−05 | 1.33E−03 | − | 1.43E−04 | 4.56E−03 | − |
| PBX1 | 3.03E−05 | 1.33E−03 | − | 5.34E−03 | 1.49E−02 | − |
| ZNF278 | 3.03E−05 | 1.33E−03 | − | 2.38E−03 | 1.05E−02 | − |
| LHFP | 3.04E−05 | 1.33E−03 | + | 4.63E−04 | 6.07E−03 | + |
| EXT1 | 3.16E−05 | 1.37E−03 | + | 2.13E−02 | 2.86E−02 | + |
| CCDC99 | 3.26E−05 | 1.38E−03 | + | 6.18E−04 | 6.55E−03 | + |
| TNPO1 | 3.27E−05 | 1.38E−03 | + | 2.02E−04 | 4.88E−03 | + |
| IDH2 | 3.56E−05 | 1.48E−03 | − | 1.15E−03 | 7.95E−03 | − |
| LARGE | 3.66E−05 | 1.50E−03 | − | 5.37E−04 | 6.22E−03 | − |
| XRCC5 | 4.11E−05 | 1.59E−03 | + | 5.22E−04 | 6.13E−03 | + |
| UPP1 | 4.13E−05 | 1.59E−03 | + | 2.60E−03 | 1.10E−02 | + |
| MT1E | 4.13E−05 | 1.59E−03 | + | 2.06E−03 | 9.86E−03 | + |
| NUP160 | 4.14E−05 | 1.59E−03 | + | 1.55E−02 | 2.44E−02 | + |
| LYPD3 | 4.17E−05 | 1.59E−03 | − | 7.19E−05 | 3.88E−03 | − |
| EMP3 | 4.19E−05 | 1.59E−03 | + | 5.90E−04 | 6.41E−03 | + |
| ALDH3B2 | 4.19E−05 | 1.59E−03 | − | 7.38E−04 | 6.82E−03 | − |
| PHLDA1 | 4.28E−05 | 1.60E−03 | + | 1.61E−03 | 8.82E−03 | + |
| PER2 | 4.32E−05 | 1.60E−03 | − | 7.98E−05 | 3.88E−03 | − |
| AKAP12 | 4.38E−05 | 1.60E−03 | + | 1.51E−04 | 4.56E−03 | + |
| MSX2 | 4.40E−05 | 1.60E−03 | − | 3.09E−02 | 3.47E−02 | − |
| WDR79 | 4.66E−05 | 1.65E−03 | + | 1.75E−02 | 2.60E−02 | + |
| COTL1 | 4.72E−05 | 1.65E−03 | + | 2.17E−04 | 4.88E−03 | + |
| ETV5 | 4.79E−05 | 1.65E−03 | + | 3.35E−03 | 1.21E−02 | + |
| SCARB2 | 4.80E−05 | 1.65E−03 | − | 1.10E−01 | 7.30E−02 | − |
| HMGN4 | 4.85E−05 | 1.65E−03 | + | 1.12E−02 | 2.10E−02 | + |
| TJP3 | 4.86E−05 | 1.65E−03 | − | 9.11E−06 | 2.55E−03 | − |
| IDH2 | 4.95E−05 | 1.65E−03 | − | 8.77E−04 | 7.05E−03 | − |
| PIK3R3 | 5.00E−05 | 1.65E−03 | − | 1.02E−03 | 7.54E−03 | − |
| RTN4 | 5.06E−05 | 1.65E−03 | + | 4.35E−04 | 6.06E−03 | + |
| HBEGF | 5.10E−05 | 1.65E−03 | + | 1.94E−04 | 4.88E−03 | + |
| MYL6B | 5.14E−05 | 1.65E−03 | + | 9.50E−02 | 6.62E−02 | + |
| AKR1B1 | 5.19E−05 | 1.65E−03 | + | 1.84E−04 | 4.88E−03 | + |
| LIMK2 | 5.20E−05 | 1.65E−03 | − | 4.22E−04 | 6.06E−03 | − |
| ANK3 | 5.42E−05 | 1.68E−03 | − | 7.35E−04 | 6.82E−03 | − |
| PLA2G12A | 5.50E−05 | 1.68E−03 | − | 1.39E−02 | 2.33E−02 | − |
| KIAA0500 | 5.51E−05 | 1.68E−03 | − | 1.14E−03 | 7.93E−03 | − |
| LDHB | 5.51E−05 | 1.68E−03 | + | 9.19E−03 | 1.91E−02 | + |
| Transcribed locus | 5.53E−05 | 1.68E−03 | + | 8.29E−03 | 1.83E−02 | + |
| GGA2 | 5.60E−05 | 1.68E−03 | − | 4.88E−02 | 4.44E−02 | − |
| PLAUR | 5.70E−05 | 1.70E−03 | + | 2.85E−02 | 3.32E−02 | + |
| SIDT1 | 5.80E−05 | 1.70E−03 | − | 2.91E−05 | 3.40E−03 | − |
| TRGC2 | 5.80E−05 | 1.70E−03 | − | 6.47E−02 | 5.23E−02 | − |
| TNPO1 | 5.88E−05 | 1.70E−03 | + | 8.78E−03 | 1.88E−02 | + |
| SH2B3 | 5.91E−05 | 1.70E−03 | + | 2.25E−03 | 1.02E−02 | + |
| ANXA1 | 5.94E−05 | 1.70E−03 | + | 3.07E−03 | 1.17E−02 | + |
| SLIT2 | 6.00E−05 | 1.70E−03 | + | 1.72E−02 | 2.58E−02 | + |
| DUSP8 | 6.17E−05 | 1.72E−03 | − | 5.69E−02 | 1.54E−02 | − |
| EPS15 | 6.20E−05 | 1.72E−03 | + | 2.19E−04 | 4.88E−03 | + |
| ID2 | 6.25E−05 | 1.72E−03 | − | 6.86E−02 | 5.42E−02 | − |
| TRGC2 | 6.26E−05 | 1.72E−03 | − | 1.37E−01 | 8.38E−02 | − |
| AKAP2 | 6.44E−05 | 1.75E−03 | + | 3.02E−03 | 1.17E−02 | + |
| GGTLA4 | 6.53E−05 | 1.76E−03 | − | 1.69E−01 | 9.64E−02 | − |
| GGT1 | 6.58E−05 | 1.76E−03 | − | 3.59E−02 | 3.72E−02 | − |
| MCTP1 | 6.68E−05 | 1.77E−03 | + | 3.28E−03 | 1.20E−02 | + |
| SKIL | 6.71E−05 | 1.77E−03 | − | 3.34E−01 | 1.57E−01 | − |
| VEGF | 6.95E−05 | 1.82E−03 | − | 1.16E−02 | 2.15E−02 | − |
| CLN3 | 7.05E−05 | 1.83E−03 | − | 4.30E−03 | 1.36E−02 | − |
| WNT5A | 7.24E−05 | 1.86E−03 | + | 2.44E−03 | 1.07E−02 | + |
| ARHGEF5 | 7.34E−05 | 1.87E−03 | − | 1.08E−05 | 2.61E−03 | − |
| GSTO1 | 7.39E−05 | 1.87E−03 | + | 3.44E−03 | 1.23E−02 | + |

TABLE 1-continued 141 mRNA transcripts (158 probesets) displayed significant correlation ($p < 1 \times 10^{-4}$, FDR $< 5 \times 10^{-3}$) with EphA2 radial transport phenotype. Their respective correlations with invasion potential are also shown. All selected mRNA biomarkers display the same type of correlation with the EphA2 reorganization phenotype as with invasion potential.

| Gene ID | EphA2 Radial Transport | | | Invasion potential | | |
|---|---|---|---|---|---|---|
| | p-value | FDR | Type of Correlation | p-value | FDR | Type of Correlation |
| IRAK1 | 7.54E−05 | 1.90E−03 | + | 7.81E−02 | 5.87E−02 | + |
| PH-4 | 7.60E−05 | 1.90E−03 | − | 4.30E−04 | 6.06E−03 | − |
| CCT7 | 7.73E−05 | 1.92E−03 | + | 5.65E−03 | 1.54E−02 | + |
| GGT1 | 7.84E−05 | 1.92E−03 | − | 1.36E−01 | 8.37E−02 | − |
| SLC24A3 | 7.84E−05 | 1.92E−03 | − | 2.99E−04 | 5.58E−03 | − |
| C9orf7 | 8.12E−05 | 1.96E−03 | − | 1.18E−03 | 8.02E−03 | − |
| RREB1 | 8.15E−05 | 1.96E−03 | − | 8.28E−03 | 1.83E−02 | − |
| CAV1 | 8.26E−05 | 1.97E−03 | + | 2.49E−03 | 1.07E−02 | + |
| TUBB6 | 8.30E−05 | 1.97E−03 | + | 3.14E−02 | 3.50E−02 | + |
| FLJ20273 | 8.41E−05 | 1.98E−03 | − | 1.01E−02 | 1.98E−02 | − |
| APP | 8.53E−05 | 2.00E−03 | − | 1.55E−02 | 2.45E−02 | − |
| CDKN3 | 8.66E−05 | 2.00E−03 | + | 6.43E−03 | 1.61E−02 | + |
| GNG11 | 8.67E−05 | 2.00E−03 | + | 7.78E−04 | 6.82E−03 | + |
| NUDC | 8.87E−05 | 2.01E−03 | + | 4.93E−03 | 1.46E−02 | + |
| PPARG | 8.88E−05 | 2.01E−03 | + | 9.91E−03 | 1.96E−02 | + |
| NOL8 | 8.88E−05 | 2.01E−03 | + | 9.04E−03 | 1.90E−02 | + |
| RHOH | 9.05E−05 | 2.02E−03 | − | 2.36E−02 | 3.02E−02 | − |
| TOB1 | 9.11E−05 | 2.02E−03 | − | 1.93E−04 | 4.88E−03 | − |
| ISG15 | 9.13E−05 | 2.02E−03 | + | 7.17E−03 | 1.71E−02 | + |
| ALDH3B2 | 9.39E−05 | 2.07E−03 | − | 3.39E−04 | 5.61E−03 | − |
| PSMC3 | 9.54E−05 | 2.09E−03 | + | 2.13E−02 | 2.86E−02 | + |
| PSMC4 | 9.76E−05 | 2.11E−03 | + | 6.27E−01 | 2.48E−01 | + |
| PNPLA6 | 9.77E−05 | 2.11E−03 | + | 3.67E−02 | 3.78E−02 | + |
| TESK2 | 9.82E−05 | 2.11E−03 | − | 2.46E−02 | 3.09E−02 | − |
| JMJD2B | 9.91E−05 | 2.11E−03 | − | 1.51E−03 | 8.63E−03 | − |

TABLE 2

37 proteins displayed significant correlation ($p < 0.1$) with EphA2 radial transport phenotype. Their respective correlations with invasion potential are also shown. All selected protein biomarkers display the same type of correlation with the EphA2 reorganization phenotype as with invasion potential.

| Protein ID | EphA2 Radial Transport | | Invasion potential | |
|---|---|---|---|---|
| | p-value | Type of Correlation | p-value | Type of Correlation |
| EPHA2 | 1.46E−04 | + | 9.77E−03 | + |
| CAV1_UP | 4.16E−04 | + | 2.13E−02 | + |
| CAV1_LOW | 4.56E−04 | + | 2.30E−02 | + |
| EFNA1 | 5.01E−04 | − | 3.47E−01 | + |
| CAV2_LOW | 1.09E−03 | + | 1.88E−02 | + |
| ACTN1 | 1.16E−03 | + | 4.33E−02 | + |
| LYN | 1.53E−03 | + | 1.61E−01 | + |
| CD44 | 1.54E−03 | + | 1.62E−03 | + |
| CAV2_UP | 1.84E−03 | + | 5.82E−03 | − |
| JUN | 2.55E−03 | + | 5.47E−03 | − |
| MDM2 | 3.11E−03 | − | 3.91E−02 | − |
| ERBB2-P | 3.17E−03 | − | 9.94E−04 | − |
| TYK2 | 4.00E−03 | + | 3.14E−01 | + |
| ERBB2 | 4.62E−03 | − | 6.59E−03 | + |
| RB1 | 4.85E−03 | − | 1.75E−01 | + |
| SPDEF | 4.93E−03 | − | 6.08E−03 | + |
| ITGB1_UP | 6.29E−03 | + | 2.70E−02 | − |
| CDK1 | 6.37E−03 | + | 1.00E−02 | + |
| CDH1_LOW | 8.57E−03 | − | 2.90E−01 | − |
| CDKN1A | 8.87E−03 | + | 7.72E−01 | + |
| CBL_LOW | 9.51E−03 | + | 5.17E−02 | + |
| IRS1 | 1.04E−02 | + | 6.77E−02 | + |
| ESR1 | 1.04E−02 | − | 8.62E−02 | − |
| SRC | 2.70E−02 | + | 9.23E−01 | + |
| CCNE1 | 3.85E−02 | − | 3.93E−01 | − |
| CDH1_UP | 3.95E−02 | − | 1.89E−01 | − |
| SFN | 4.93E−02 | + | 4.11E−01 | + |
| TP53 | 5.28E−02 | + | 1.12E−02 | − |
| SHC1_P66 | 5.49E−02 | + | 1.22E−01 | − |
| SKP2 | 5.58E−02 | + | 6.24E−01 | + |
| MAPK3 | 5.98E−02 | + | 4.32E−01 | + |
| CDKN1B | 6.08E−02 | − | 4.84E−01 | − |
| AKT1-P | 7.39E−02 | − | 3.68E−01 | − |
| MEK-P | 7.67E−02 | + | 8.76E−01 | + |
| IGF1R | 8.06E−02 | + | 1.88E−01 | + |
| ERBB3 | 8.16E−02 | − | 3.80E−03 | + |
| BAG4 | 9.42E−02 | + | 2.69E−03 | + |

TABLE 3

15 KEGG pathways displayed significant correlation (FDR < 5%) with EphA2 radial transport phenotype.

| KEGG Pathway | p-value | FDR (%) | Genes |
|---|---|---|---|
| ErbB signaling pathway | 1.25E−09 | 1.57E−06 | CDKN1A, ERBB2, SRC, JUN, CDKN1B, AKT1, SHC1, ERBB3, MAPK3, CBL, |
| Prostate cancer | 1.55E−09 | 1.95E−06 | RB1, CDKN1A, ERBB2, MDM2, TP53, CCNE1, CDKN1B, AKT1, IGF1R, MAPK3, |
| Chronic myeloid leukemia | 1.05E−08 | 1.31E−05 | RB1, CDKN1A, MDM2, TP53, CDKN1B, AKT1, SHC1, MAPK3, CBL, |
| Glioma | 5.90E−08 | 7.40E−05 | RB1, CDKN1A, MDM2, TP53, AKT1, SHC1, IGF1R, MAPK3, |
| Bladder cancer | 1.27E−07 | 1.59E−04 | RB1, CDKN1A, ERBB2, MDM2, TP53, CDH1, MAPK3, |
| Melanoma | 1.59E−07 | 1.99E−04 | RB1, CDKN1A, MDM2, TP53, CDH1, AKT1, IGF1R, MAPK3, |
| Focal adhesion | 1.84E−07 | 2.31E−04 | ERBB2, CAV1, SRC, CAV2, ACTN1, JUN, AKT1, ITGB1, SHC1, IGF1R, MAPK3, |
| Cell cycle | 5.00E−06 | 6.28E−03 | RB1, SKP2, CDKN1A, MDM2, SFN, TP53, CCNE1, CDKN1B, |
| Small cell lung cancer | 1.36E−05 | 1.71E−02 | RB1, SKP2, TP53, CCNE1, CDKN1B, AKT1, ITGB1, |
| Adherens junction | 8.70E−05 | 0.11 | ERBB2, SRC, CDH1, ACTN1, IGF1R, MAPK3, |
| Endometrial cancer | 2.52E−04 | 0.32 | ERBB2, TP53, CDH1, AKT1, MAPK3, |
| Non-small cell lung cancer | 2.93E−04 | 0.37 | RB1, ERBB2, TP53, AKT1, MAPK3, |
| p53 signaling pathway | 8.23E−04 | 1.03 | CDKN1A, MDM2, SFN, TP53, CCNE1, |
| Pancreatic cancer | 1.08E−03 | 1.34 | RB1, ERBB2, TP53, AKT1, MAPK3, |
| Colorectal cancer | 1.90E−03 | 2.36 | TP53, JUN, AKT1, IGF1R, MAPK3, |

TABLE 4

13 Biocarta pathways displayed significant correlation (FDR < 5%) with EphA2 radial transport phenotype.

| Biocarta Pathway | p-value | FDR (%) | Genes |
|---|---|---|---|
| Influence of Ras and Rho proteins on G1 to S Transition | 3.00E−05 | 0.04 | RB1, CDKN1A, CCNE1, CDKN1B, AKT1, MAPK3, |
| Cell Cycle G1/S Check Point | 4.46E−05 | 0.06 | RB1, SKP2, CDKN1A, TP53, CCNE1, CDKN1B, |
| p53 Signaling Pathway | 8.28E−05 | 0.11 | RB1, CDKN1A, MDM2, TP53, CCNE1, |
| Multiple antiapoptotic pathways from IGF-1R signaling lead to BAD phosphorylation | 1.71E−04 | 0.23 | AKT1, SHC1, IGF1R, MAPK3, IRS1, |
| Integrin Signaling Pathway | 1.89E−04 | 0.26 | CAV1, SRC, JUN, ITGB1, SHC1, MAPK3, |
| IGF-1 Signaling Pathway | 2.11E−04 | 0.28 | JUN, SHC1, IGF1R, MAPK3, IRS1, |
| PTEN dependent cell cycle arrest and apoptosis | 2.11E−04 | 0.28 | CDKN1B, AKT1, ITGB1, SHC1, MAPK3, |
| Trefoil Factors Initiate Mucosal Healing | 2.58E−04 | 0.35 | ERBB2, AKT1, ITGB1, SHC1, MAPK3, |
| Role of ERBB2 in Signal Transduction and Oncology | 2.58E−04 | 0.35 | ERBB2, ESR1, SHC1, ERBB3, MAPK3, |
| Regulation of p27 Phosphorylation during Cell Cycle Progression | 9.42E−04 | 1.27 | RB1, SKP2, CCNE1, CDKN1B, |
| Erk1/Erk2 Mapk Signaling pathway | 1.22E−03 | 1.63 | SRC, ITGB1, SHC1, IGF1R, MAPK3, |
| Sprouty regulation of tyrosine kinase signals | 1.47E−03 | 1.96 | SRC, SHC1, MAPK3, CBL, |
| IL-2 Receptor Beta Chain in T cell Activation | 2.39E−03 | 3.18 | AKT1, SHC1, MAPK3, IRS1, CBL, |

What is claimed:

1. An assay comprising the steps of:
(a) providing a live cell derived from a subject suspected of having cancer, wherein the live cell having a plurality of a Eph receptor on the cell surface, said live cell being capable of activating Eph receptor redistribution on the surface of the cell, the Eph receptor capable of binding a ligand, whereupon binding of the ligand by said plurality of a Eph receptor activates receptor redistribution and results in a detectable pattern of the plurality of Eph receptors distributed on the surface of the cell;

(b) providing a physical context wherein the physical context further comprises a supported lipid bilayer having the ligand displayed or attached thereto;

(c) contacting said live cell to the ligand attached to said physical context;

(d) detecting and quantifying the pattern of Eph receptor redistribution and activation of said pattern of Eph receptor distribution on the surface of the cell where said live cell is attached, wherein the quantifying step (d) further comprises determining a normalized radial transport or radial distribution score of the pattern of Eph receptor redistribution;

(e) correlating said detectable pattern of Eph receptor redistribution to a signature for aggressive cancer cells or metastatic cancer cells; and (f) providing a diagnosis of the subject's condition based on said correlation to the aggressive or metastatic cancer cells and administering a therapeutic appropriate to treat such cancer cells in said subject.

2. The assay of claim 1, wherein the Eph receptor is labeled with a detectable label and the pattern of labeled Eph receptors distributed on the cell surface is detected by an optical label tracking the labeled Eph receptor, and label intensity quantifies the signature.

3. The assay of claim 1, wherein the physical context further comprising a grid or diffusion barriers, thereby providing grid areas within the grid or diffusion barriers and the supported lipid bilayer is provided in the grid areas.

4. The assay of claim 1, wherein the ligand is a cell-surface protein.

5. The assay of claim 1, further comprising components for detection of mRNA expression of a marker selected from EFNA1, GRB7, ITGB1, ITGB2, CAV2 or LYN after ligand-receptor binding.

6. The assay of claim 5, comprising components for detection of mRNA for each of EFNA1, GRB7, ITGB1, ITGB2, CAV2 and LYN genes in a profile to determine a likelihood of metastasis.

7. The assay of claim 6, wherein the gene profile corroborates the Eph receptor distribution signature and both identify a metastatic condition.

8. The assay of claim 1, further comprising contacting a test drug with the physical context, wherein the physical context is adapted to allow contact of the test drug with the plurality of a Eph receptor on said cell to test for modulation of a signature for aggressive or metastatic cancer cells.

9. The assay of claim 1, wherein the ligand is a protein, antibody, peptide, nucleic acid, small molecule, drug, or carbohydrate.

10. The assay of claim 2, wherein the Eph receptor is distributed over an approximate span of the cell surface between about 10 nanometers and about 10 microns.

11. The assay of claim 2, wherein the detectable label is a fluorescent label.

12. The assay of claim 1, wherein detecting step (d) comprises observing and measuring the activation of Eph receptor redistribution and wherein the detectable pattern of Eph receptor redistribution comprises clusters of Eph receptors on the surface of the cell.

13. The assay of claim 9, wherein the ligand is labeled with a detectable label.

* * * * *